(12) United States Patent
Dinville et al.

(10) Patent No.: US 9,326,797 B2
(45) Date of Patent: May 3, 2016

(54) INTERSPINOUS IMPLANT AND INSTRUMENT FOR IMPLANTING AN INTERSPINOUS IMPLANT

(71) Applicant: LDR MEDICAL, Rosières Près Troyes (FR)

(72) Inventors: Herve Dinville, Saint Parres Aux Tertres (FR); Samuel Lequette, Pessac (FR); Alexandre Jodaitis, Morlanwelz (BE); Richard Wohns, Puyallup, WA (US); Philippe Tisserand, Cabestany (FR); Laurent Zabee, Laxou (FR)

(73) Assignee: LDR Medical, Rosieres Pres Troyes (FR)

( * ) Notice: Subject to any disclaimer, the term of this patent is extended or adjusted under 35 U.S.C. 154(b) by 0 days.

(21) Appl. No.: 14/252,754

(22) Filed: Apr. 14, 2014

(65) Prior Publication Data

US 2014/0228885 A1 Aug. 14, 2014

Related U.S. Application Data

(63) Continuation of application No. 13/369,650, filed on Feb. 9, 2012, now Pat. No. 8,696,709.

(30) Foreign Application Priority Data

Jun. 30, 2011 (FR) ........................................ 11 55908
Feb. 3, 2012 (FR) ........................................ 12 51031

(51) Int. Cl.
*A61B 17/70* (2006.01)

(52) U.S. Cl.
CPC ......... *A61B 17/7067* (2013.01); *A61B 17/7065* (2013.01); *A61B 17/7068* (2013.01); *A61B 17/7071* (2013.01)

(58) Field of Classification Search
CPC ........... A61B 17/7062; A61B 17/7065; A61B 17/7068
USPC ...................... 606/246–249; 623/17.11–17.16
See application file for complete search history.

(56) References Cited

U.S. PATENT DOCUMENTS

| | | | |
|---|---|---|---|
| 8,123,782 B2* | 2/2012 | Altarac | A61B 17/7065 606/248 |
| 8,382,801 B2* | 2/2013 | Lamborne | A61B 17/7068 606/246 |
| 8,430,911 B2* | 4/2013 | Chin et al. | 606/248 |
| 2009/0292316 A1* | 11/2009 | Hess | 606/249 |
| 2010/0087860 A1* | 4/2010 | Chin et al. | 606/249 |
| 2010/0152775 A1* | 6/2010 | Seifert | A61B 17/3468 606/249 |

* cited by examiner

*Primary Examiner* — Ellen C Hammond
*Assistant Examiner* — Christina Negrellirodriguez
(74) *Attorney, Agent, or Firm* — Denko Lauff LLP

(57) ABSTRACT

The present invention relates to an interspinous implant, intended to be implanted between two adjacent dorsal spines, each including an upper edge, a lower edge and two opposed lateral faces, wherein the implant includes at least one body with dimensions arranged so as to maintain or restore a distance between the adjacent edges of the two spinous processes and including at least two wings extending so that at least a part of each wing lies along at least a part of one lateral face of one of the two spinous processes and, additionally, at least one retainer for the implant, designed to retain the body of the implant between the two spinous processes and to be inserted from the same lateral face as the body.

6 Claims, 48 Drawing Sheets

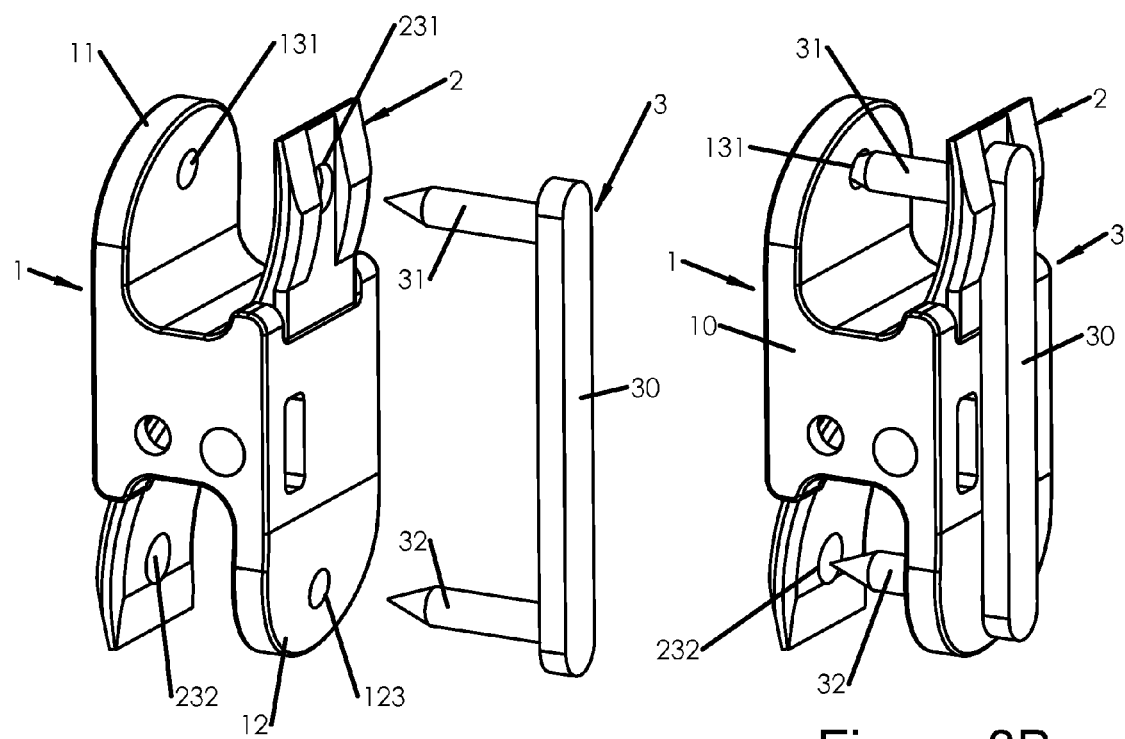
Figure 8A
Figure 8B
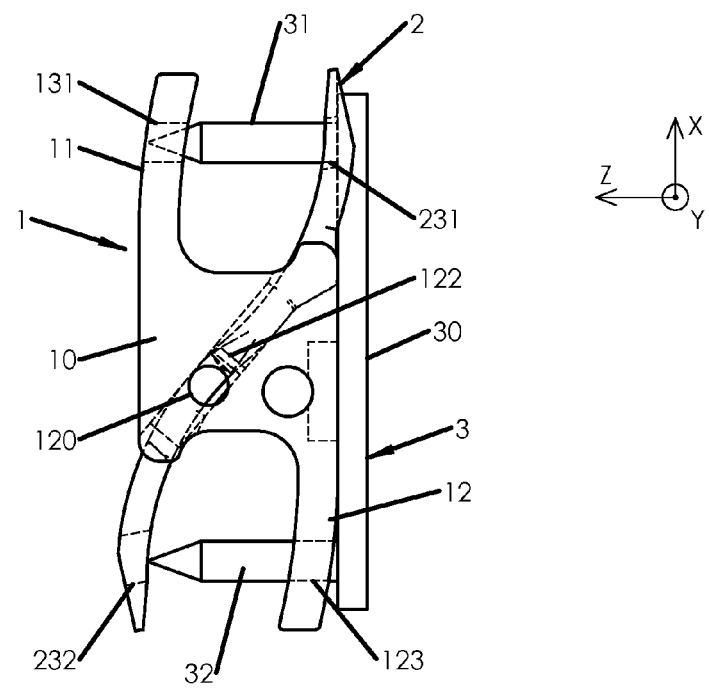
Figure 8C

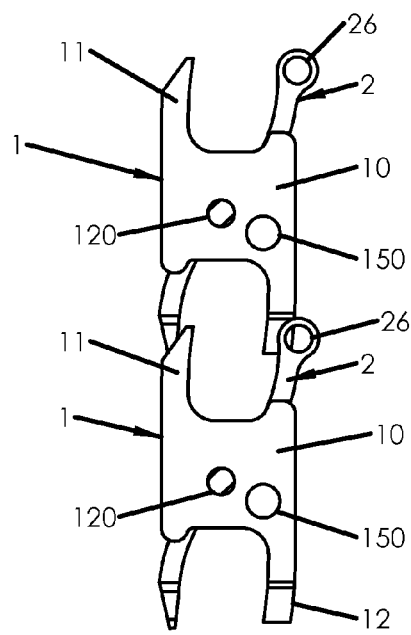
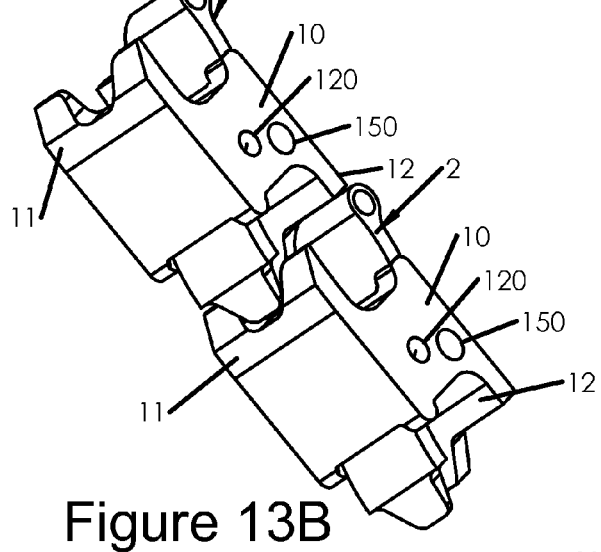
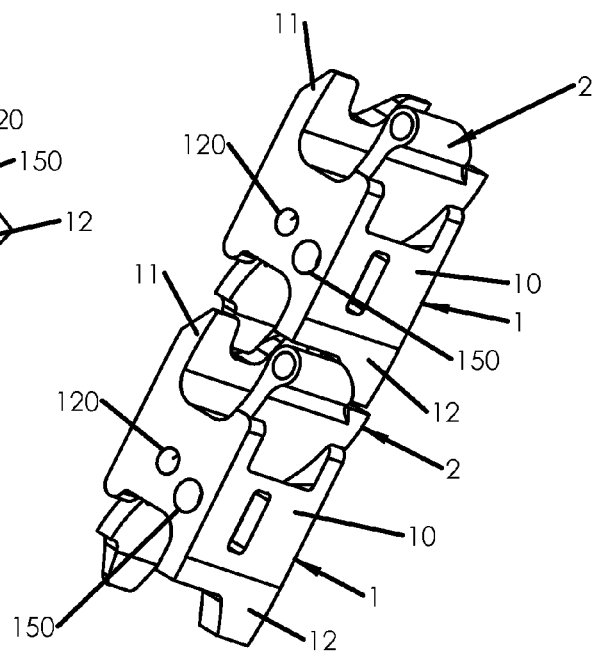
Figure 13A
Figure 13B
Figure 13C

Figure 16A
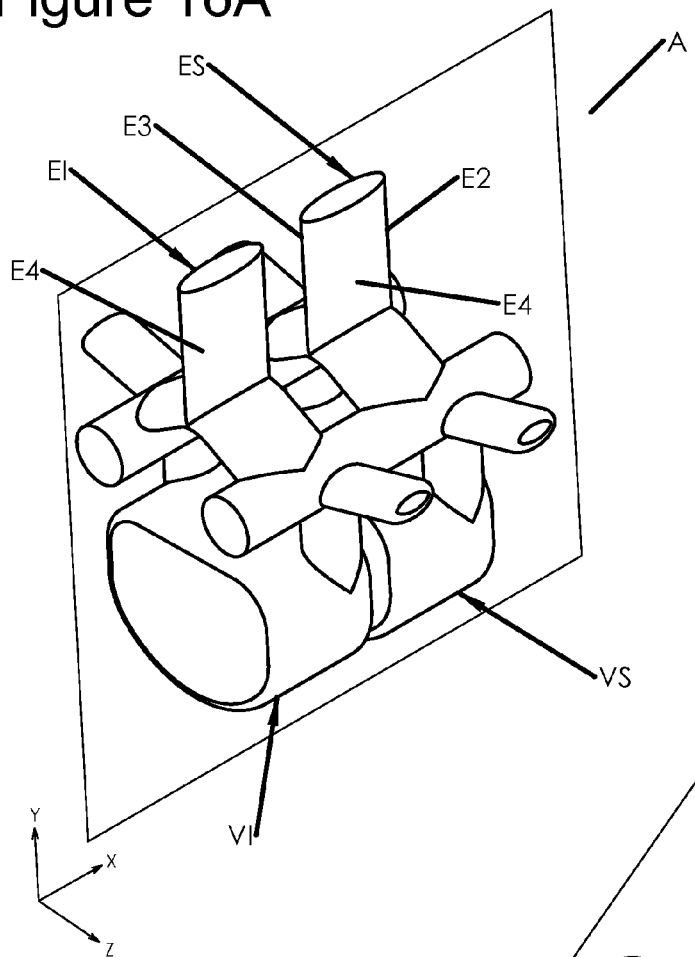
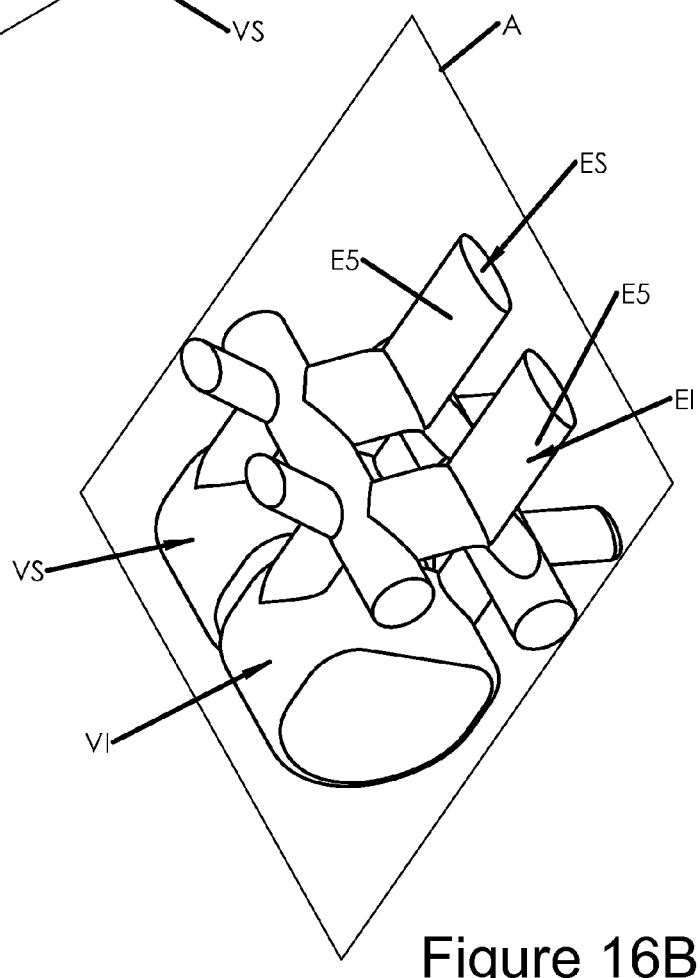
Figure 16B

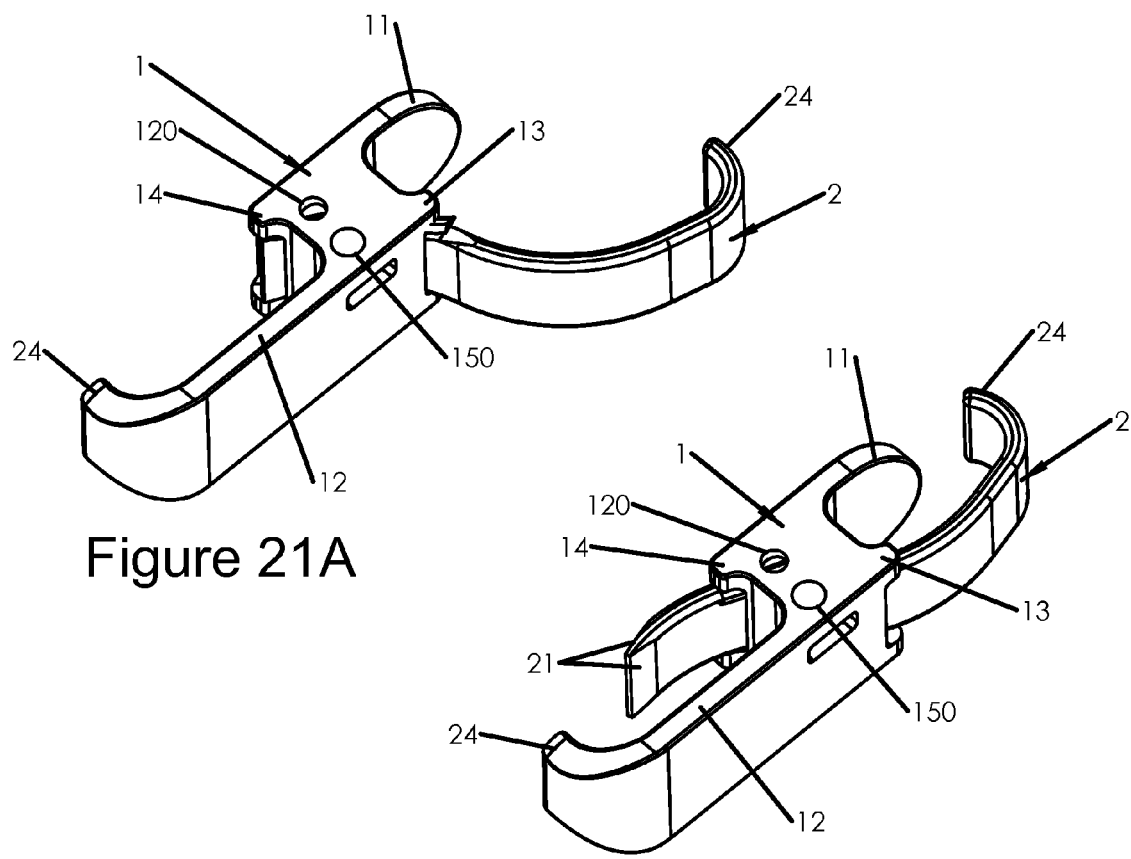
Figure 21A
Figure 21B
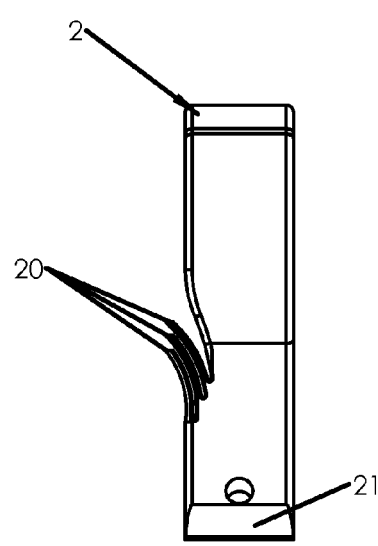
Figure 21C
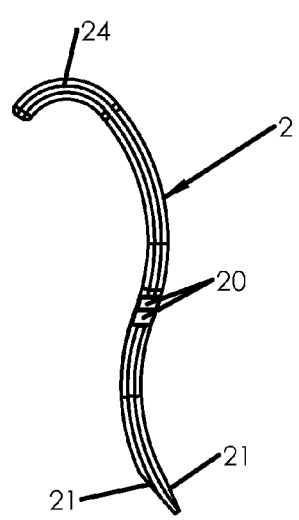
Figure 21D

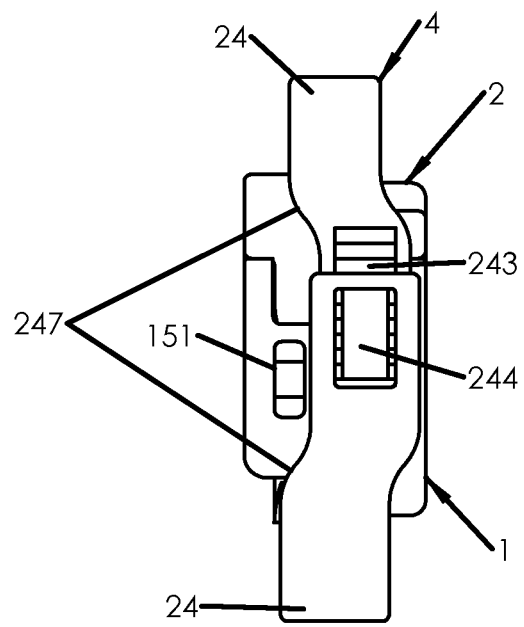
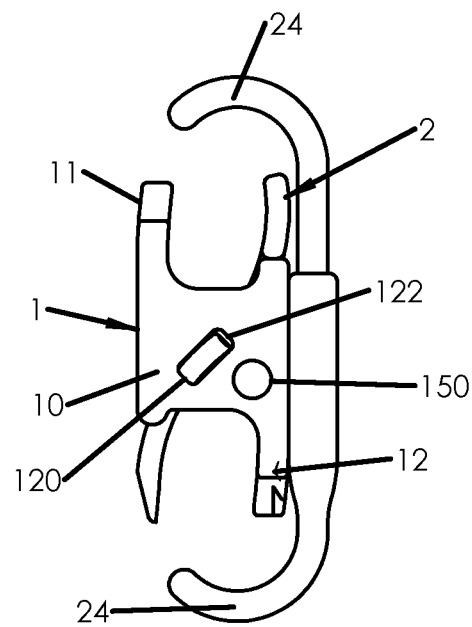
Figure 22A       Figure 22B
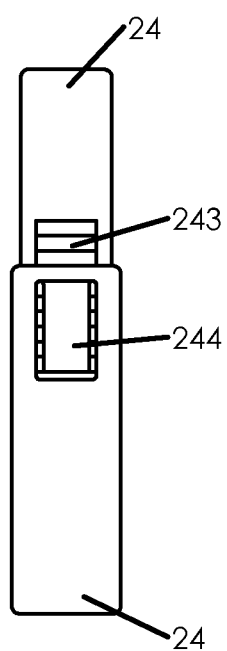
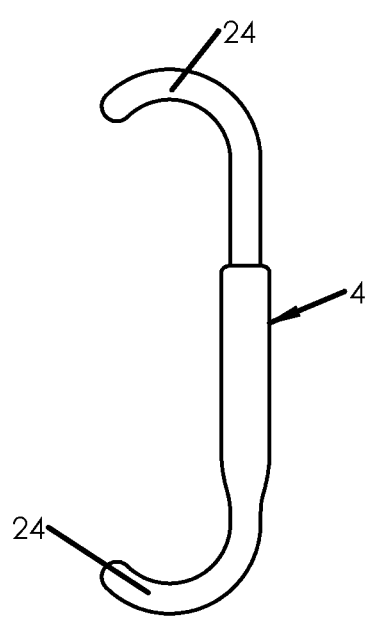
Figure 22C       Figure 22D

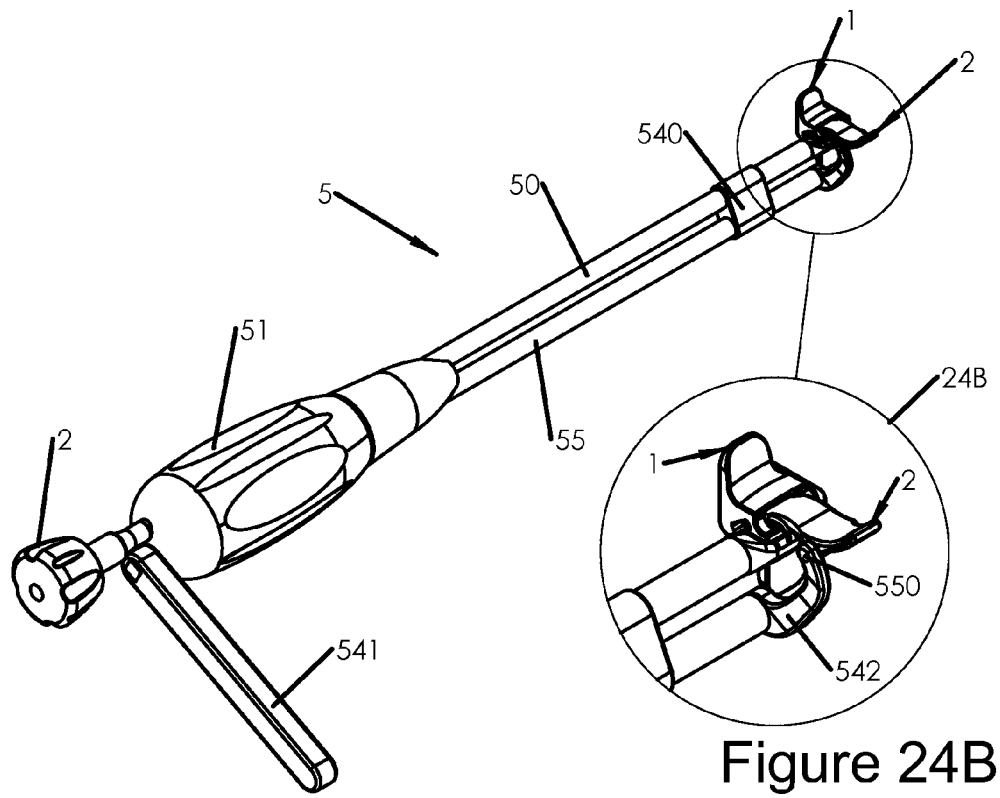
Figure 24A
Figure 24B
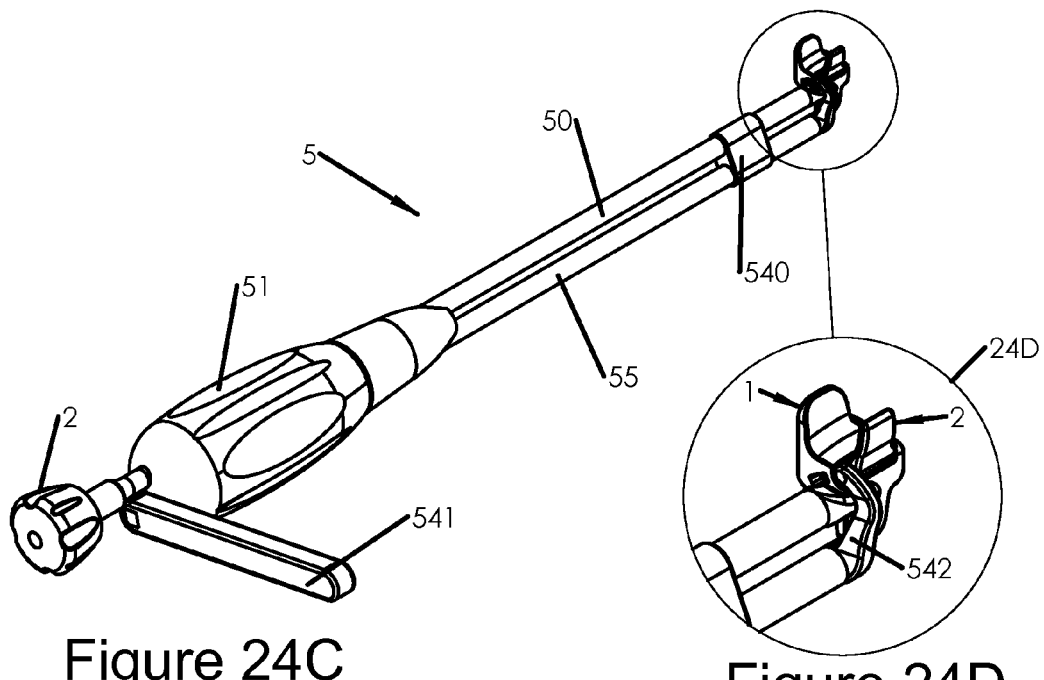
Figure 24C
Figure 24D

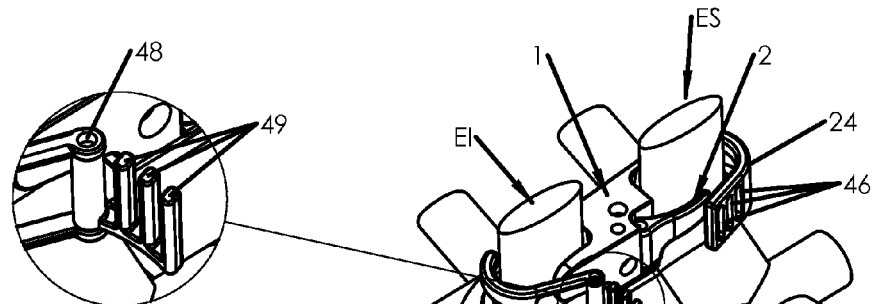
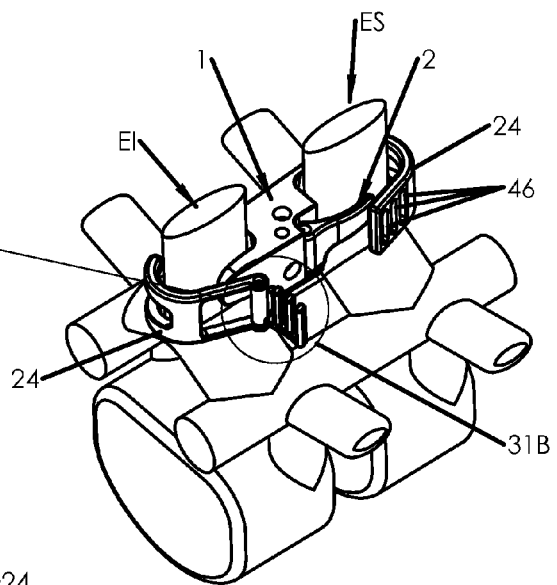
Figure 31B
Figure 31A
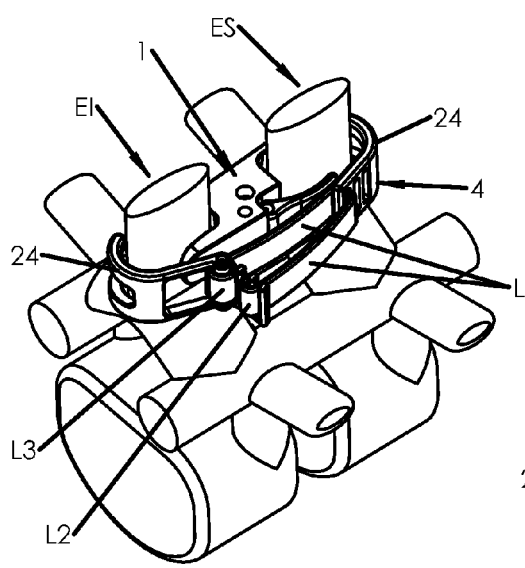
Figure 31C
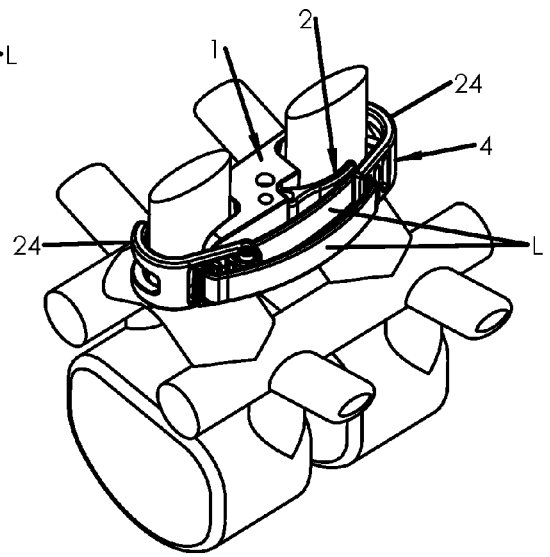
Figure 31D
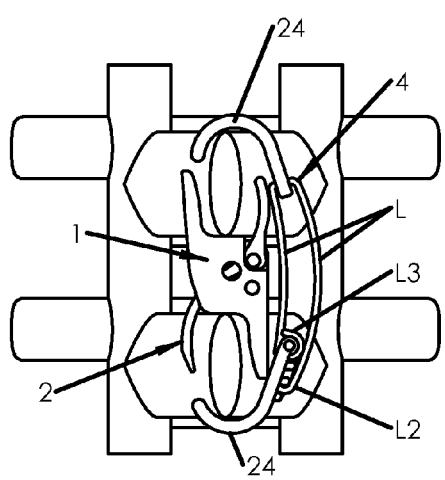
Figure 31E

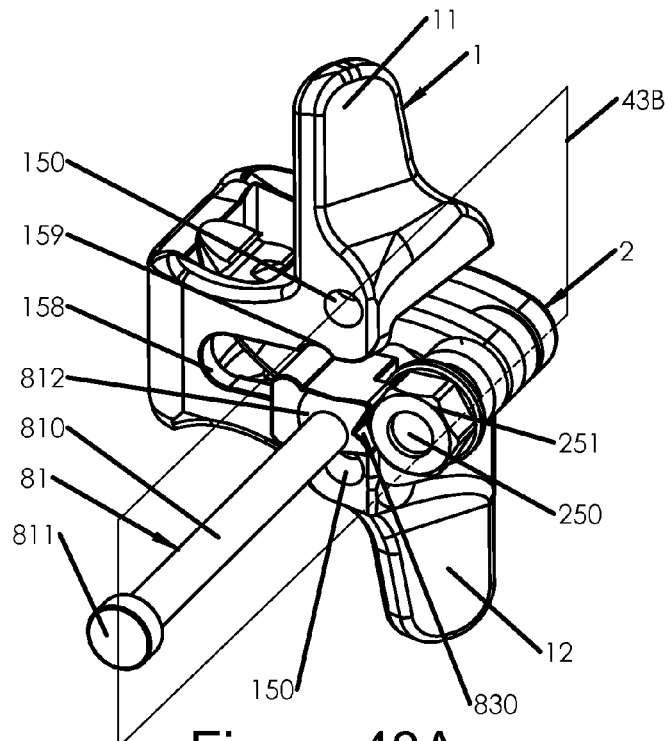
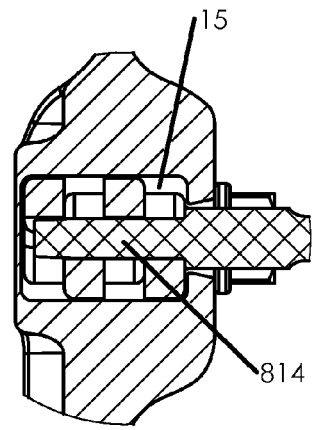
Figure 43A
Figure 43B
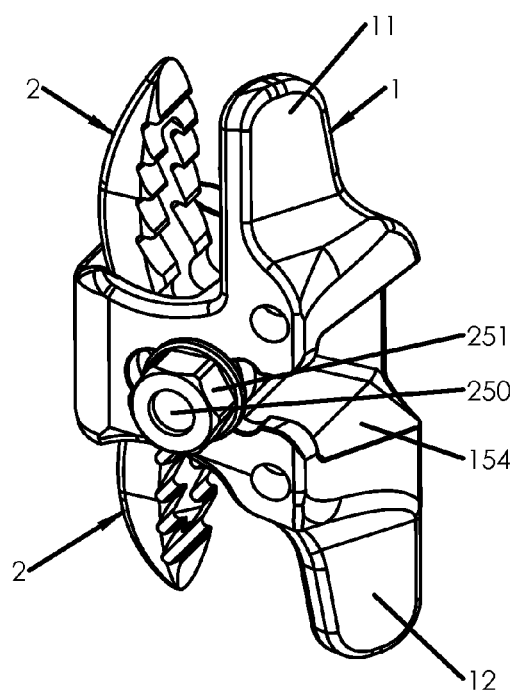
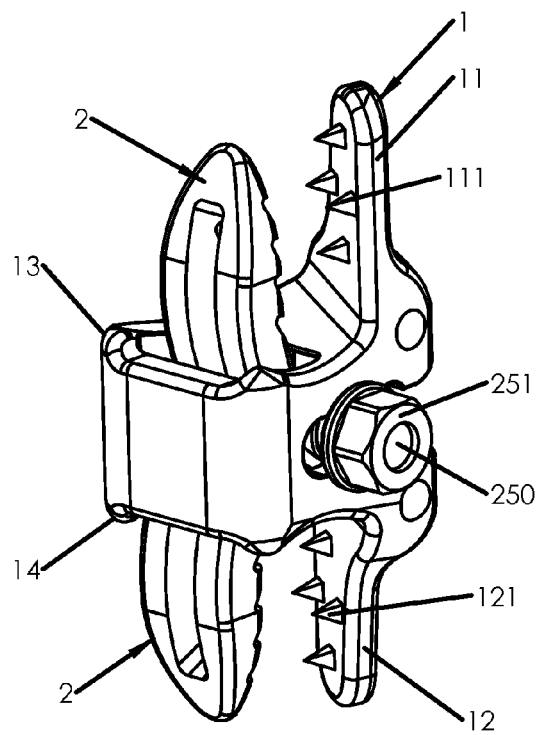
Figure 43C
Figure 43D

INTERSPINOUS IMPLANT AND INSTRUMENT FOR IMPLANTING AN INTERSPINOUS IMPLANT

CROSS-REFERENCE TO RELATED APPLICATIONS

This application is a continuation of U.S. patent application Ser. No. 13/369,650 filed Feb. 9, 2012, and issuing as U.S. Pat. No. 8,696,709 on Apr. 15, 2014, which claims priority under 35 U.S.C. §119 to French Patent Application No. 11/55908 filed in FRANCE on Jun. 30, 2011, and to French Patent Application No. 12/51031 filed in FRANCE on Feb. 3, 2012, all of which are incorporated by reference.

TECHNICAL FIELD

The present invention relates to the field of intervertebral prostheses, and in particular to the field of interspinous implants intended to be implanted between two adjacent spinous processes of two adjacent vertebrae. The present invention also relates to instruments for implanting such an implant.

BACKGROUND

The vertebrae of the vertebral column each have a spinous process, with the exception of the fused sacral and coccygeal vertebrae, where this spinous process is a more or less discernible vestige. These spinous processes have materially the shape of a plate oriented in the sagittal plane, with an upper edge, a lower edge, two lateral faces and a crest pointing rearward of the patient. The edges and faces can be more or less rounded depending on the patient, but make it possible to define surfaces on which an implant can bear. The interspinous space that separates two adjacent spinous processes has a variable size depending on the patient and on the location within the vertebral column. This space is generally filled by an interspinous ligament. In addition, the crests are covered by the supraspinous ligament that runs over the entire vertebral column. The spinous processes are therefore attached to one another by interspinous ligaments and the supraspinous ligament.

Interspinous implants are generally used particularly for pathologies such as herniated discs or degenerative lesions, hyperlordosis (particularly in the aged), shrinkage of the vertebral canal (lumbar stenosis) treated without laminectomy, persistent chronic lumbar pain, particularly in the event of failure of conservative treatment, degenerative disease of an intervertebral disc in a location adjacent to a prior fusion, spondylolisthesis of a grade lower than 1, etc. In certain cases, particularly the least severe pathologies, the interspinous implant provides an alternative or preliminary measure to more invasive measures. Thus, the implant may be used alone to maintain or restore the interspinous space to physiological values, particularly by preserving the mobility of the spinous processes in certain cases. In other cases, the interspinous implant can be used for vertebral fusion, particularly of the spinous processes but also in association with a disc fusion, for example.

Interspinous implants should make it possible to restore elevation between spinous processes and to maintain that elevation (to relieve articular facets, the nerve roots, the disc, etc.), particularly while awaiting arthrodesis (bone fusion). They must be stable between spinous processes, particularly in the lumbar region, whether or not having means available of anchoring to the spinous processes. In addition, it is desirable to have different implant heights and/or widths and/or depths available, particularly to match them best to their implantation sites. In addition it is preferred, in some cases, to immobilize the two spinous processes, while in other cases it is preferable to retain mobility. It is also sometimes desirable to control the extent of mobility, particularly bending and rotation motion of the vertebrae.

One problem relates to the stability of interspinous implants once implanted between two spinous processes. The implant must not become dislodged from its setting between the two spinous processes.

The stability of the interspinous implant is most often conferred by lateral wings, blades, arms or legs whose width makes it possible for them to spread over a relatively large area of the two adjacent spinous processes. The interspinous implants should, however, be able to lend themselves to multi-level surgery, and it is desirable that two implants be implantable in two adjacent interspinous spaces. The implant must therefore be stable between spinous processes, yet without having too great a bulk, so as to facilitate its implantation and/or allow its use in adjacent interspinous spaces.

Another problem relates to the invasiveness of the implantation. As it happens, it is generally preferable for the implant to be easily implantable and that it not be necessary to free too great a space in the interspinous space to be treated. It is also generally preferable to leave intact as many of the structures around the implantation site as possible. A compact implant, therefore, would be desirable.

Implants including at least one body insertable through the interspinous ligament are known from the prior art. Certain known implants necessitate, for their implantation, the total removal of the interspinous ligament located between the two spinous processes involved in the implantation, but sometimes also of at least a portion of the interspinous ligaments of the adjacent spinous processes. Certain implants also necessitate the removal of the supraspinous ligament, at least in the portion located over the two spinous processes involved in the implantation. These ligament removals are not desirable for the patient because they risk destabilizing the vertebral column and hence the implant, for example by increasing the risks of excessive motion of the spinous processes. Finally, these implants require the opening of too large an approach path for their insertion, usually by pushing away the surrounding tissues, which is not desirable for the patient for the same reasons as well as for reasons of muscle dilapidation.

Therefore, to obtain the least invasive implant possible, not requiring the opening of a large approach path, it is necessary to reduce the bulk of the implant and to limit the size of the implantation path. These constraints are attended by a problem of difficulty in implantation, especially if one wants to open only one (side) face of access to the spinous processes. In fact, for the least invasive possible implantation for example, an approach path passing only through a plane near the sagittal plane of the spinous processes might be desired, allowing impingement for instance only on one side of the patient's vertebral column, that is to say on only one lateral face of the spinous processes.

It will be noted that addressing the problem of invasiveness contributes additional constraints to the problem of stability, in particular because reducing the dimensions for reducing invasiveness may induce risks of stability. In this context, it is advantageous to offer a solution which allows invasiveness and stability to be reconciled.

SUMMARY

The present invention has as its object to mitigate certain disadvantages of the prior art by offering an interspinous implant which is less invasive, to allow simple insertion between two spinous processes, while still offering good stability between the spinous processes.

This goal is achieved by an interspinous implant, intended to be implanted between two adjacent dorsal spinous processes, each including an upper edge, a lower edge and two opposed lateral faces, wherein the implant includes at least one body with dimensions arranged so as to maintain or restore a distance between the adjacent edges of the two spinous processes and including at least two wings extending so that at least a part of each wing lies along at least a part of one lateral face of one of the two spinous processes and, additionally, at least one retainer for the implant, designed to retain the body of the implant between the two spinous processes and to be inserted from the same lateral face as the body.

The assembly of the interspinous implant in two distinct pieces, particularly with a retainer added to the body of the implant, allows the implant to be implanted in a very non-invasive manner by a unilateral posterior approach, without dis-inserting the supraspinous ligament, and passing through the interspinous ligament while minimizing damage thereto, the implant being able to spread itself sufficiently around the interspinous space to allow the stable installation thereof.

In addition, in certain embodiments, the implant can be easily withdrawn.

According to another feature, at least a portion of the retainer projects to the lateral faces of the body opposite to those comprising the wings, once the implant is assembled with the retainer.

According to another feature, the retainer includes an insert and in that the implant comprises at least one passage passing through at least one part of the body and having a shape, dimensions and orientation arranged for insertion, through the body, of at least one insert including at least one curved plate retained within the body so that at least a part of the said curved plate lies along at least a part of one lateral face opposite the at least one lateral face along which one wing lies.

According to another feature, the insert is attached to the body by a retention mechanism.

According to another feature, the body includes two wings arranged on the same lateral face of the implant so as to lie along the same lateral faces of the two spinous processes, two passages being arranged in the body for the insertion of two inserts each projecting toward one of the spinous processes so as to lie along the same, opposite lateral face the passages being accessible for insertion of the inserts on the same lateral face as the wings so that the implantation between the spinous processes can be carried out from only one of the lateral faces thereof.

According to another feature, the body includes two wings arranged on the same first lateral face of the implant so as to lie along the same lateral faces of the two spinous processes and a third wing located on a second lateral face opposite the first so as to lie along the opposite lateral face of a first of the two spinous processes, a passage being provided in the body for insertion of an insert extending toward the second spinous process to lie along the same lateral face thereof as the third wing, the passage being accessible for insertion of the insert on the lateral face equipped with the two wings so that the implantation between the spinous processes can be carried out from a single one of the lateral faces thereof.

According to another feature, the body includes, on the side opposite that provided with the two wings, at least one chamfer facilitating the insertion of the body between the adjacent edges of the two spinous processes.

According to another feature, the body includes two wings each arranged on one lateral face of the implant opposite the other wing and each extending toward one of the two spinous processes, so that the wings each lie along one spinous process, but on opposite lateral faces, the insert being of substantially sigmoidal shape due to its plate including at least two radii of curvature of opposite orientations, so that both faces of the plate include both a concave and a convex part, the passage and the insert being arranged in such a way that, when the insert is lodged in the passage, at least one portion of the said convex parts of the two faces of the insert each lies along at least one part of the spinous processes, on the lateral faces opposite those which the wings lie along.

According to another feature, the wings are provided on the lateral faces of the implant and the body includes upper and lower faces in contact with adjacent edges (E2, E3) of the two spinous processes, the body including, on at least one of these upper and lower faces, near the lateral faces not having wings, at least one ridge preventing the implant from disengaging from the space between the adjacent edges of the two spinous processes.

According to another feature, said ridge is chamfered toward at least one lateral face of the implant to facilitate the insertion of the body between the adjacent edges of the two spinous processes.

According to another feature, the retention mechanism includes at least one stop for the insert coming, when the insert is lodged in the through passage, into contact with at least one surface of the body near the through passage and at least one flexible tab of the insert oriented substantially in the direction of the said stop and arranged, firstly, to fold away during the insertion of the insert into the through passage and secondly to unfold and to bear on a surface provided for this purpose on the body.

According to another feature, said surface provided for the flexible tab is accessible from outside the body by a duct, so as to allow disengagement of the flexible tab and withdrawal of the insert.

According to another feature, the stop and its abutment surface on the body are so arranged that the stop does not project beyond the perimeter of the body.

According to another feature, at least one wing of the implant includes at least one point arranged so as to anchor itself in the lateral face of the spinous process along which said wing lies.

According to another feature, the sigmoidal insert includes, on at least one of its convex parts, at least one point arranged so as to anchor itself in the lateral face of the spinous process along which said convex portion lies.

According to another feature, at least one of the wings and/or at least one insert includes at least one hole arranged to receive at least one pin of at least one bone anchorage device.

According to another feature, the sigmoidal insert includes, at one of its ends, and indentation separating the curved plate into two branches and including a bearing surface designed to receive a transverse bar of a bone anchorage device including two pines perpendicular to said bar, the anchorage device being so arranged that, firstly, one of the pins enters the hole in one wing of the implant while the other pin passes between the branches of the insert and so that, secondly, said bar bears on the bearing surface of the indentation in the insert and causes the insert to enter the through passage of the implant when the pins penetrate a lateral surface of the spinous processes.

According to another feature, said retainer comprises a complementary body, superimposable on the body so that two wings of the complementary body extending from the complementary body are each arranged on a lateral face opposite to that of a wing of the implant's body, locking resources being arranged to maintain the two bodies superimposed by fixing their position with respect to the other, so that the wings of each body maintain the orientation of the other body compared to the two spinous processes.

According to another feature, the complementary body has dimensions designed to maintain the distance between the adjacent edges of the two spinous processes complements the body of the implant.

According to another feature, the wings of each of the two bodies extend, on their face parallel to the sagittal plane, as far as the lateral face of the other body.

According to another feature, the two bodies are mounted so as to pivot relative to one another about a rotation pivot designed to as to allow one portion of each of the wings of the complementary body to be placed in contact with a portion of a wing of the first body, to facilitate the insertion of the implant between the spinous processes, and to then allow deployment of the wings of the complementary body parallel to the sagittal planel, the locking means being designed to lock the wings of the complementary body in the deployed position.

According to another feature, the two wings of the body extend, on their lateral face, to the lateral face of the complementary body and a single wing of the complementary body extends, on its lateral face, to the lateral face of the body, while the other wing of the complementary body does not extend substantially farther than the rest of the body, so as to facilitate the insertion of the complementary body onto the body when the later is already in place between the spinous processes.

According to another feature, the retainer of the implant includes at least one flexible connector one end of which is affixed to a first of the two wings and which is located within the body so as to run over each lateral face of the two spinous processes opposite to that along which each wing lies.

According to another feature, the body has a passage for the flexible connector from one lateral face to the other between the two spinous processes.

According to another feature, the body has a locking means designed to lock the connector relative to the implant.

According to another feature, the passage running through the body from one lateral face to the other follows an oblique path, orienting the flexible connector toward the portion of each lateral face not having a wing.

According to another feature, the body includes upper and lower faces in contact with the adjacent edges of the two spinous processes, at least one of said lower and upper faces being provided with at least one cushioning material.

According to another feature, the body includes upper and lower faces in contact with the adjacent edges of the two spinous processes, and includes a material favoring bone growth to allow the fusion of the upper and lower spinous processes at least at the location of said lower and upper faces.

According to another feature, at least one of the wings and/or at least one insert is(are) provided with shapes and/or dimension designed so that two implants can be implanted in two consecutive interspinous spaces of three adjacent vertebrae without having the wings or the inserts overlap, even partially.

According to another feature, the retainer comprises at least one spinous hooking resources arranged to hook around at least a portion of an edge of a dorsal spinous process that is opposite to the edge against which the body of the implant is affixed.

According to another feature, the hooking resources comprise at least one hooking device distinct from the implant and including at least two parts each comprising, on the one hand, a curved portion forming a sort of hook for hooking opposite edges of adjacent dorsal spinous processes and, on the other hand, an attachment structure of both parts for maintaining the spacing between these parts.

According to another feature, the attachment structure is adjustable, for adjusting the spacing between the two parts of the hooking device, so as to control the spacing of the hook-shaped portions and therefore the spacing of the spinous processes.

According to another feature, the hooking device comprises linking or connection resources to the implant and/or the insert.

According to another feature, the attachment structure of the hooking device has at least one ligament connecting the two parts together According to another feature, the retainer comprises at least a portion of the insert forming a sort of hook arranged to hook, at the introduction of the insert in the passage of the body, around a spinous process, on at least a portion of the edge which is opposite the edge against which the body of the implant is affixed.

According to another feature, the hooking resources comprise at least one hook pivotally mounted on the body of the implant and arranged to hook around a spinous process, on at least a portion of the edge which is opposite the edge against which the body of the implant is affixed.

According to another feature, the hooking resources comprise at least one end portion of a wing of implant forming a sort of hook arranged to hook around a spinous process, on at least a portion of the edge which is opposite the edge against which the body of the implant is affixed.

According to another feature, the implant comprises compression resources for compressing the lateral faces of at least one spinous process between at least one wing of the implant and a retainer of the implant.

The present invention also relates to an instrument facilitating the implantation of an interspinous implant which is poorly invasive.

This aim is attained by an instrument for implanting an interspinous implant defined according to the invention, wherein it includes at least one means for gripping the implant which includes at least one anchorage to receive the said gripping means and at least one actuating means, movable with respect to the gripping means and arranged so as to drive the insert into the implant when it is actuated.

BRIEF DESCRIPTIONS OF VARIOUS VIEWS OF THE DRAWINGS

Other features and advantages of the present invention will appear more clearly upon reading the following description, given with reference to the appended drawings, in which:

FIGS. 8A and 8B shows perspective views of an interspinous implant in the free and locked condition, respectively, according to certain embodiments, FIG. 8C showing a top transparency view of the locked configuration implant in FIG. 8B;

FIGS. 10A, 10B and 100 show perspective views of an interspinous implant and a sigmoidal insert according to certain embodiments;

FIGS. 13A through 13C show a top view and two perspective views from opposite sides, respectively, of a series of two interspinous implants according to certain embodiments;

FIGS. 16A and 16B show perspective views oriented to the opposite lateral faces of two adjacent vertebrae in the vertebral column, illustrating the spinous processes, the sagittal plane of the vertebral column and a three-dimensional benchmark used as a reference;

Figures 17A, 17B, 17C:
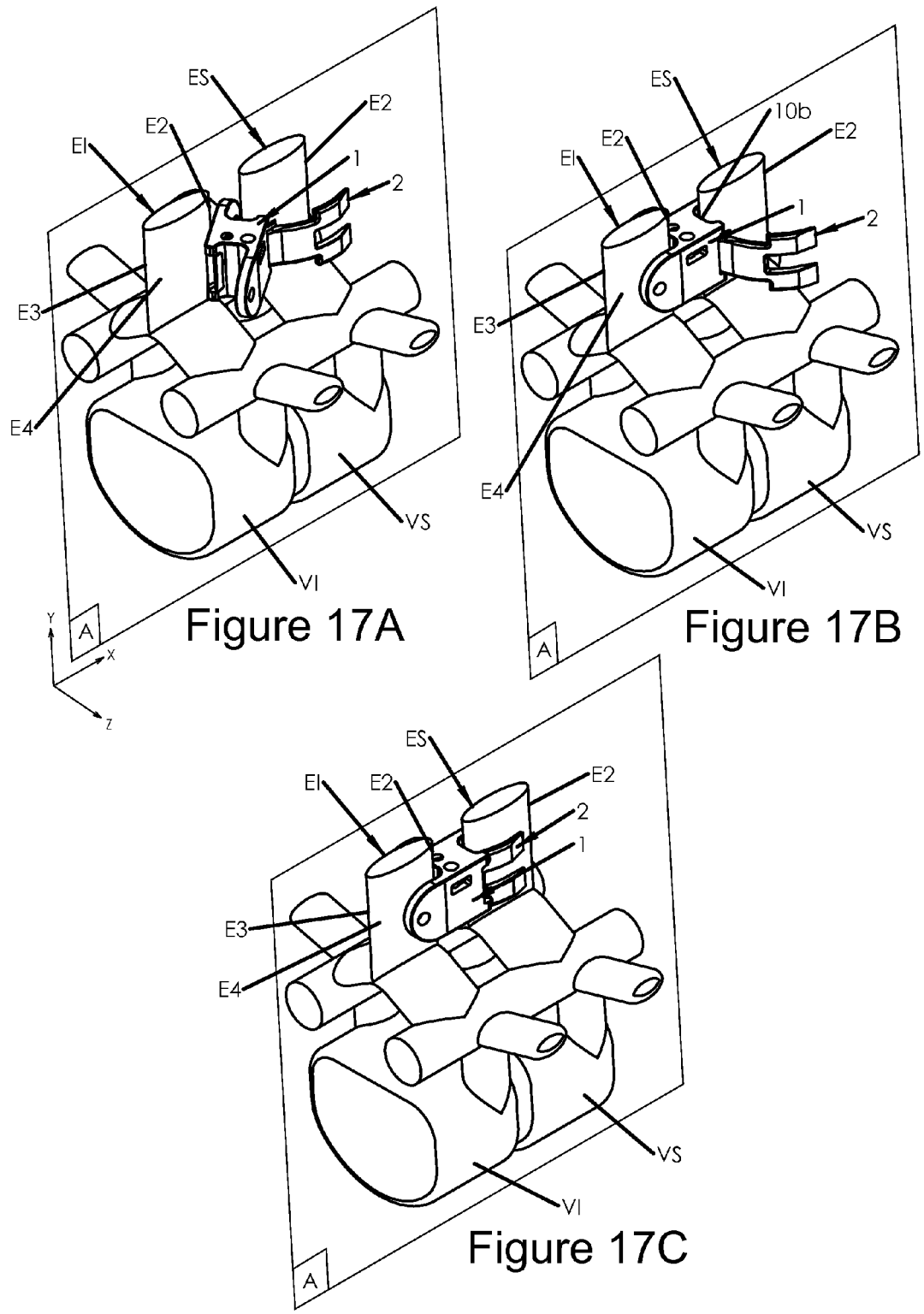
Figure 18A:
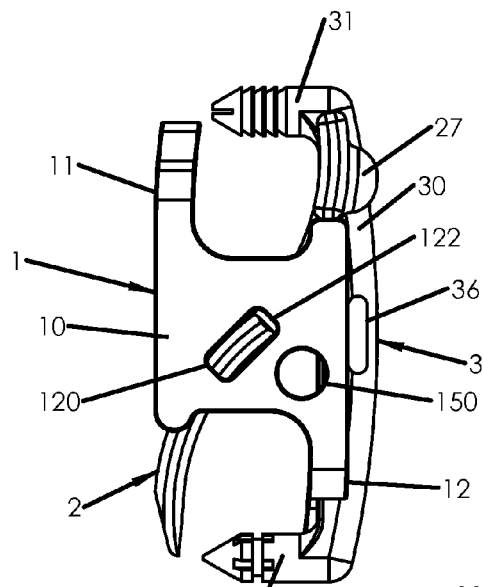
Figure 18B:
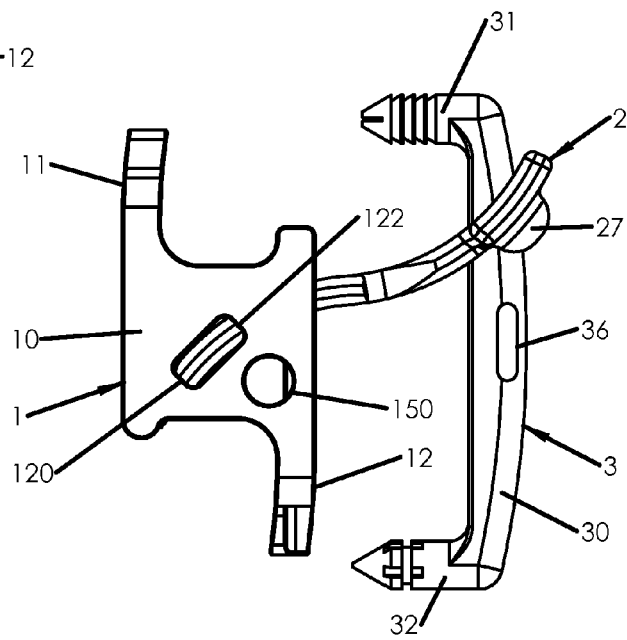
Figure 18C:
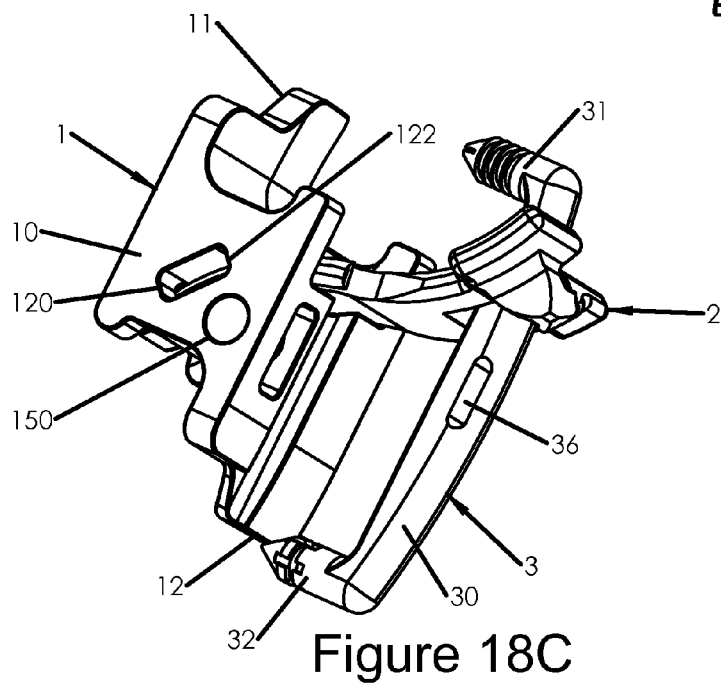
Figure 19A:
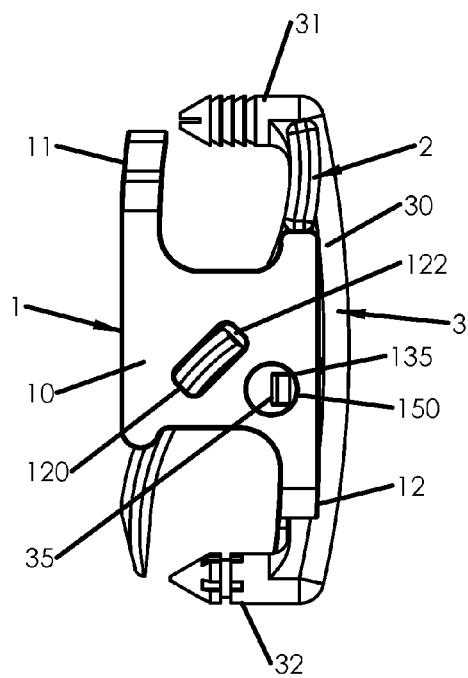
Figure 19B:
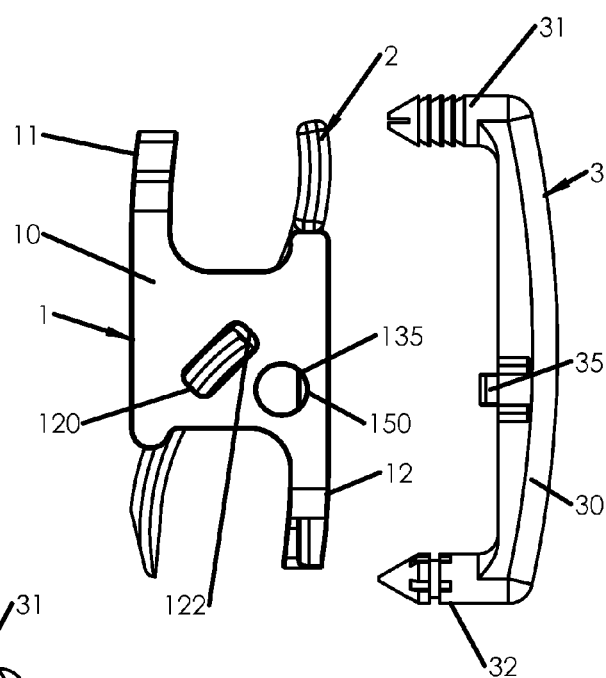
Figure 19C:
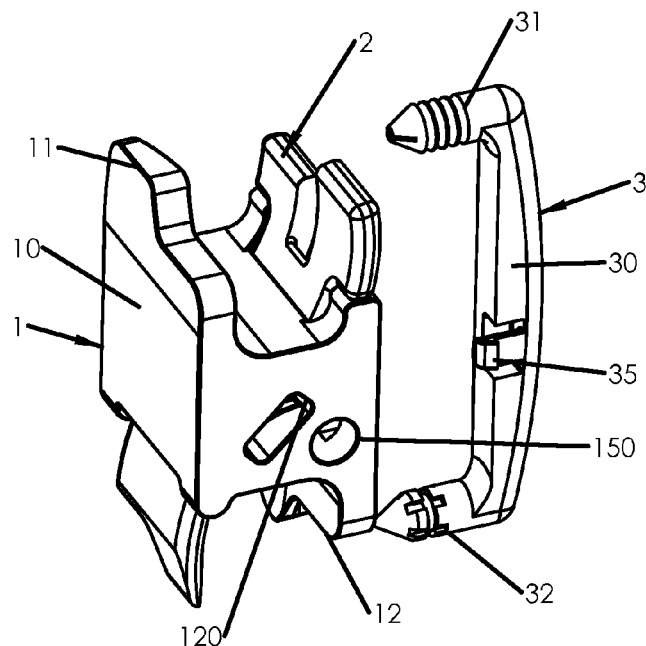
Figure 20A:
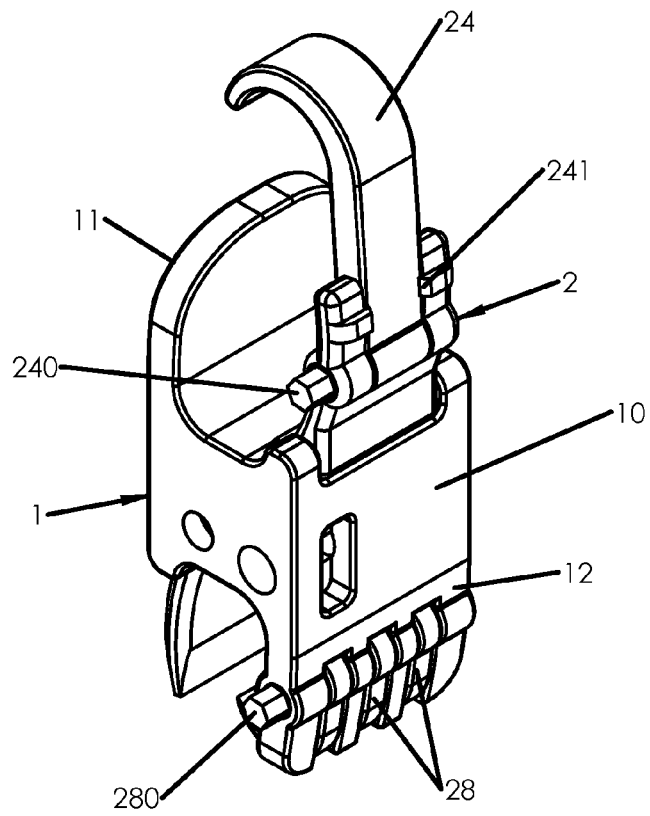
Figure 20B:
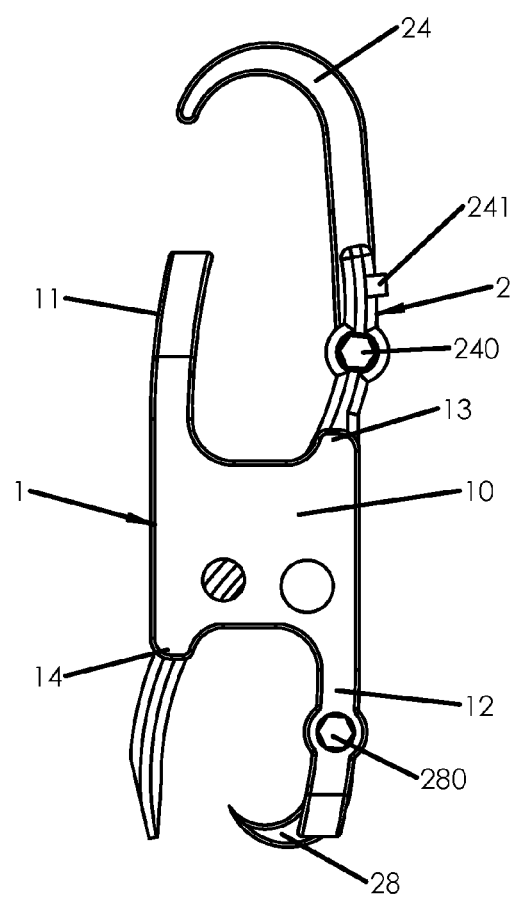
Figure 23A:
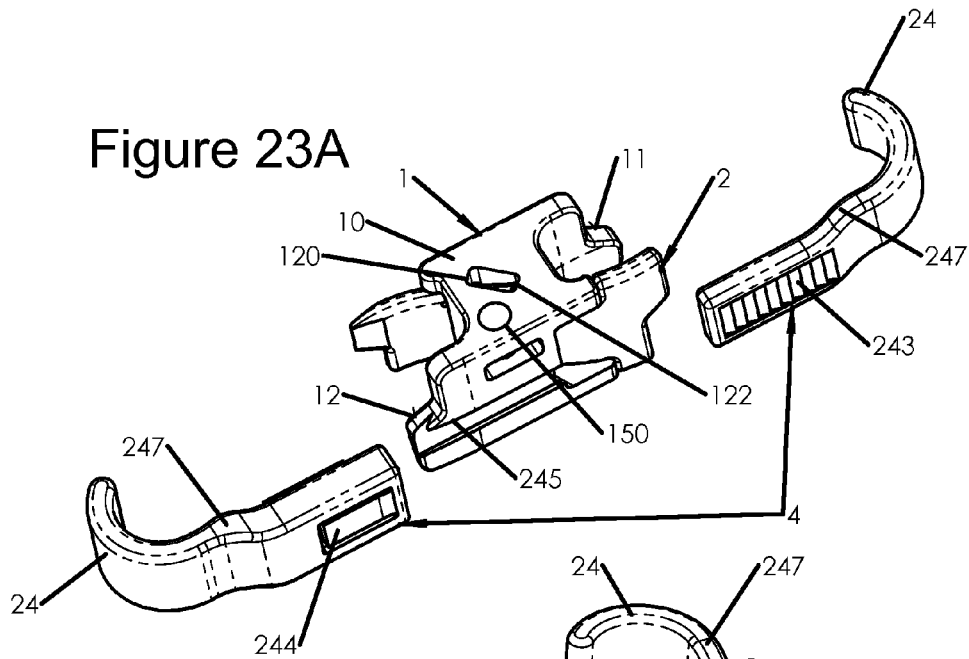
Figure 23B:
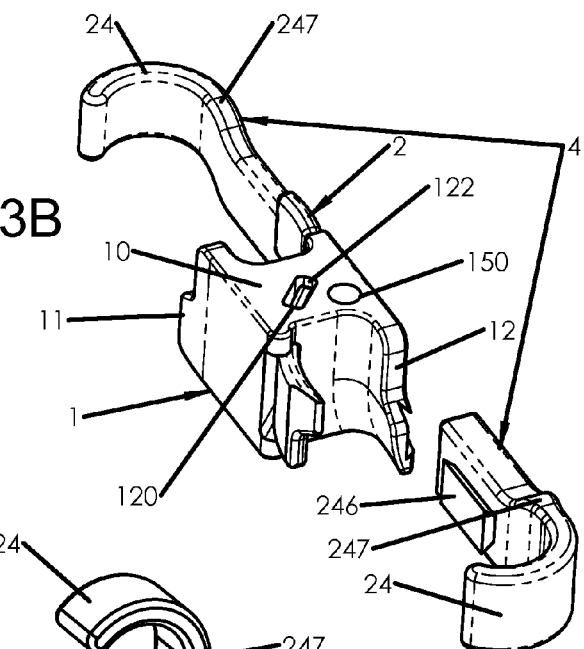
Figure 23C:
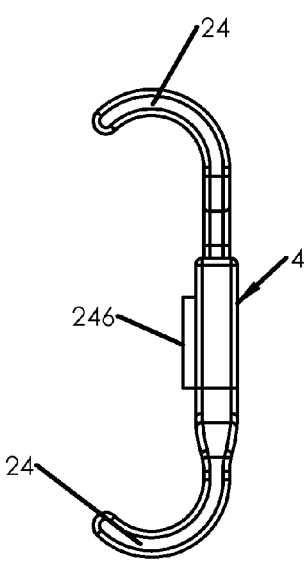
Figure 23D:
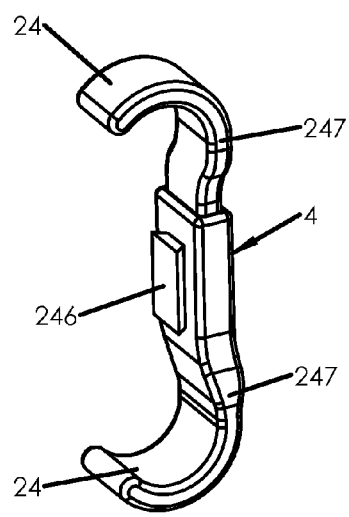
Figure 25A:
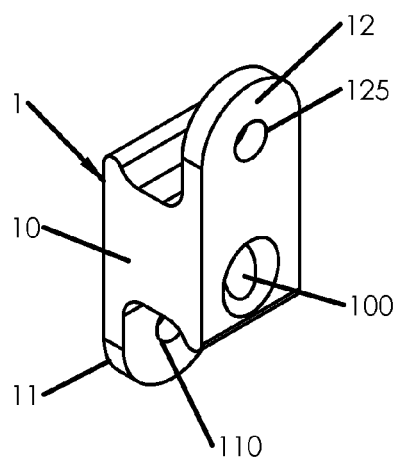
Figure 25B:
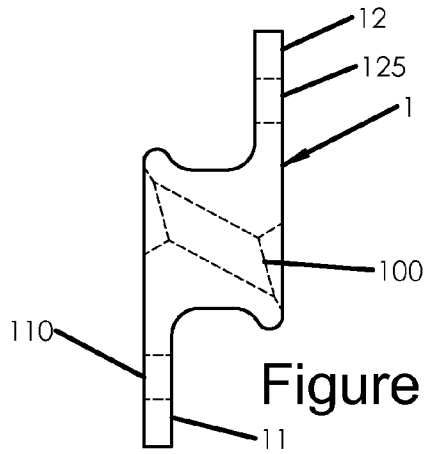
Figure 25C:
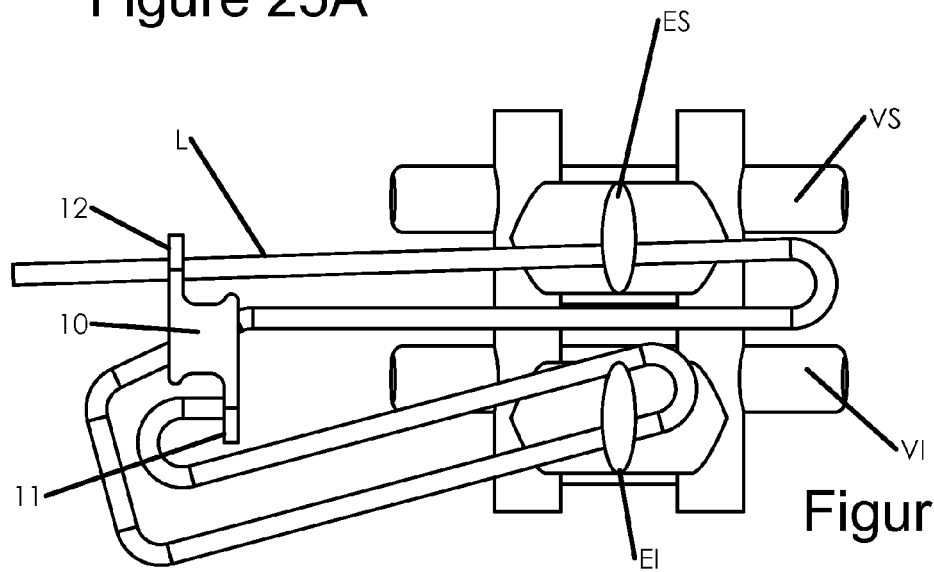
Figure 25D:
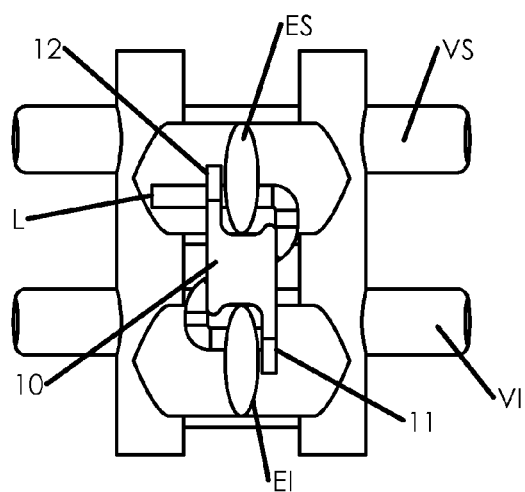
Figure 26A:
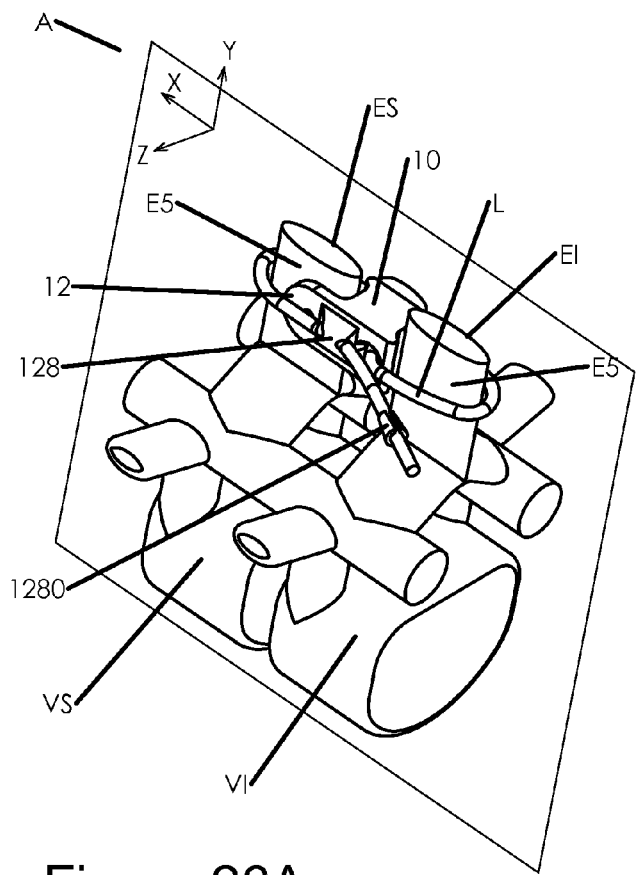
Figure 26B:
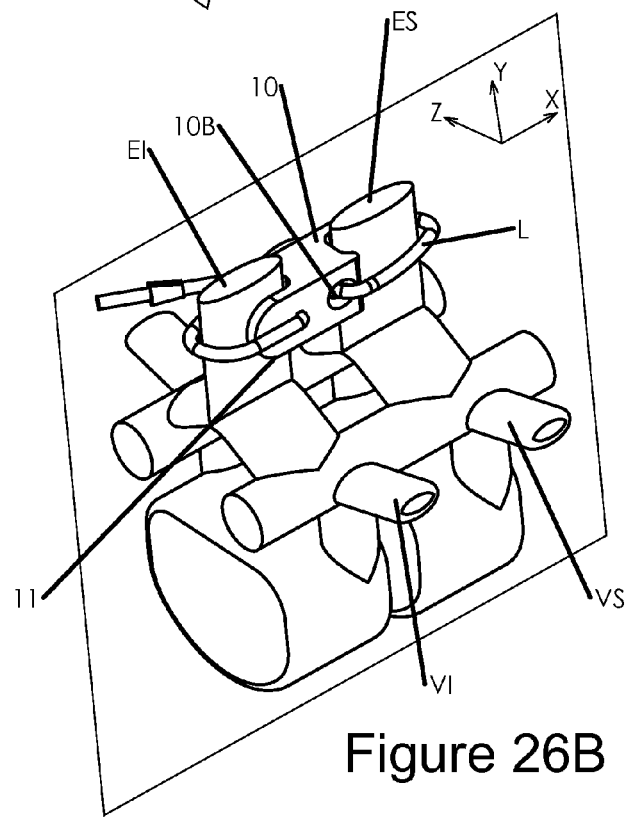
Figure 27A:
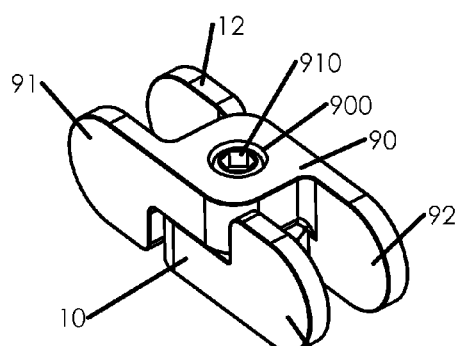
Figure 27B:
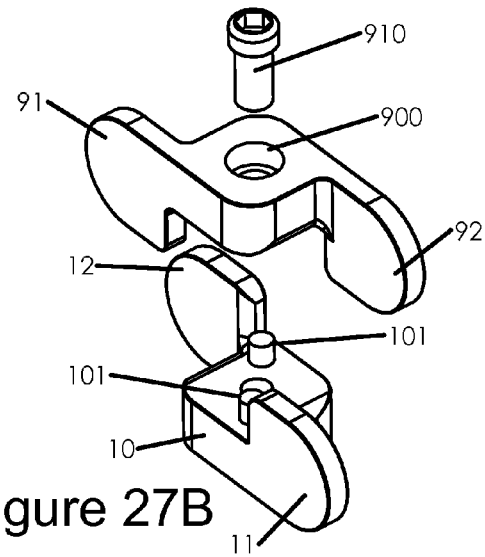
Figure 27C:
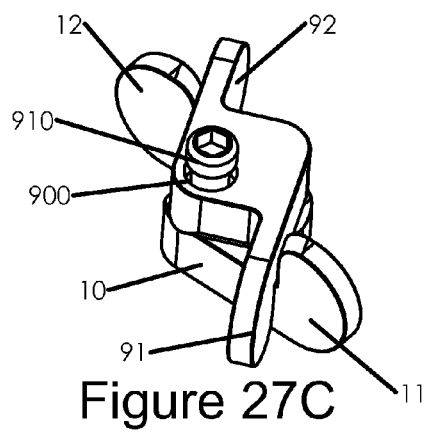
Figure 27D:
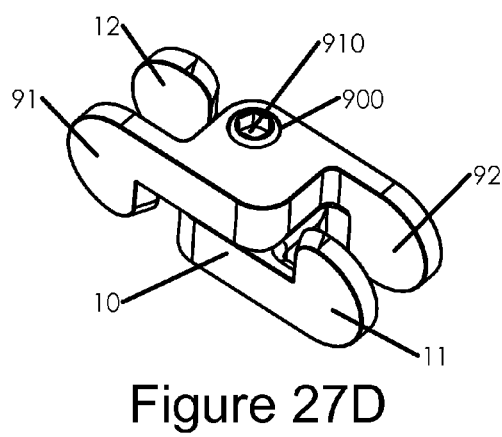
Figure 27E:
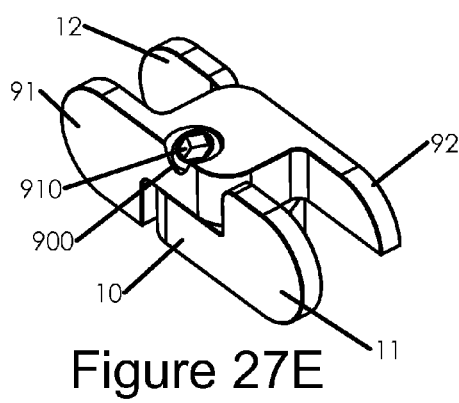
Figure 27F:
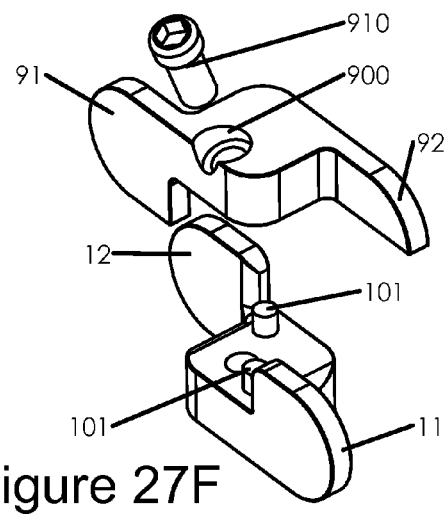
Figure 28A:
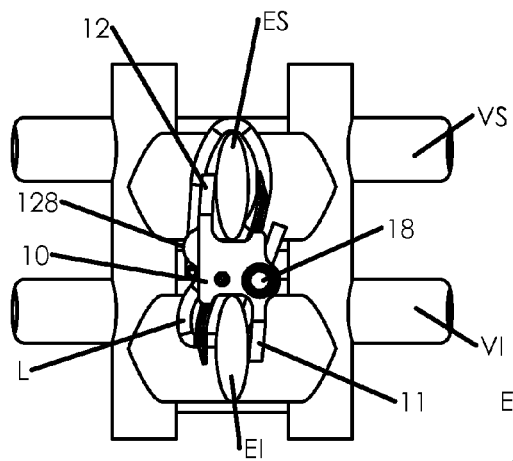
Figure 28B:
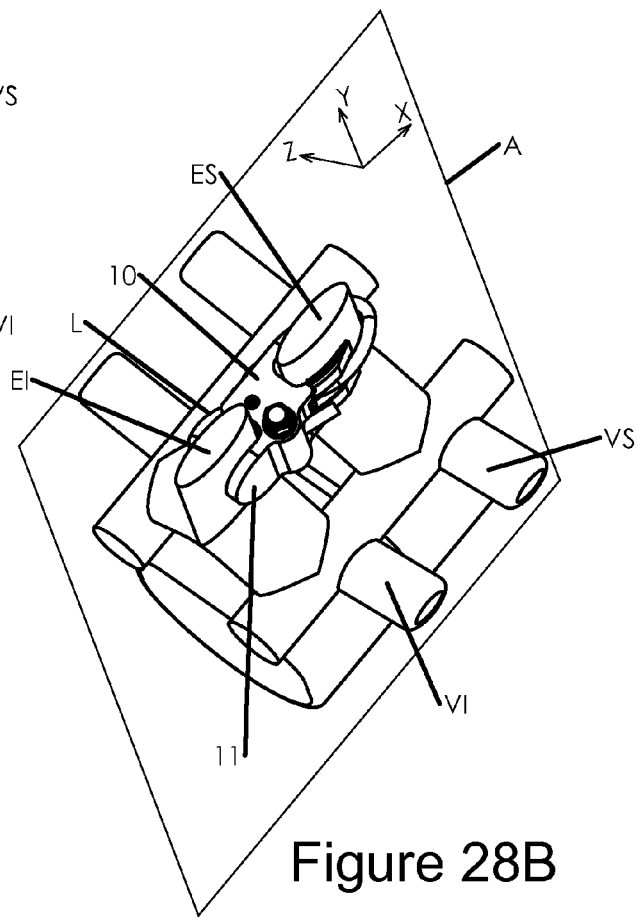
Figure 28C:
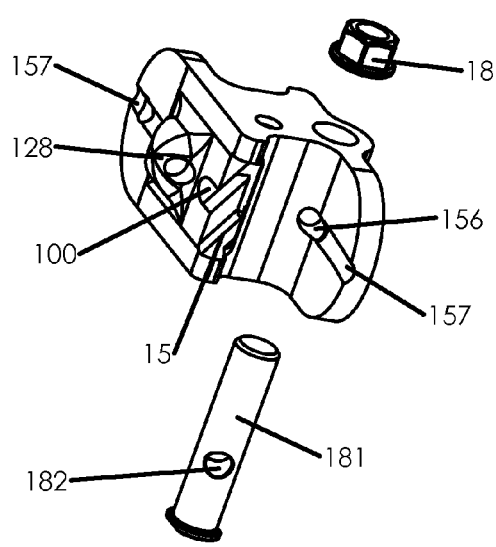
Figure 28D:
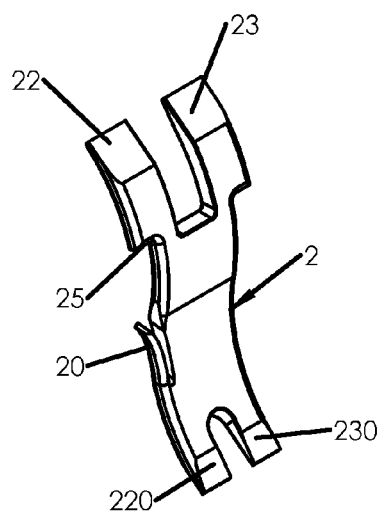
Figure 29A:
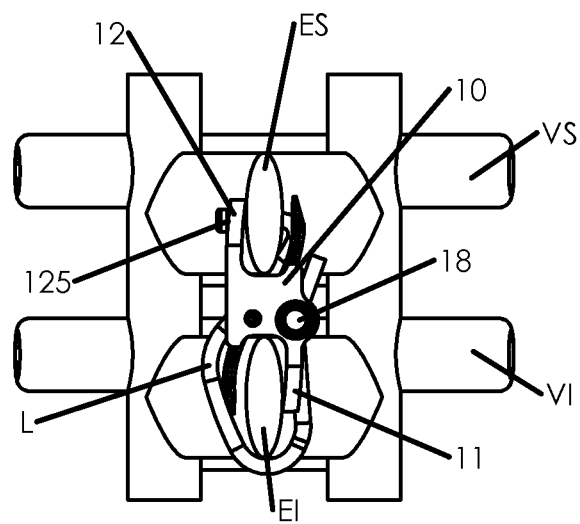
Figure 29B:
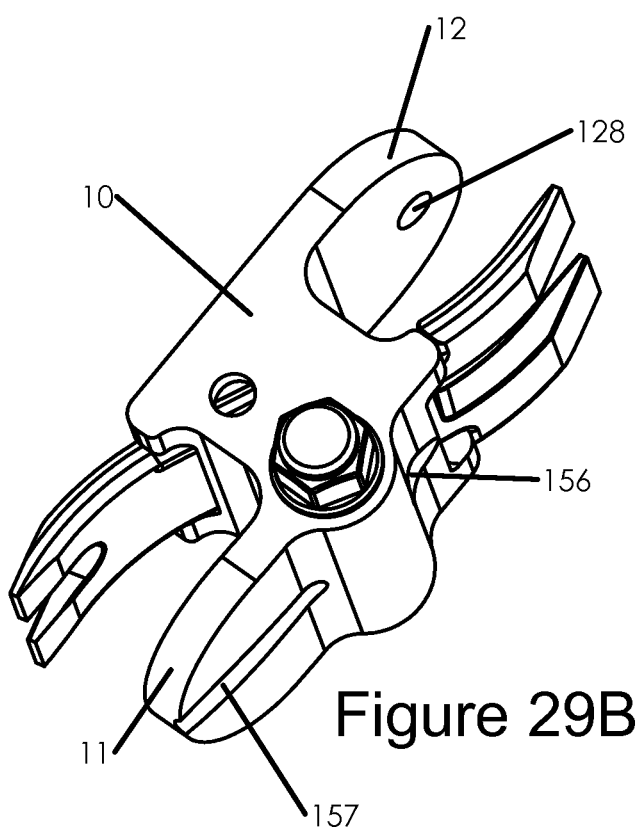
Figure 30A:
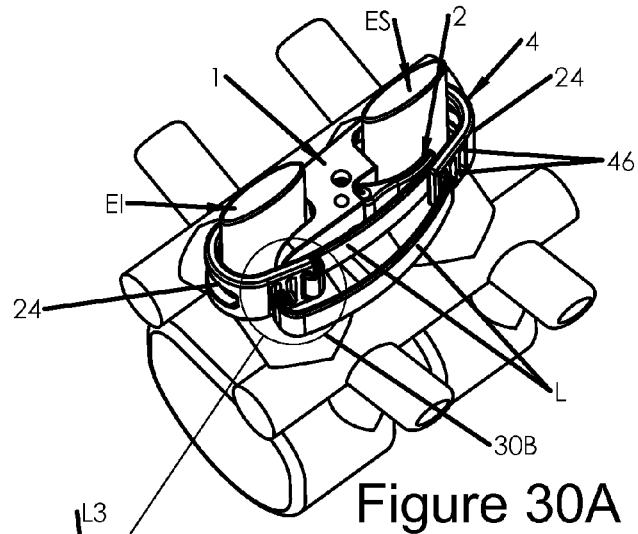
Figure 30B:
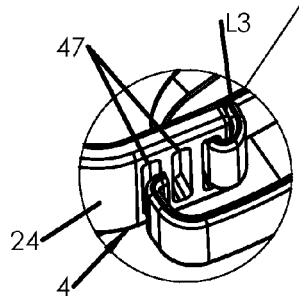
Figure 30C:
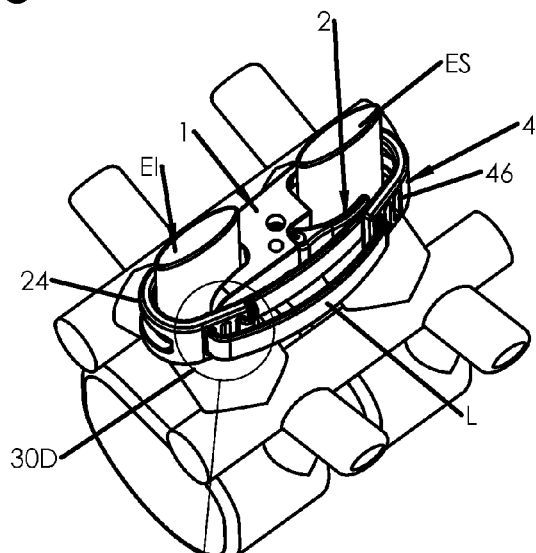
Figure 30D:
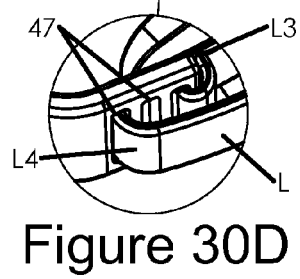
Figure 30E:
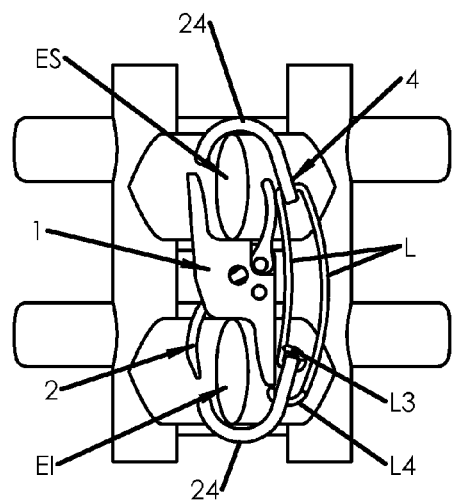
Figure 32A:
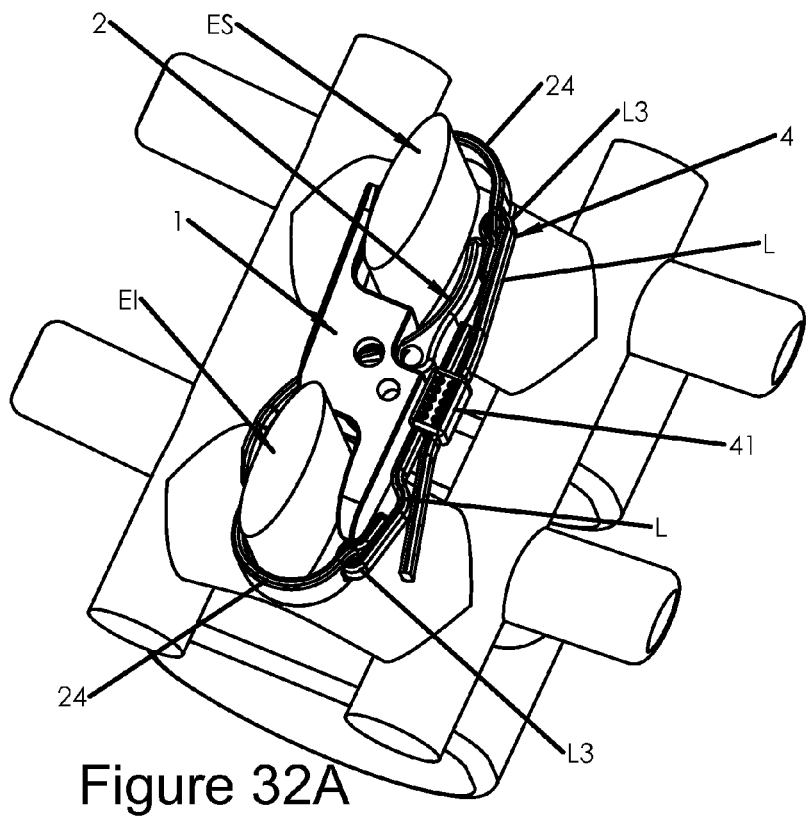
Figure 32B:
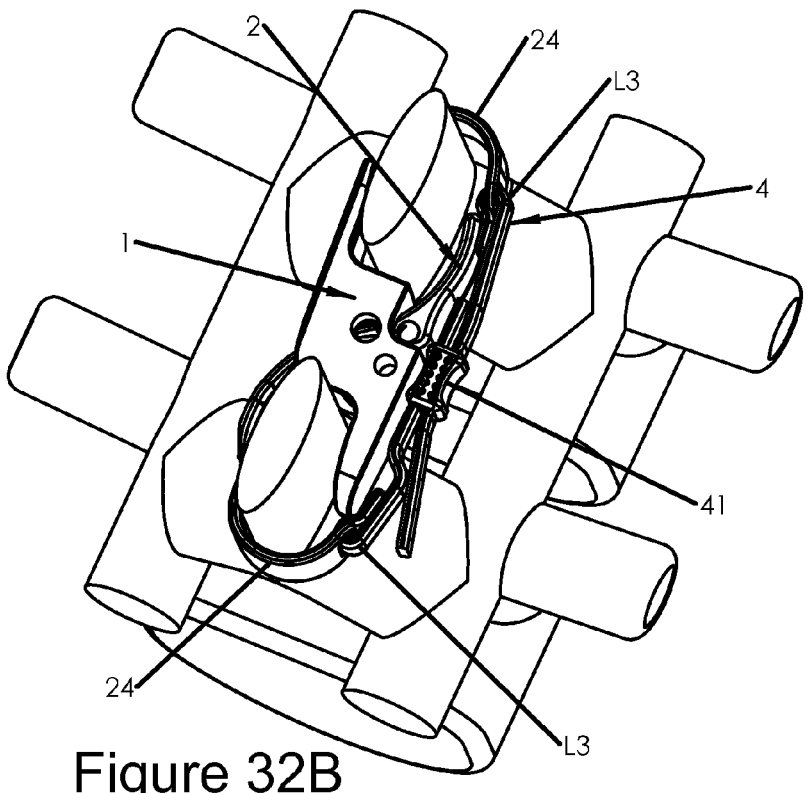
Figure 33A:
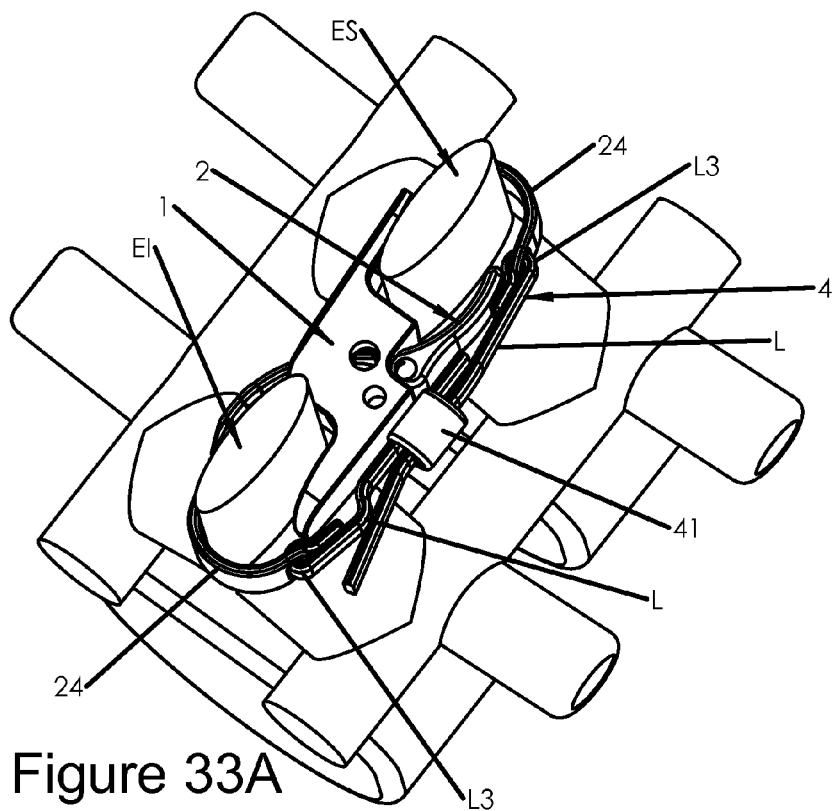
Figure 33B:
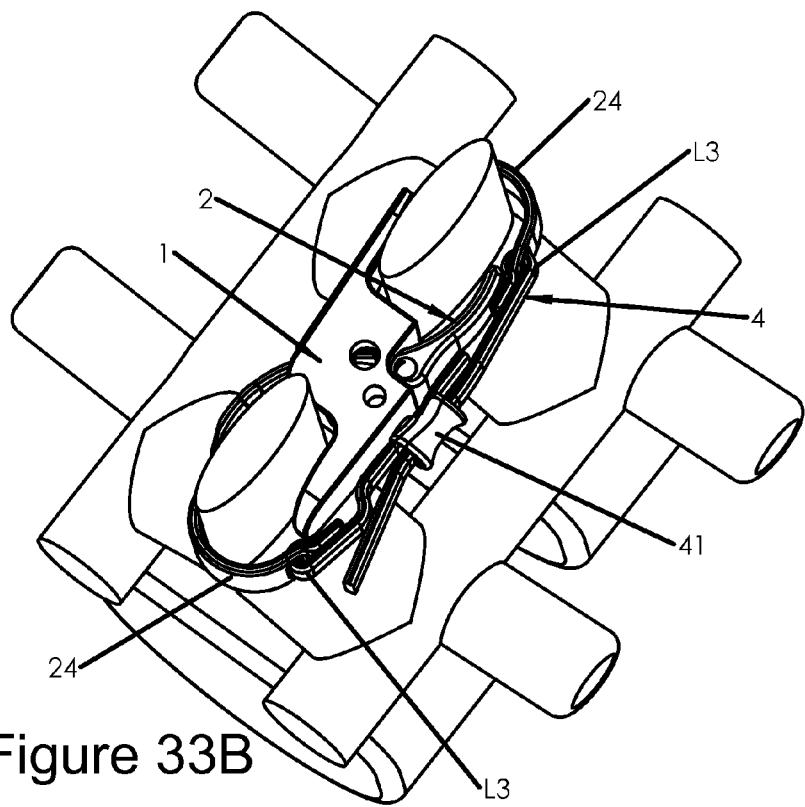
Figure 34A:
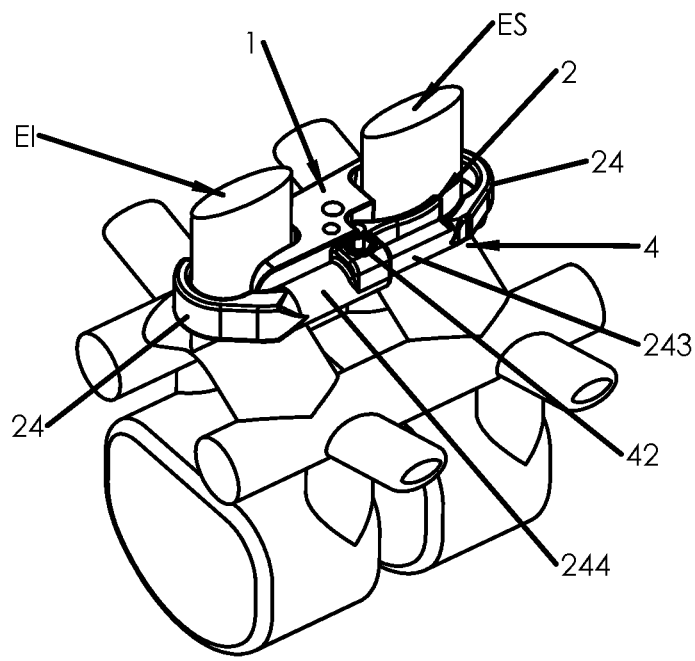
Figure 34B:
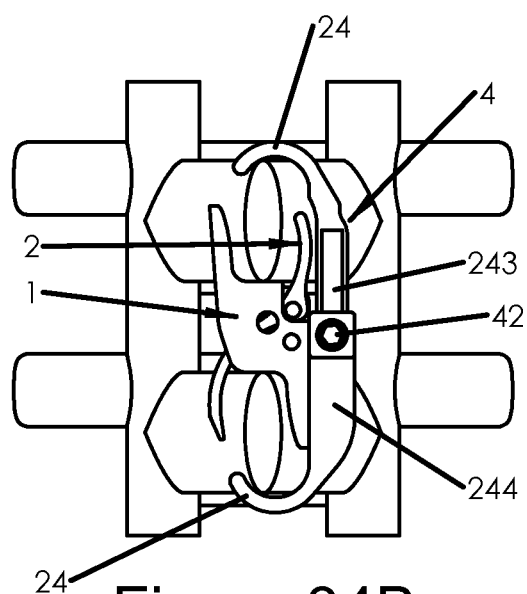
Figure 35A:
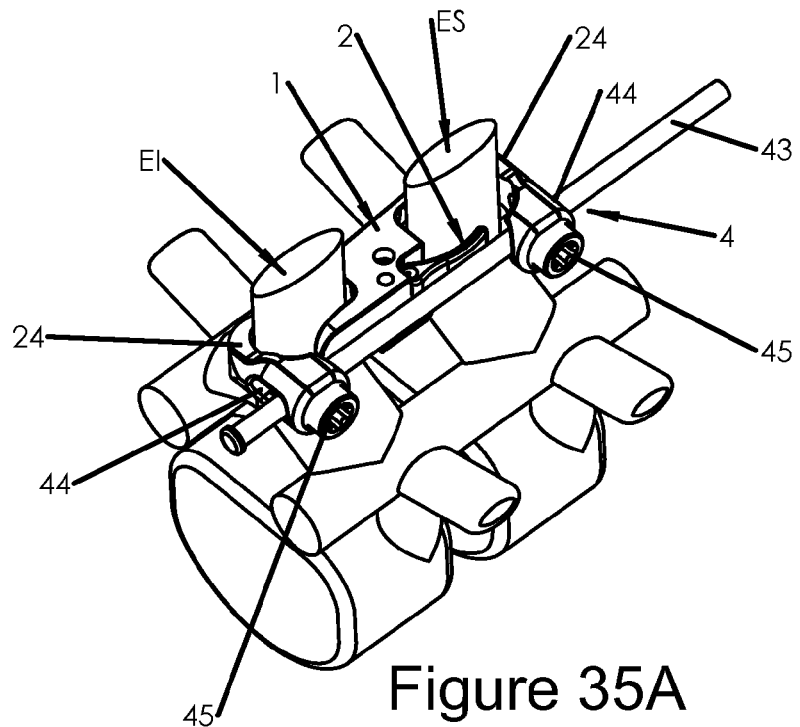
Figure 35B:
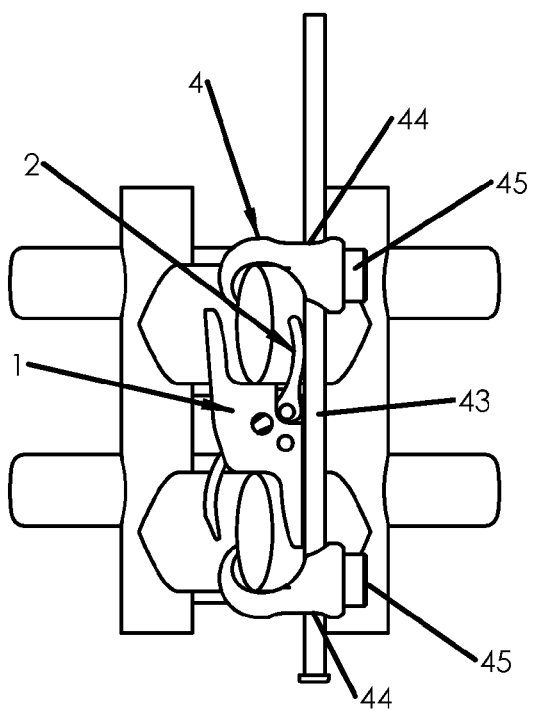
Figure 36A:
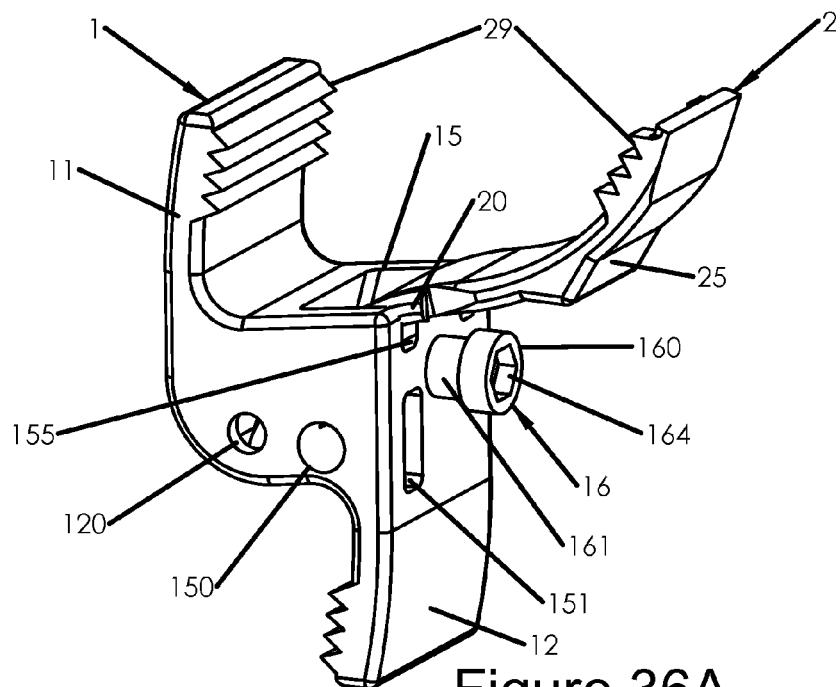
Figure 36B:
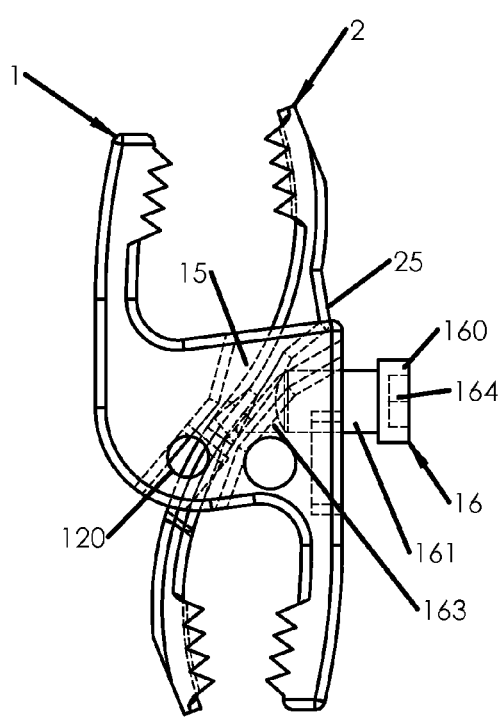
Figure 36C:
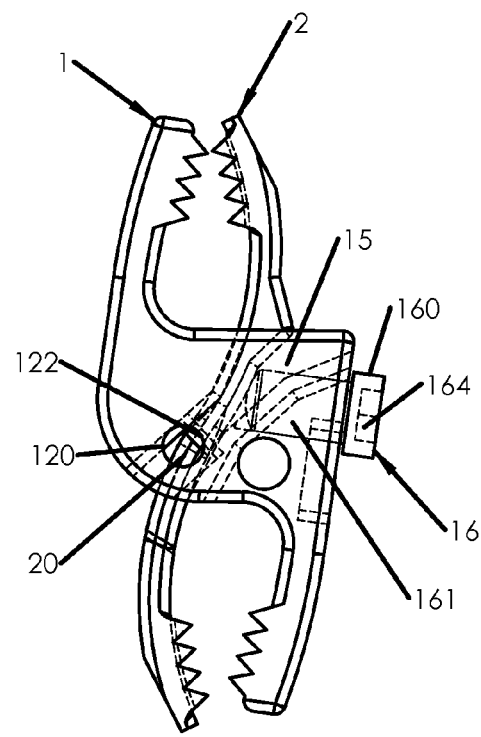
Figure 37A:
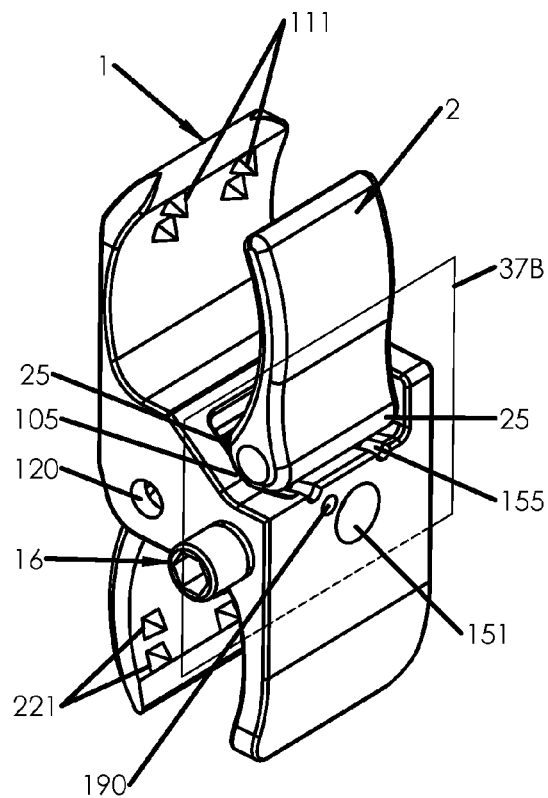
Figure 37B:
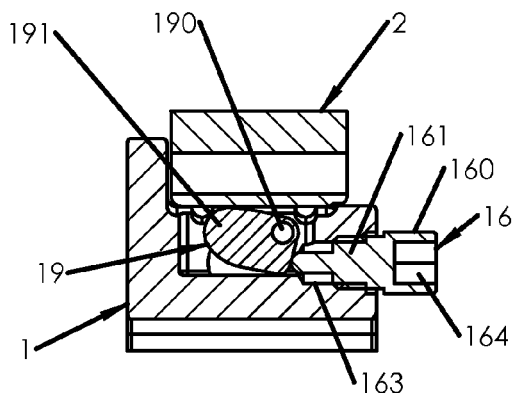
Figure 37C:
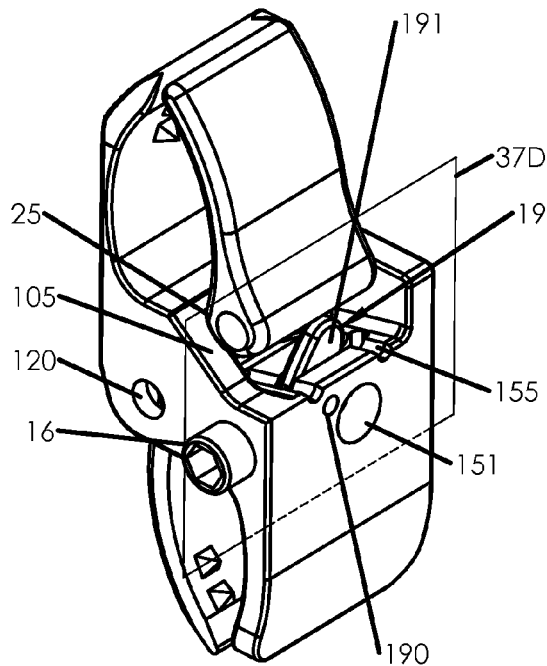
Figure 37D:
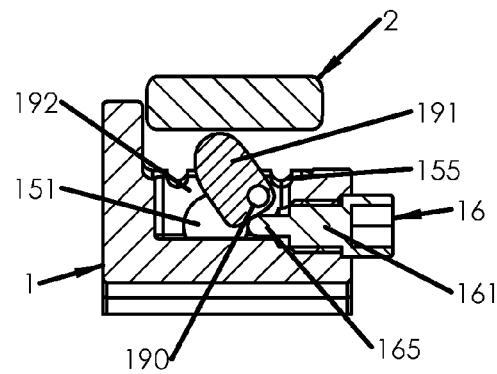
Figure 38A:
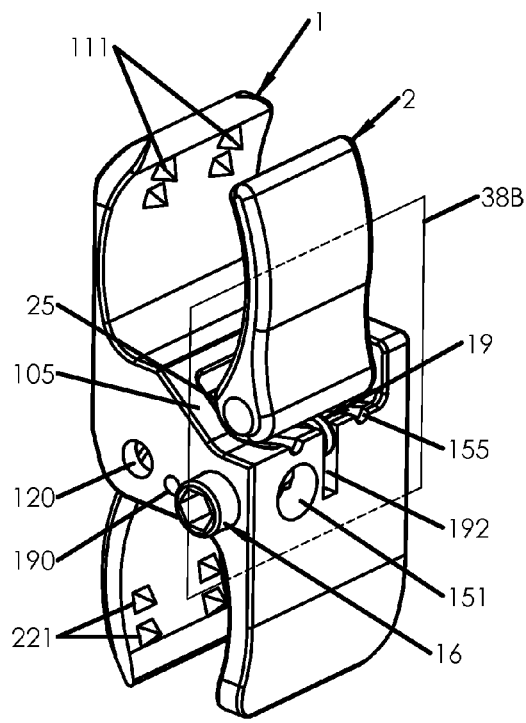
Figure 38B:
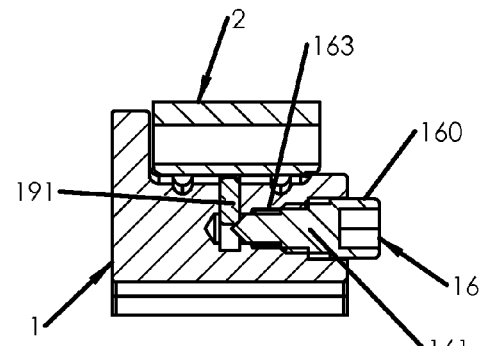
Figure 38C:
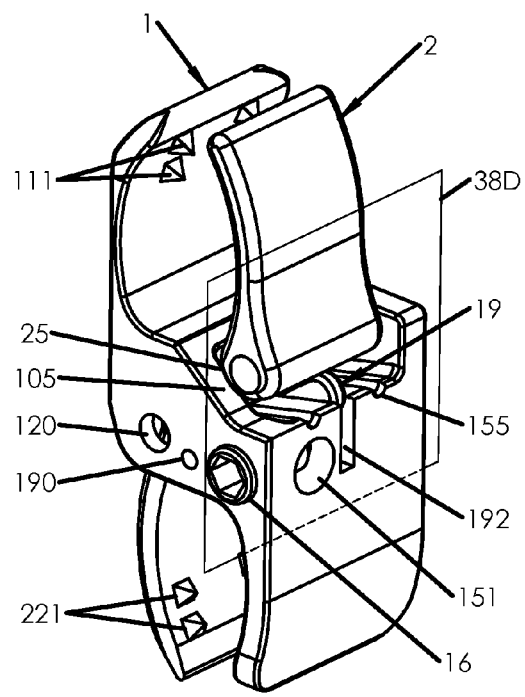
Figure 38D:
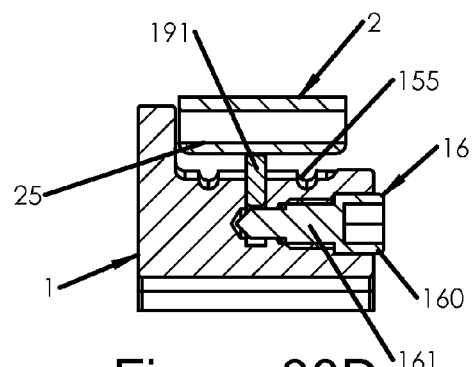
Figure 39A:
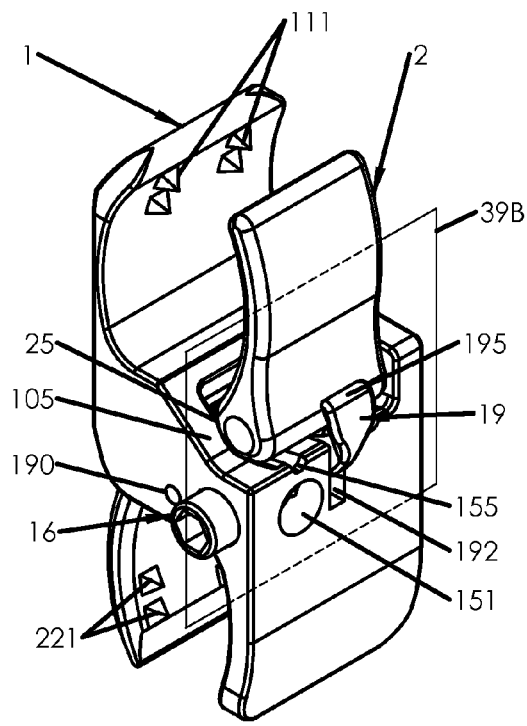
Figure 39B:
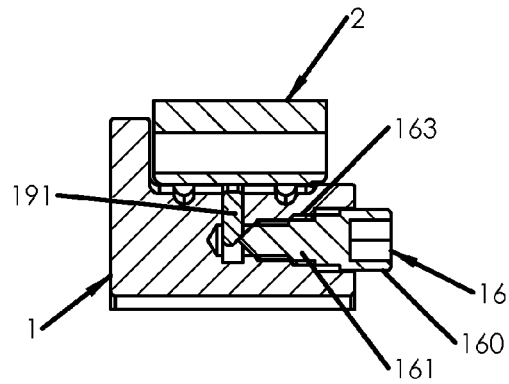
Figure 39C:
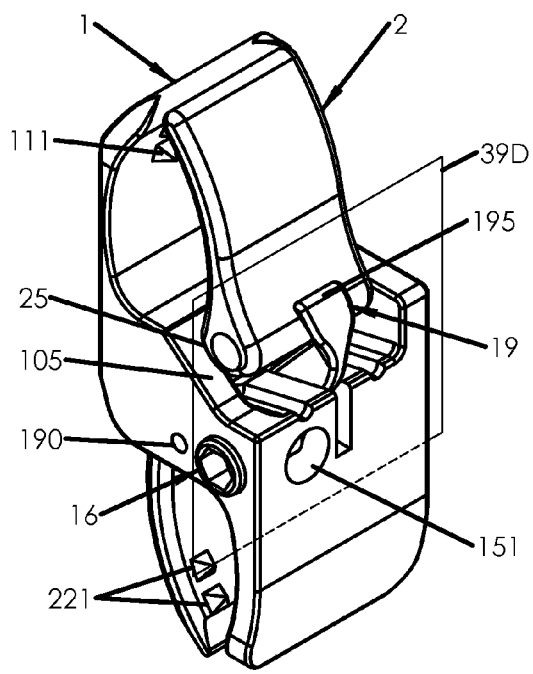
Figure 39D:
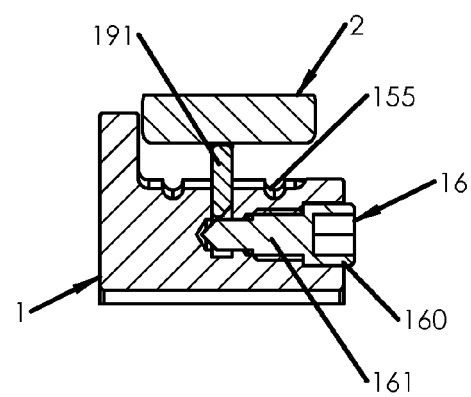
Figure 40A:
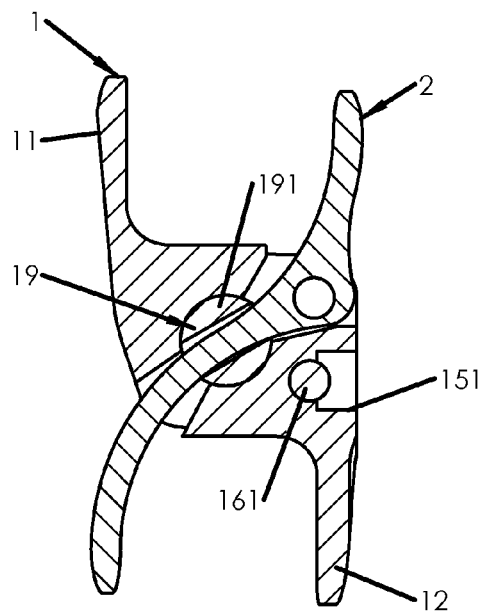
Figure 40B:
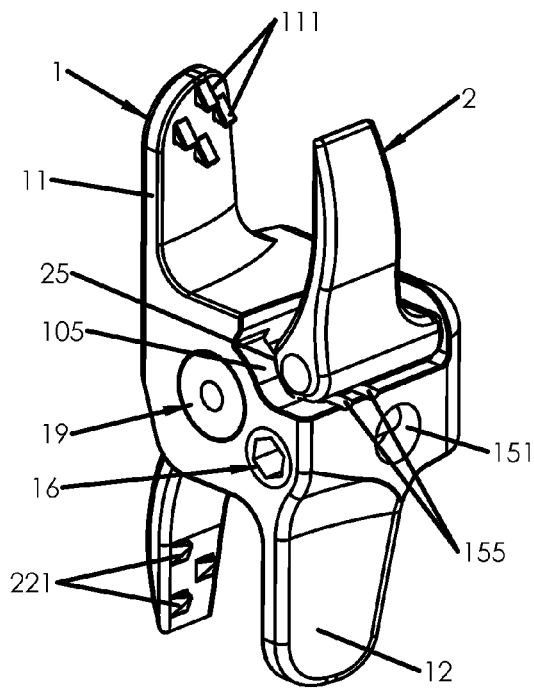
Figure 40C:
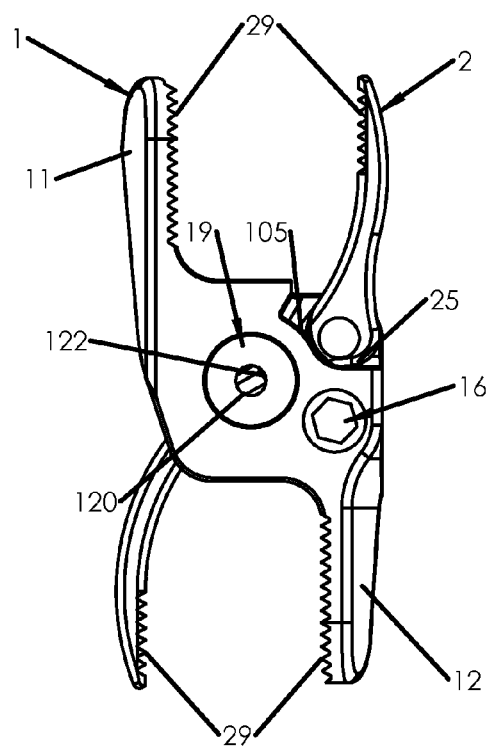
Figure 40D:
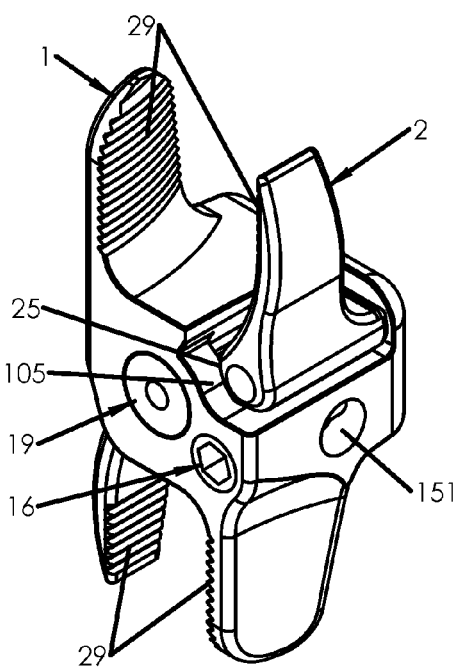
Figure 41A:
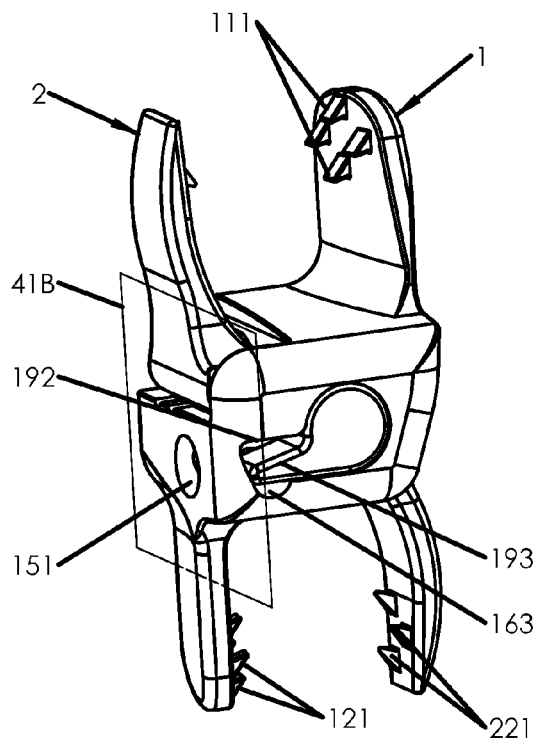
Figure 41B:
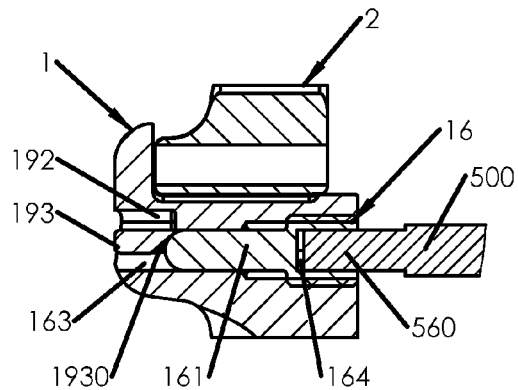
Figure 41C:
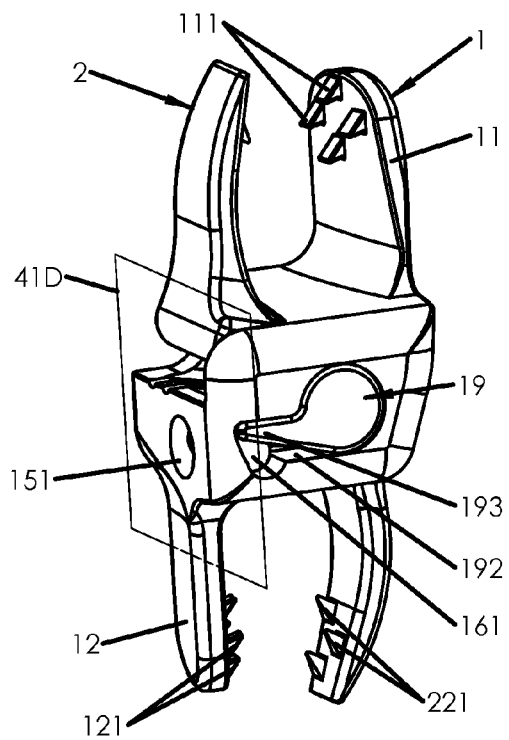
Figure 41D:
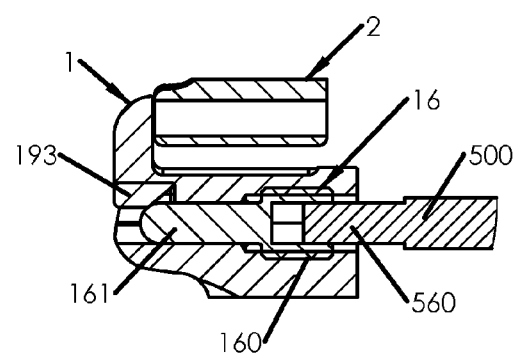
Figure 42A:
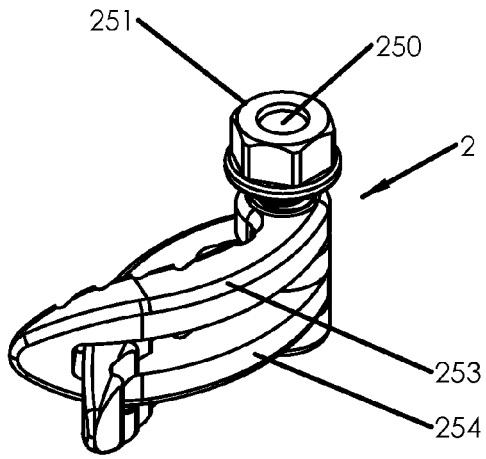
Figure 42B:
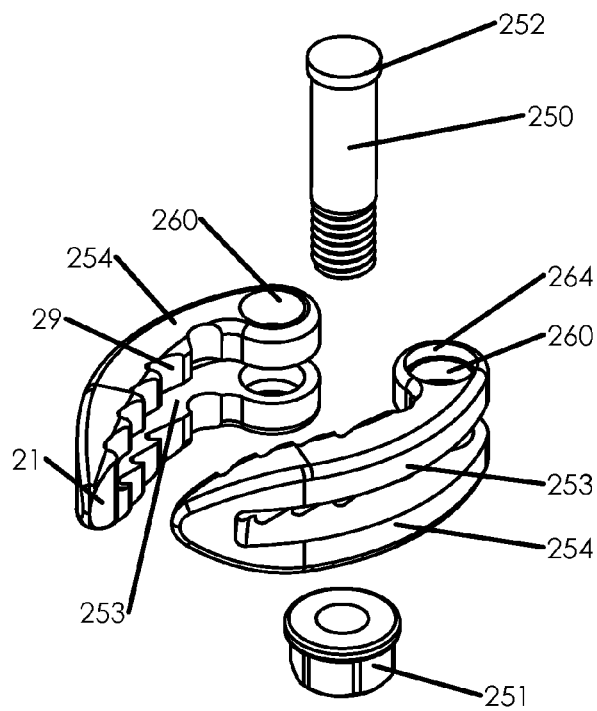
Figure 42C:
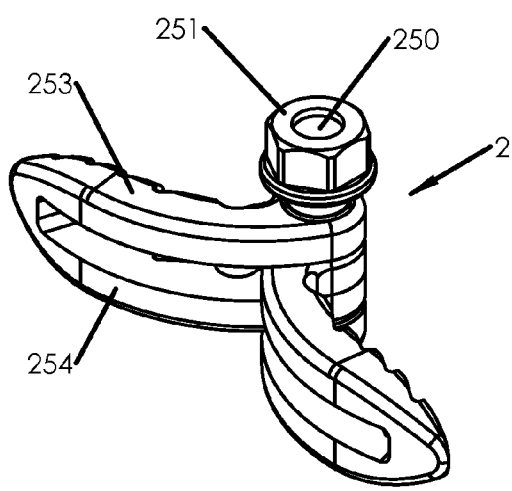
Figures 44A, 44B:
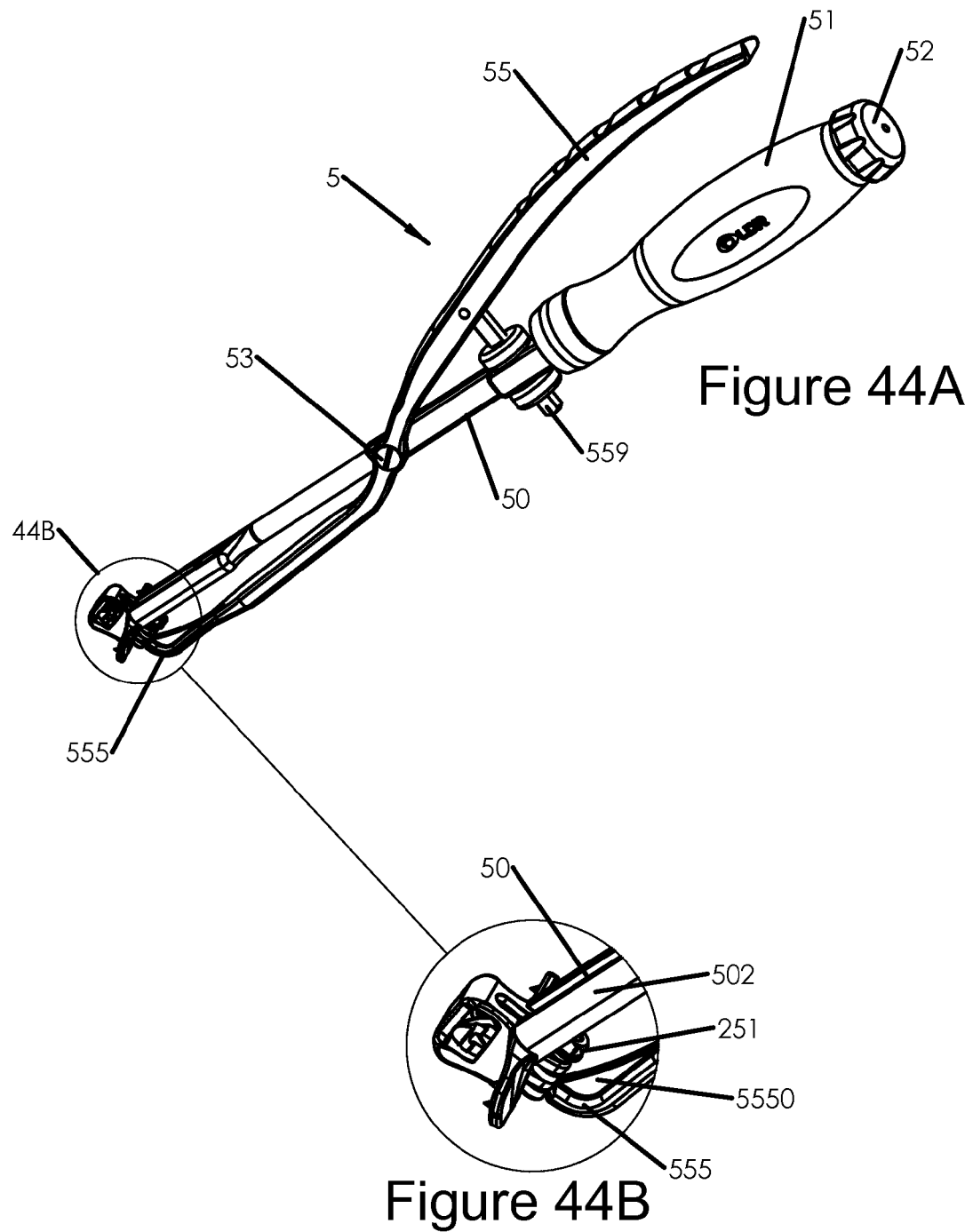
Figure 45A:
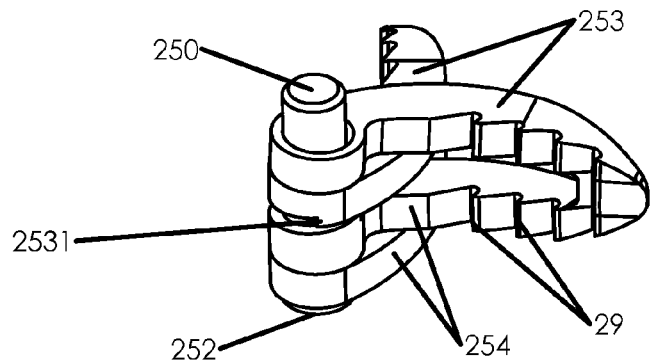
Figure 45B:
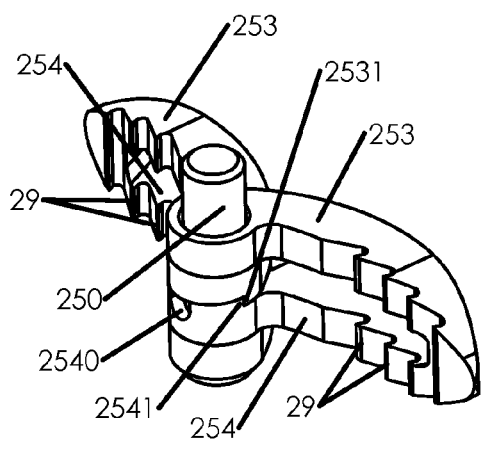
Figure 45C:
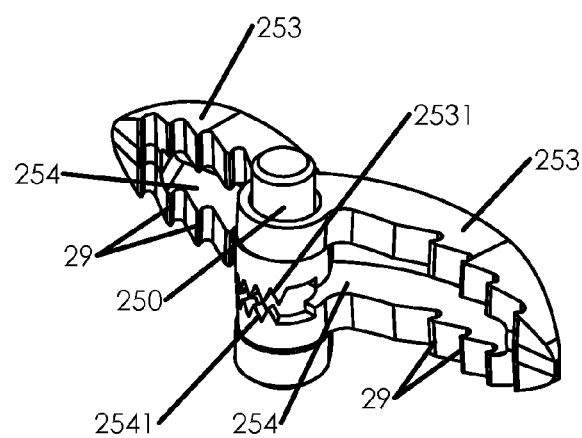
Figure 46A:
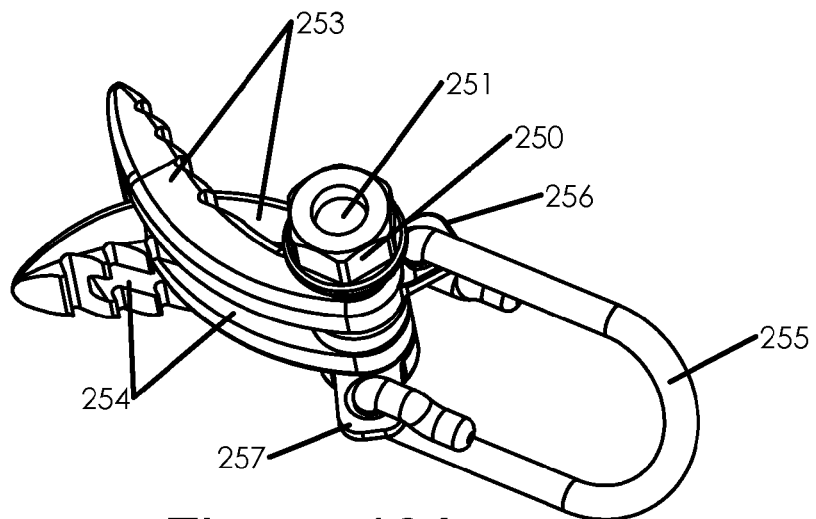
Figure 46B:
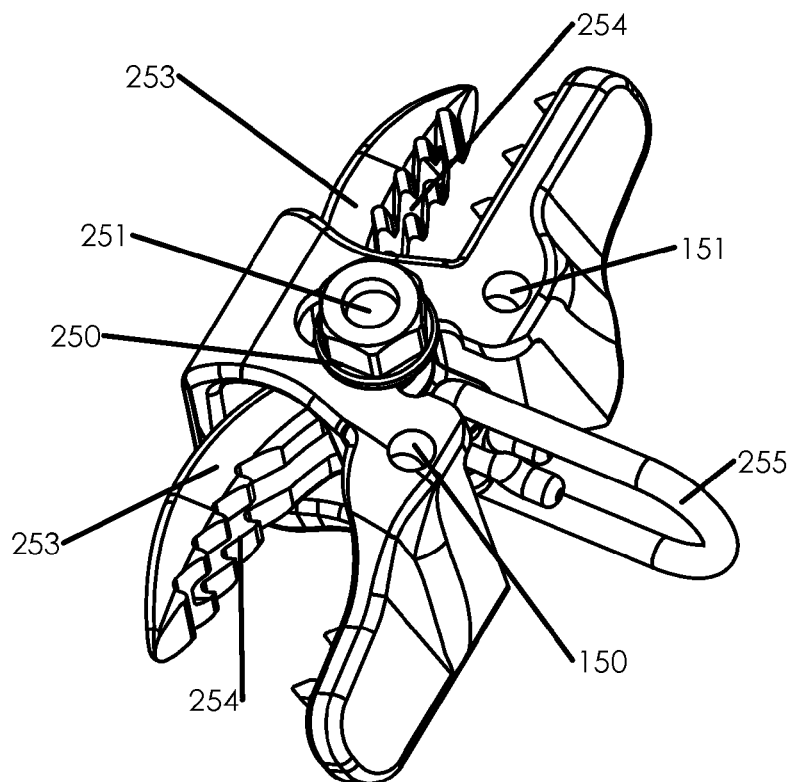
Figure 47A:
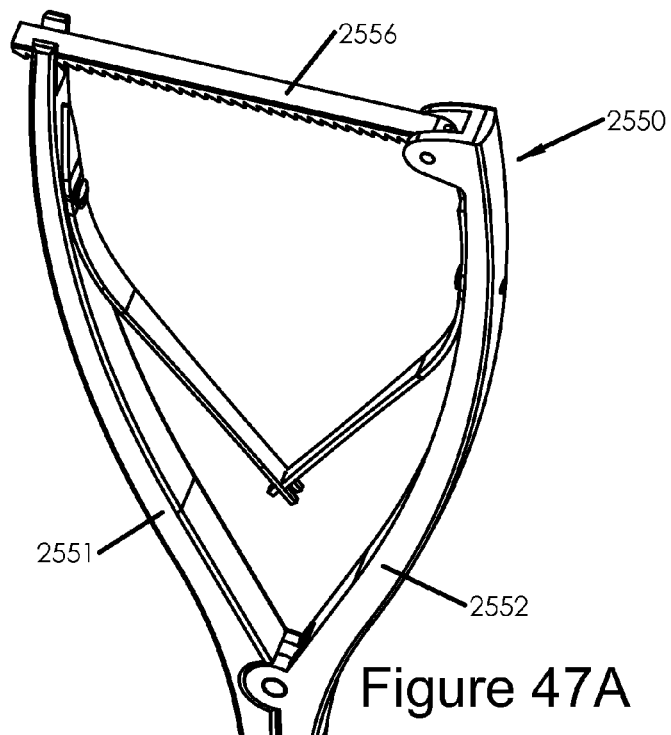
Figure 47B:
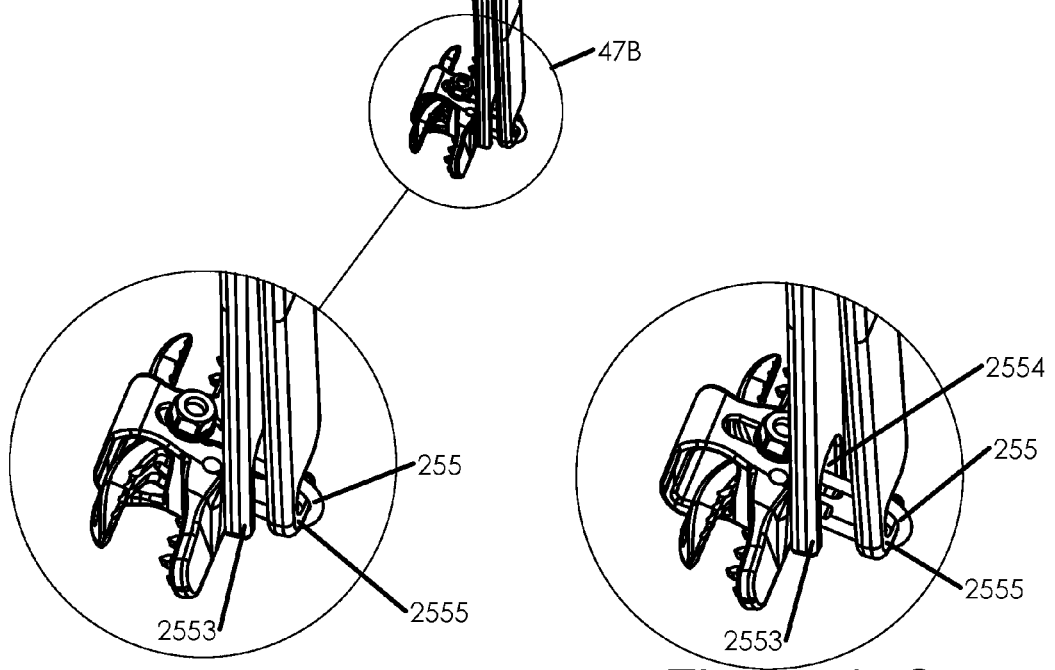
Figure 47C:
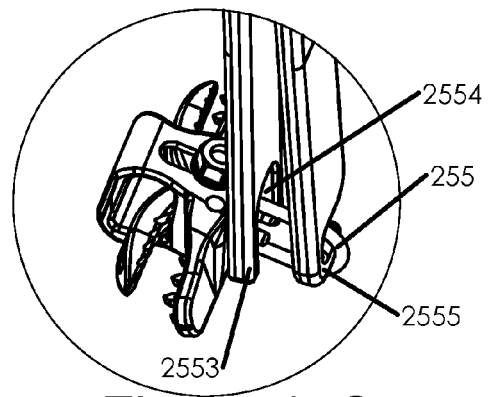
Figure 48A:
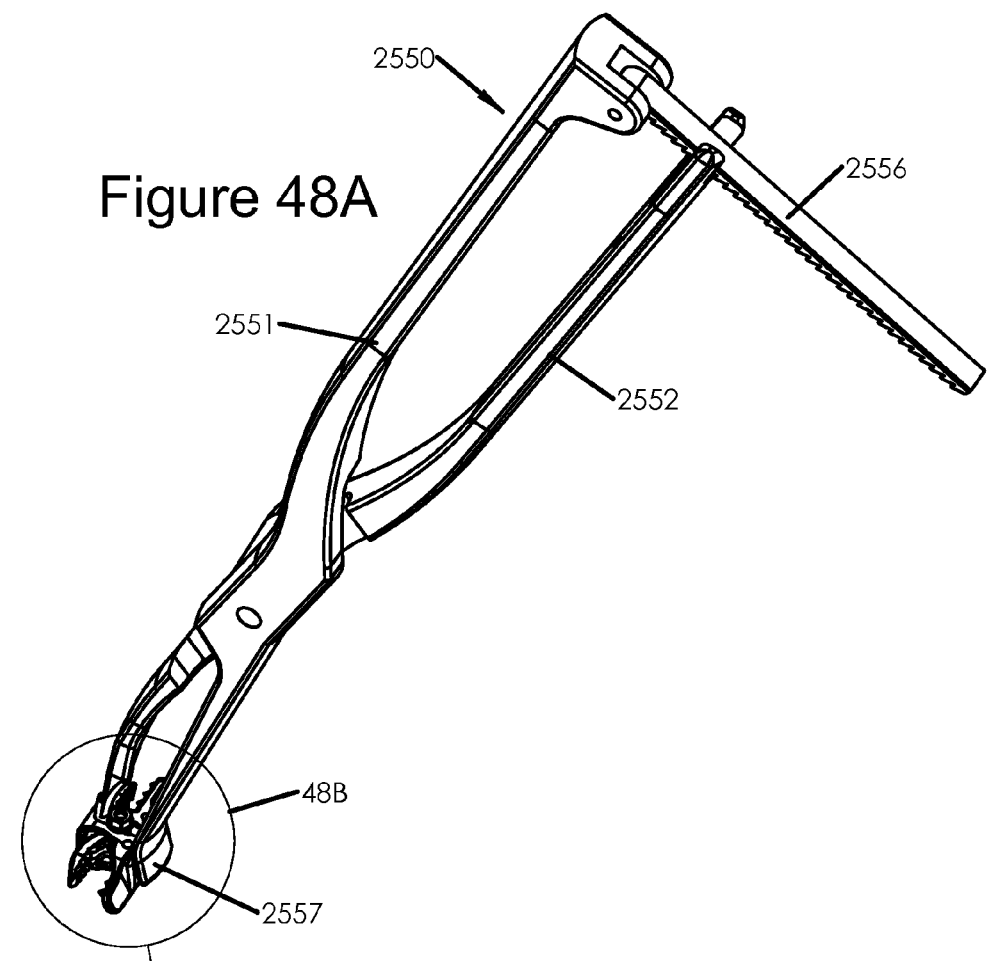
Figure 48B:
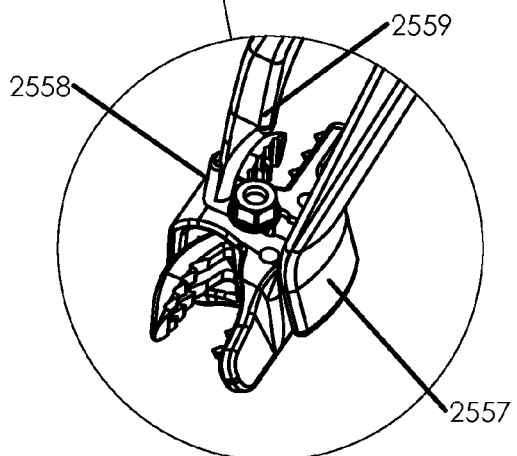
Figure 48C:
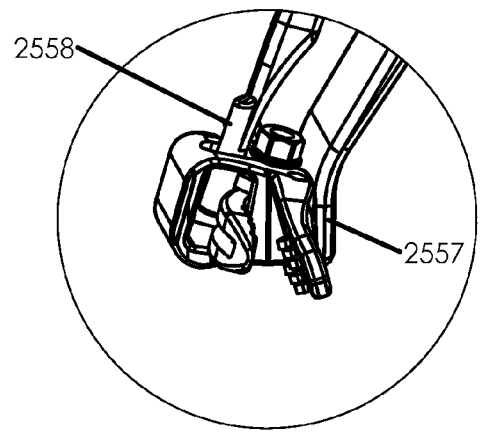

FIGS. 17A, 17B and 17C show three perspective views of an interspinous implant before, during and after its implantation between the two spinous processes, respectively, according to certain embodiments FIGS. 18A, 18B and 18C show, respectively, two top views and a perspective view of an interspinous implant according to some embodiments, FIG. 18A representing the implant when assembled with a bone anchor and FIGS. 18B and 18C representing the implant during its assembly with the bone anchor, FIGS. 19A, 19B and 19C show, respectively, two top views and a perspective view of an interspinous implant according to some embodiments, FIG. 19A representing the implant when assembled with a bone anchor and FIGS. 19B and 19C representing the implant during its assembly with the bone anchor, FIGS. 20A and 20B respectively represent a perspective view and a top view of an interspinous implant having hooking resources and bone anchoring resources according to some embodiments, FIGS. 21A and 21B are perspective views of an interspinous implant having hooking resources on a wing and on the insert, according to some embodiments, and FIGS. 21C and 21D are respectively a side view and a top view of an insert provided with hooking resources according to some embodiments, FIGS. 22A and 22B respectively represent a side view and a top view of an implant and a hooking device according to some embodiments, and FIGS. 22C and 22D are respectively a side view and a view top of a hooking device according to some embodiments, FIGS. 23A and 23B are perspective views of an implant and a hooking device according to some embodiments and FIGS. 23C and 23D are respectively a top view and a perspective view of a hooking device according to some embodiments, FIGS. 24A and 24C show two perspective views of an instrument equipped with actuating means for inserting an insert into the body of an interspinous implant according to some embodiments, respectively in an extended position and in an actuated position, FIG. 24B showing an enlargement of the area 24B indicated on FIG. 24A and FIG. 24D showing an enlargement of the area 24D indicated on FIG. 24C, FIGS. 25A and 25B show respectively a perspective view and a top cutaway view of an interspinous implant according to certain embodiments; FIGS. 25C and 25D show top views of this implant respectively during its implantation and after its implantation between two adjacent spinous processes, FIGS. 26A and 26B show respectively left and right posterio-lateral perspective views of an interspinous implant according to certain embodiments, implanted between two adjacent spinous processes, FIGS. 27A and 27B show a perspective view of an interspinous implant according to certain embodiments, respectively assembled and disassembled; FIGS. 27C and 27D show perspective views of an interspinous implant according to certain embodiments, in the folded and in the unfolded position respectively; FIGS. 27E and 27F show perspective views of an interspinous implant according to certain embodiments, assembled and disassembled respectively, FIGS. 28A and 28B show respectively a top and a perspective view of an interspinous implant according to certain embodiments, implanted between two adjacent spinous processes; FIG. 28C shows a perspective view of an interspinous implant according to certain embodiments, with flexible connector locking means disassembled, and FIG. 28D shows a perspective view of an insert for an interspinous implant according to certain embodiments, FIG. 29A shows a top view of an interspinous implant according to certain embodiments, implanted between two adjacent spinous processes, and FIG. 29B shows a perspective view of an interspinous implant according to certain embodiments FIGS. 30A and 30C show two perspective views of an interspinous implant placed between two spinous processes according to some embodiments, respectively, during and after implantation, FIG. 30B shows an enlargement of the portion 30B shown in FIG. 30A and FIG. 30D shows an enlargement of the portion 30D shown in FIG. 30C, FIG. 30E showing a top view of the implant according to these embodiments, FIGS. 31A, 31C and 31D show perspective views of an interspinous implant placed between two spinous processes according to some embodiments, FIG. 31B shows an enlargement of the portion 31B shown in FIG. 31A and FIG. 31E showing a view top of the implant according to these embodiments, FIGS. 32A and 32B are perspective views of an interspinous implant placed between two spinous processes according to some embodiments;

FIGS. 33A and 33B are perspective views of an interspinous implant placed between two spinous processes according to some embodiments;

FIGS. 34A and 34B are respectively a perspective view and a top view of an interspinous implant placed between two spinous processes according to some embodiments;

FIGS. 35A and 35B are respectively a perspective view and a top view of an interspinous implant placed between two spinous processes according to some embodiments;

FIG. 36A shows a bottom perspective view of an interspinous implant according to certain embodiments and FIGS. 36B and 36C show two bottom views of this implant, respectively before and after compression of the spinous processes;

FIGS. 37A and 37C show perspective views of an interspinous implant according to certain embodiments, respectively before and after pivoting of a latch for compressing the spinous processes and FIGS. 37B and 37D show section views, along the section planes 37B and 37D respectively, of the implant of FIGS. 37A and 37C, respectively;

FIGS. 38A and 38C show perspective view of an interspinous implant according to certain embodiments, respectively before and after pivoting of a latch for compressing the spinous processes. FIGS. 38B and 38D show section views along the planes 38B and 38D, respectively, of the implant of FIGS. 38A and 38C, respectively;

FIGS. 39A and 39C show perspective views of an interspinous implant according to certain embodiments similar to those of FIGS. 38A and 38C, respectively before and after pivoting of compression resources for the spinous processes. FIGS. 39B and 39D show section views along section planes 39B and 39D, respectively, of the implant of FIGS. 39A and 39C, respectively;

FIGS. 40A and 40B show respectively a coronal (i.e. frontal) section view and a perspective view of an interspinous implant according to certain embodiments. FIGS. 40C and 40D show respectively a top view and a perspective view of an interspinous implant according to certain embodiments closely related to those of FIGS. 40A and 40B;

FIGS. 41A and 41C show perspective views of an interspinous implant according to the embodiments of FIGS. 40A and 40B, respectively before and after pivoting of a plug for compressing the spinous processes and FIGS. 41B and 41D show section views along the section planes 41B and 41D respectively, of the implant of FIGS. 41A and 41C, respectively;

FIGS. 42A and 42B show respectively a perspective view and an exploded view of an arrangement for retaining an interspinous implant in the folded position according to certain embodiments, FIG. 42C showing a perspective view of this retaining arrangement in the deployed position;

FIGS. 43A and 43B show respectively a perspective view and a section view in section plane 43B of FIG. 43A, of an interspinous implant according to certain embodiments, in which is inserted, in the folded position and held by a pin, a retaining arrangement of the type exemplified in FIGS. 42A, 42B and 42C, FIGS. 43C and 43D showing perspective views of this implant of FIG. 43A without the pin and with the retaining arrangement in the deployed position;

FIG. 44A shows a perspective view of an embodiment of an implantation instrument for various embodiments of an interspinous implant, for example the embodiments of FIGS. 43A, 43B, 43C and 43D, and FIG. 44B shows an enlargement of portion 44B of FIG. 44A, showing the end of the instrument bearing an exemplary implant;

FIGS. 45A and 45B show perspective views of an embodiment of a retainer for various embodiments of an interspinous implant, forming compression resources for spinous processes, according to some embodiments, and, respectively, in a folded position and a deployed position, and FIG. 45C shows a perspective view of a similar retainer, but according to other embodiments;

FIGS. 46A and 46B show perspective views, respectively, of an embodiment of a retainer for various embodiments of interspinous implants and of an interspinous implant equipped with such a retainer forming compression resources of spinous processes, according to some embodiments;

FIG. 47A shows a perspective view of some embodiments of an instrument for compressing spinous processes by actuating an embodiment of an interspinous implant equipped with compression resources, FIG. 47B shows an enlargement of the area 47B in FIG. 47A and FIG. 47C shows the same type of enlargement, but when compression is performed;

FIG. 48A shows a perspective view of some embodiments of an instrument for compressing spinous processes by actuating an embodiment of an interspinous implant equipped with compression resources, FIG. 48B shows an enlargement of the area 48B in FIG. 48A and FIG. 48C shows the same type of enlargement, but when compression is performed.

DETAILED DESCRIPTION OF VARIOUS EMBODIMENTS

The present invention concerns an interspinous implant (1) intended to be implanted between the spinous processes (dorsal vertebral apophyses or feather bones or spinal crests) of two adjacent vertebrae. In the present application, the spinal crests or spinous processes of the vertebrae are designated by the terms "vertebral spine", "dorsal spine", "spinous processes" or quite simply "spine" (while the vertebral column will therefore be called "rachis" instead of the commonly used term "spine"). The spinous processes are the rearmost structures of the vertebral column and therefore potentially afford the quickest access (they can actually be palpated below the skin from C7 to L5), which makes certain interspinous implants easy to implant but can impose the stability and implantation constraints discussed in the present application. Thus the space that separates two adjacent spinous processes is designated in the present application by the term interspinous space. Certain embodiments allow the insertion of several implants between the consecutive interspinous spaces of several (more than two) adjacent vertebrae, as detailed in the present application.

The dorsal spines (EI, ES), generally substantially aligned in the median sagittal plane (or approximately oriented in that plane), have materially the shape of a disc or plate, of generally oblong or elliptic section in the coronal plane, with an extremity (a crest) pointing rearward of the patient. The spinous processes have, referring to the longitudinal axis of the vertebral column, an upper edge (E2), a lower edge (E3) and two opposite lateral faces (E4, E5).

FIGS. 16A and 16B showing schematically perspective views of the constitutive elements of two adjacent vertebrae, with the median sagittal plane (A) and a Cartesian benchmark (X, Y, Z) which is used as a reference in the present description for the sake of simplification. These figures show a lower vertebra (VI) with its spinous process, also called lower (EI), and an upper vertebra (VS) with its spinous process, also called upper (ES) and show the edges (E2, E3) and faces (E4, E5) of each of these upper (ES) and lower (EI) spinous processes. The present application describes certain elements of the implant with reference to its positioning once implanted in the body of the patient, for greater clarity regarding the localization of the various elements of the implant with respect to the vertebral structures. In FIGS. 16A and 16B, the patient is considered to be in a horizontal position, lying face down. The Cartesian benchmark shown comprises three mutually orthogonal directions (X, Y, Z). The X direction corresponds to the rising longitudinal axis of the vertebral column, the Y direction corresponds to the anteroposterior axis and the Z direction corresponds to the mediolateral axis. Thus the X and Y axes define a sagittal plane (A), the X and Z axes define a coronal plane and the Y and Z axes define a transverse plane of the patient. The present application will be able to refer to these patient planes for the implant itself, since the implant is intended to be implanted with its wings located to either side of the sagittal alignment plane of the spinous processes, as can be seen in particular in FIGS. 17A through 17C. The terms "upper" and "lower" are therefore used in the present application with reference to the X axis. A top view is a view by which the vertebral column or the implant is seen from behind the patient lying face down and a side view is a view by which the vertebral column or the implant is seen from a lateral face of the vertebral column or of the implant according to the same reference. These view and orientation considerations are used independently of whether the implant is implanted or not, and it will be understood that they relate to the implant in its implantation site but that they are not limiting. In addition, it will also be understood from the present application that the implant can be reversed depending on the face of the vertebral column through which the surgeon wishes to approach the interspinous space. Further, it will be understood that the invention allows the spinous processes to be approached through one lateral face of the vertebral column, but the approach is preferably not carried out perpendicularly to the sagittal plane (along the Z axis), but rather substantially parallel to the Y axis or preferably along an oblique axis which is oriented rearward of the patient (an axis oriented between the Y and Z axes, but also eventually non-parallel to the X axis if necessary). It will be understood, however, that the insertions of the implant and of the insert are preferably performed substantially parallel to the Z axis. Finally, still referring to these benchmarks on the patient, the terms "height" (particularly of the implant) or "length" (particularly of the wings or of the insert) are used to designate a dimension along the X direction, the terms "width" (particularly of the implant) or "thickness" (particularly of the wings or of the insert) to designate a dimension along the Z direction and the term "depth" to designate a dimension along the Y axis. Said terms used for dimensions along the axes and directions of the benchmark are not limiting and do not signify that the elements in question are necessarily oriented exactly along the axis referred to and this reference could refer to their orthogonal projection onto the axis or their dimension along an axis approximately oriented in the same direction as the axis referred to.

Various embodiments of the interspinous implant have a longitudinal body (10) with dimensions arranged so as to maintain or restore a distance between the adjacent edges (E2, E3) of the two spinous processes (EI, ES) between which it is intended to be implanted (the adjacent edges meaning here the neigbouring edges of two successive spinous processes, that is to say two edges of spinous processes facing each other). In fact, an interspinous implant is intended to be inserted between two spinous processes (EI, ES) to maintain the space separating them at a physiological value (or possibly a corrective value, that is a value imposing lordosis or kyphosis). The surgeon therefore may select a predetermined height of the body (10) of the implant according to the spacing that he wishes to maintain (or to restore in the case of insufficient spacing) between the two adjacent spinous processes (EI, ES) of interest. In various embodiments, the implant (1) includes at least two wings (11, 12) (or arms or blades or legs) extending in such a way that at least part of each wing (11, 12) lies along at least a part of a lateral face (E4, E5) of one of the two spinous processes (EI, ES). Thus, in these embodiments, each wing of the implant extends from the body (10) embedded in the interspinous space to a lateral face (E4, E5) of one of the spinous processes (EI, ES). The implant (1) includes preferably only two wings (11, 12) so as to facilitate its implantation between the spines (EI, ES). The interspinous implant (1) can also be inserted between the spines from a single lateral face of the vertebral column and its wings (11, 12) constitute extensions which stabilize the body (10) in the interspinous space by extending beyond that interspinous space (each lying alongside a lateral face of one spine). Further, the implant (1) includes at least one retainer (2, 3, 4, 7, 111, 121, 221, 24, 28, 29, L, 90) for the implant, designed to retain the body of the implant between the two spines. This retainer (or retaining resources or arrangement) is designed to constitute a retention structure for the implant with respect to the two spines, that is it avoids allowing the body to migrate within the interspinous space, or become dislodged from it. The wings, in their function of retaining or supporting the implant between the spines, are therefore supplemented by this retainer, preferably in that at least a portion of this retainer is located at the spine faces opposite those along which the wings already lie, once the implant is assembled with this retainer. The term "at" is used here because it will be understood from reading the present application that this portion of the retainer can lie against, or near, or even across these faces opposite to those along which the wings lie. It will be noted that the term "at least one" retainer is used here because there can be several retainers of the same type or of different types because the various embodiments of this at least one retainer are often not mutually exclusive. It will be noted that this function of retention or support is mainly oriented mediolaterally, that is transversely to the axis of the vertebral column (that is along the Z axis) but that in certain embodiments the retainers also offer antero-posteriorly oriented support (along the Y axis) and/or longitudinally oriented support (along the X axis). Preferably, the at least one retainer (2, 3, 4, 7, 111, 121, 221, 24, 28, 29, L, 90) is designed to be implanted from a single lateral face of the vertebral column, preferably the same one as that through which the body (10) of the implant (1) is implanted. An implant is thus obtained which is easy to insert and minimizes the lesions needed for its implantation. Indeed, the assembly of the interspinous implant from distinct parts, in particular a body and at least one retainer, allows the implant to be easily implanted in a very non-invasive manner by a posterior unilateral approach (that is from a single lateral face, for example along an oblique axis drawn between the Y and Z axes) without withdrawing (or cutting or too greatly wounding) the subspinous ligament and passing through the interspinous ligament while minimizing damage to the last mentioned. Thus, this configuration allows the implant to extend sufficiently within the interspinous space and at its edges to allow it to be installed in a stable fashion.

According to various embodiments that are not necessarily mutually exclusive, the at least one retainer (2, 3, 4, 7, 111, 121, 221, 24, 28, 29, L, 90) of the implant (1) can include:

two curved inserts (2), as for example in the embodiments shown in Plates 1 and 2 of the figures, one curved insert (2), in the case of a body (10) including a third wing (17), as for example in the embodiments shown in Plate 3 of the figures, one insert (2) with two radii of curvature having opposite orientations, such as a sigmoid-shaped insert, as for example in the embodiments shown in drawing Plates 5, 10, 13 or 17 of the figures, a complementary body (90), for example substantially symmetrical with respect to the body (10) of the implant (1), as for example in the embodiments shown in drawing Plate 27 of the figures.

Furthermore, in certain embodiments, the at least one retainer (2, 3, 4, 7, 111, 121, 221, 24, 28, 29, L, 90) provide(s), in addition to the function of retaining or holding the implant between the spines, a function of retaining or maintaining the two spines relative to one another. Indeed, even with an implant inserted between the two spines, the last mentioned are possibly able to move relatively to one another, in particular during rotational or extensional motion of the vertebral column. Thus, in certain embodiments, the at least one retainer (2, 3, 4, 7, 111, 121, 221, 24, 28, 29, L, 90) allow(s) the two spines to be retained relative to one another (and generally with respect to the implant). For example, in certain embodiments of the inserts (2) and/or of the supplementary bodies (90), the two spines can be held in alignment in the same sagittal (or possibly para-sagittal if the patient's vertebral column requires it) plane. In addition, various embodiments of the at least one retainer also allow the two spines to be held at a maximum spacing or within a determined range of spacings (the minimum spacing being imposed by the height of the body as explained above). According to various embodiments which are not necessarily mutually exclusive, the at least one retainer (2, 3, 4, 7, 111, 121, 221, 24, 28, 29, L, 90) of the implant, also constituting at least one retainer of the spines, can include:

at least one flexible connector (L), also called a ligament (L), as for example in the embodiments shown in drawing Plates 25 and 26 of the figures, at least one bone anchorage means, such as points (111, 121, 221), particularly threaded ones, staples (3), anchors (7), pivoting hooks (28), or even antiskid notches (29), as for example in the embodiments shown in drawing Plates 4, 6, 7, 8, 11, 18 and 19 of the figures, at least one additional means of hooking onto a spine, such as hooks designed to achieve a grip on the edges of the spines, whether formed by the insert (for example as on drawing Plate 21), or mounted on the insert (for example as on drawing Plate 20) and/or the implant, or separate from the rest of the implant and attachable or not, as for example in the embodiments shown in Plates 20, 21, 22 and 23 of the figures.

The present application describes in detail the possible arrangements for these various types of the at least one retainer (2, 3, 4, 7, 111, 121, 221, 24, 28, 29, L, 90), as well as their respective advantages.

Thus, in certain embodiments, the implant (1) includes, firstly, at least two wings (11, 12) extending so that at least a portion of each wing (11, 12) lies along at least a portion of a lateral face (E4, E5) of one of the two spines (EI, ES) and additionally, at least one passage (15) passing through at least a portion of the body (10). In various embodiments, this passage has a shape, dimensions and orientation arranged for the insertion, through the body (10), of at least one insert (2). In various embodiments, the insert (2) may include at least a curved plate and is retained within the body (10) so that at least a part of said curved plate lies along at least a part of a lateral face (E5, E4) opposite a lateral face (E4, E5) having a wing (11, 12) lying along it (at least one of the lateral faces when the implant lies along both faces, as detailed in some embodiments of the present application). It is understood that this results in at least one wing of the implant lying along a lateral face of a spinous process, the other lateral face of which has at least a part of at least one insert lying along it. In these embodiments, this configuration allows the body to be inserted from a lateral face opposite which will be arranged a wing, and then an insert (2) to be inserted in the passage (15) of body (10), by the same lateral face, with a curved part of the insert (2) making it possible to position the insert (2) facing the opposite lateral face (located on the other side of the spinous process, and to which there is therefore no direct access).

In the present application, the term "wing" designates an element of the implant (1) which extends in the direction of the lateral faces of the spinous processes (generally longitudinally and substantially along the X axis) and should not be interpreted in a limiting way because the wings can have various shapes, some examples of which are detailed in the present application. It will be noted in particular that the wings are preferably not hinged to the body and are in fact extensions of the body (for example on the lateral faces or on the upper and lower faces, or rather at the junction of these faces). If these wings were hinged, they would have to include a locking mechanism for the hinge so as to fulfill their function of retaining the implant. Generally, the wings (which could be called arms, legs, extensions or something else) can be in the form of a straight or curved plate and will preferably have shapes and dimensions designed for good holding of the implant between the spines. Generally, the wings (which could be called arms, legs, extensions or else) can be in the shape of a straight or curved plate and will preferably have shapes and dimensions suited to good retention of the implant between the spinous processes. For example, in the case of curved wings, the insertion of the implant will be facilitated in many embodiments (particularly embodiments where the wings are not on the same lateral face of the implant) and the free end of the curved wings will be closer to the lateral faces of the spinous processes than the rest of the implant or even in contact with these lateral faces to allow good retention of the implant between the spinous processes. The dimensions of the wings can also be matched to the dimensions of the lateral faces of the spinous processes. For example, the wings can have a length (along the X axis) on the order of half that of the lateral faces of the spinous processes or even greater (which may be particularly advantageous for providing stability and which is possible even in certain embodiments where the wings have shapes arranged to allow the implantation of several implants in consecutive interspinous spaces of several consecutive vertebrae of the vertebral column, for example as detailed in the present application). The depth of the implant can generally vary according to the size of the spinous processes along the Y axis and/or the surgeon's preference, to offer more or less support for the spinous processes, thanks to contact with a more or less extensive surface on the upper and lower edges of the spinous processes. This depth can also be determined according to the desired total volume of the implant, to minimize the injuries necessary for its implantation. Thus the body (10) can have a depth so determined and the wings (11, 12) can have a substantially identical or different depth. Moreover, the depth of the implant, of the body and/or the wings in particular, can vary over the height of the implant, for example as shown in FIG. 1B where it can be seen that the free end of the wings has smaller dimensions than the rest of the implant so as to facilitate the insertion of the wings into the interspinous space.

Generally, the wings (11, 12, 17) have a shape and dimensions arranged so as to facilitate the positioning of the implant (1) between the two dorsal spines (EI, ES) while still ensuring good retention once implanted. The verb phrase "to lie along" (or "run") is used in the present application because the wings (11, 12) of the implant (1) are arranged so as to lie along the lateral faces of the spinous processes (EI, ES) but are not necessarily in contact therewith. These wings may be straight or curved and may or may not be parallel to said lateral faces, so that the implant can for example have an H or X shape viewed from the top or in section in the coronal plane (i.e., frontal plane), with a wing (11, 12) forming a half-branch of the H or the X and a part of the insert (2) or inserts (2) protruding outside the body (10) forming another half-branch of the H or the X. In addition, the implant (1) may have a shape and dimensions arranged so that a slight lateral play is or is not possible (along the Z axis), to allow or not allow relative motion of the dorsal spines (EI, ES), that is a torsional motion obtained by relative rotation of the vertebrae with respect to one another (for example, when the patient turns to one side). Thus the spacing between a wing and the part of the insert that faces it (on the opposite face) can vary depending on the width of the spinous processes and/or on the play that may be desired. Similarly, the body (10) can have a variable width, but it is the spacing between a wing and the part of the insert that faces it that matters because the body can have a width greater or smaller than this spacing without necessarily influencing the possible play of the spinous processes. If no play is desired, the implant can be arranged so that there is contact on both faces of each spinous process, to prevent any movement. In the case where lateral play is possible, the amplitude of the last-mentioned can be selected so as to limit or not the relative motions of the spinous processes by adjusting the spacing between each wing and the part of the insert that faces it. It is possible for example to change the position and/or the orientation of the passage (15) and/or the radius (radii) of curvature of the insert (2).

As regards the implant which is intended to be inserted into the interspinal space through a lateral face of the vertebral column, the term "front" or "anterior" lateral face is used to designate the lateral face of the implant that is inserted first, while the term "back" or "posterior" lateral face is used to designate the lateral face which remains on the lateral face of the vertebral column through which the interspinous space is approached. It is therefore understood that the insert is inserted into the passage by the back lateral face, while the passage outlet can be on the front lateral face or on either the upper or lower face or even at the junction between the front lateral face and one of the last-mentioned. As for inserts that project, once placed in the passage directed toward the spinous processes, it is also possible to define lateral faces on which occur the concave and convex faces of the curved plate. As the insert has a direction for insertion into the implant, the term "anterior" or "front" is used to designate an element with respect to the anterior end which corresponds to that inserted first, and the term "posterior" or "back" is used to designate an element with respect to the posterior end which corresponds to the end by which the insert is pushed into the passage in the implant. As the insert is generally in the form of a plate, it is understood that the length of the insert refers to the dimension from between the anterior and posterior ends of the plate, while the width refers to the smaller dimension of said plate. The terms thickness and edges of the plate or of the insert are generally well understood by one skilled in the art, particularly because the other dimensions of the insert are defined here.

The interspinous implant (1) of various embodiments has a body (10) having at least two wings (11, 12) and at least one passage (15) arranged to receive at least one insert (2) retained within the body (10) once it is inserted into the passage (15) until a portion of the insert (i.e. part of its length) projects from the outlet of the passage to face the wing on the lateral face other than the one where the insert was inserted, so that the implant lies along at least a part of the two lateral faces of the spinous processes (with or without contact), whereby the implant is held stably and is not liable to disengage from the interspinous space. It can be considered that the implant (1) includes the insert (2) as they are arranged to be assembled together into a final implant. Nevertheless, implant bodies can be provided with other types of inserts than those described in the present application or, conversely, other bodies can be used with the same types of inserts as those described in the present application. In addition, because the insert has advantageous features as a retainer for the interspinous implant, it can be considered as an invention and claimed as such, for example in its use with at least one implant including a passage for such retainer.

Preferably, the trajectory of the passage(s) (15) through the body (10) is substantially rectilinear in order to facilitate its manufacturing. Moreover, the insert is preferably arranged so as not to be flexible and not to deform while passing in the passage, for example due to its material and/or its dimensions. Thus, once lodged in the implant in place in the patient, the insert is not liable to deform under the effect of movements of the spinous processes when the patient moves. A slight possible deformation of the insert and/or the body can nevertheless be provided for, but it must then have sufficient elasticity to return to its position of rest. Thus, care should preferably be taken to provide an insert which allows stable retention and which will not deform excessively or definitively during its insertion or under the effect of movements of the spinous processes and/or which won't definitively deform the body. Thus, with a rectilinear passage trajectory and a curved insert which is not inserted by deformation within the rectilinear passage, it is understood that it is preferable that the passage have dimensions (a height) greater than the thickness (height) of the insert and suited to the radius of curvature of the insert, so that the insert can pass without definitive deformation of the insert and/or the body. In certain embodiments, however, passages (15) could be provided with a curved trajectory matching the curve of the insert (2), though that necessitates more complex machining and/or assembly of the body in two parts or a curved core in the case of molding. For example, in the case of certain materials, certain known machining techniques allow a curved passage to be provided and in the case of molding, it's possible to provide for a curved core to be inserted in the mold, but these techniques complicate the manufacture. Moreover, in certain embodiments inserts (2) may be deformable, preferably in an elastic manner, particularly in the case of inserts (2) designed to be anchored in the spinous processes. In fact, anchorage in the spinous processes offers greater stability to the implant and reduction of the risk of migration of the implant, even if the insert deforms under the effect of loads. Finally, the passage (15) is preferably slightly flared at its entrance and/or outlet to facilitate the placement of the insert (2) within the body (10).

Figure 11A:
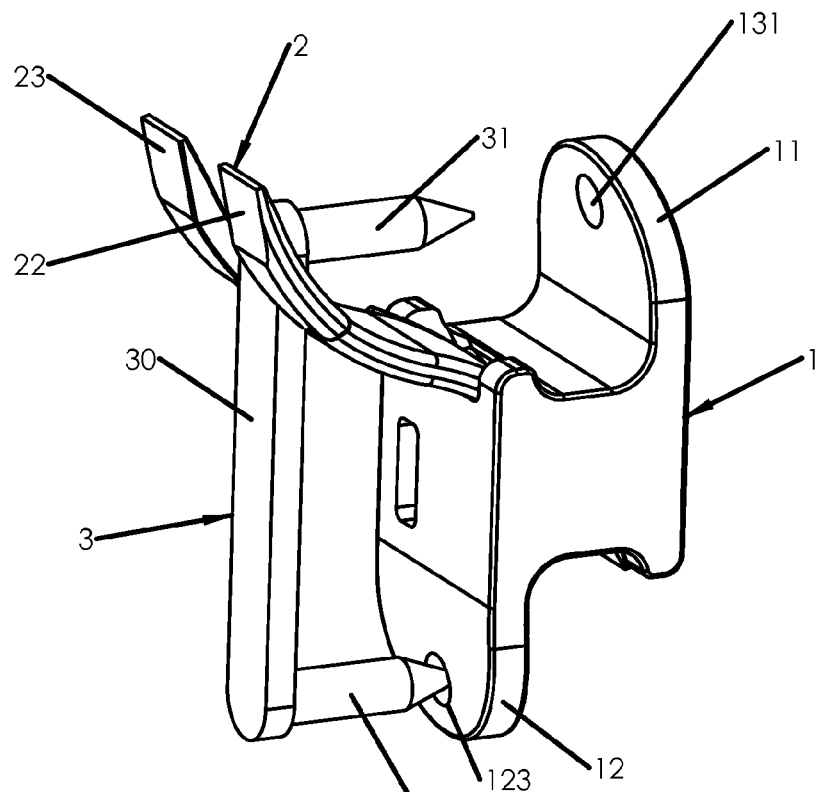
FIGS. 11A and 11B show a perspective view and a longitudinal section view, respectively, of an interspinous implant according to certain embodiments, and in the disassembled and assembled condition, respectively.
Figure 11B:
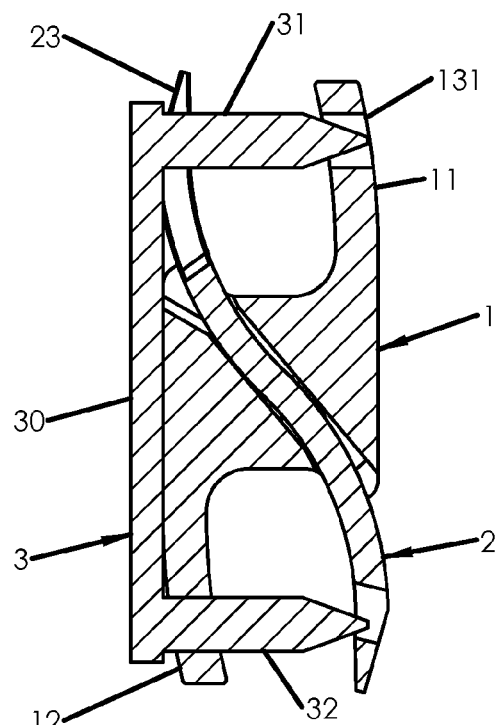

In some embodiments, in particular when the passage, generally rectilinear, has a height greater than the thickness of the plate of the insert (2), the height and length of the passage (15) are preferably set (arranged) according to the thickness and radius of curvature of the plate of the insert (2), and vice versa, so that the insert has at least three points of contact in the passage (15) when it is completely inserted (final position) in said passage, at least two of these contact points being on opposite sides of the insert (2), so that the latter has minimal clearance in the passage. For example, FIG. 11B shows a sectional view with the sigmoid insert (2) in its final position that has, with the walls of passage, a point of contact by the concave side of its anterior near the exit of the passage, a point of contact by the convex face of the anterior end near the transition between the two radii of curvature of the sigmoid plate and a point of contact by the convex face of the posterior end near the transition between the two radii sigmoid curvature of the plate. It is seen from this figure that a fourth point of contact is possible by the concave side of the posterior end near the entrance of passage. It will be understood that in such embodiments, the insert (2) is usually inserted in the passage with a slight reversible deformation (of the insert and/or body) and that the curvature of the insert is arranged as a function of the dimensions of the passage (and vice versa) so that the insert (2) limits its play in the passage, once implanted, by contacting the walls of the latter at several contact points or surfaces. The insert (2) thus has virtually no clearance in the passage and the only play allowed is due to the elasticity of the insert (2) and/or body (10). A slight deformation of the insert and/or body will therefore generally occur during the introduction of the insert, which may have both sides contacting with the walls of the passage and stabilizing the insert in the passage.

In some embodiments, in particular when the passage, generally rectilinear, has a height greater than the thickness of the plate of the insert (2), the latter comprises a thickening, a protrusion or a boss, arranged to come into contact with a wall of passage (15), so that both sides of the plate of the insert (2) come into contact with the walls of the passage at the level of this thickening, thereby stabilizing the insert (2) in the passage (15). This thickening of the insert (2), allowing contact with the walls of the passage, makes it possible to limit the play of the insert in the passage. Preferably, this thickening is progressive along the insert's anteroposterior direction, so that it may gradually press the insert in the passage while avoiding them to be injured. Thus, for example, the thickening may comprise, at least at its front end, at least one chamfer. Furthermore, in embodiments where the passage includes at least one flare at its entrance (the portion that receives the insert first), the insert may include a portion complementary to this at the entrance of passage to stabilize the insert. Thus, the thickening of the insert may be arranged to make contact with the flare of the passage. Moreover, in some advantageous embodiments, the thickening or boss is formed by part of the insertion stop (25). For example, in FIGS. 9A and 9B, the insertion stop (25) shown actually forms a thickening for stabilization in the passage, in addition to forming an insertion stop. This thickening is complementary to the flare at the entrance of passage and therefore enables to stabilize the insert at the level of this flare. Note also that in various embodiments, the abutment surfaces of the insertion stop (25) or withdrawal stop (20) of the insert (2) are not necessarily completely facing the anterior or posterior ends of the insert, but it is possible that they are inclined. For example, in these embodiments of stops in the shape of a thickening complementary to the flare, the stop surface is inclined with respect to the anterior and posterior ends, but the stop function is assured, in particular with another surface of the insert (e.g., the face of the insert opposite to that on which the stop in question is formed). Thus, in some embodiments, the stop surface may not be facing the ends of the insert, generally thanks to another surface of the insert, complementing this stop surface (for example a surface present on the face or edge of the insert opposite to the face or edge bearing the stop concerned.

In certain embodiments, at least the front (or anterior, that is the one inserted first) end of the insert can include at least one chamfer on at least one of the faces of the plate and/or on at least one of the edges of the plate. It is however generally preferred that the edges of the plate not be chamfered so that the entire width of the plate offers a supporting or retaining service for the lateral faces of the spinous process. It is therefore generally preferred not to reduce the dimensions of the plate by an edge chamfer. The chamfer on at least one face (for example, concave and/or convex) of the plate offers various advantages. A chamfer at the front end can facilitate the insertion of the insert into the passage and/or help the passage of the insert along the spinous process, particularly if tissues are adhering to the spinous process. It is also generally preferred that the insert not be too pointed to avoid the risk of injury to surrounding tissues. A chamfer can then be provided, but arranged so that the chamfered end does not form a cutting edge. A chamfer at the front end of the concave face of the curved plate, as can be seen for example in FIG. 1C, allows the end to offer a surface oriented substantially along the orientation of the lateral face of the spinous process along which it lies, while other parts of the insert do not have the same orientation due to the curvature of the insert. In the case of inserts both of whose ends are intended to lie along the spinous processes, the same type of chamfer can be provided at both ends. In addition, to avoid injury to the surrounding tissue, the ends of the insert can be provided with rounded edges, or at least arranged so that they don't form corners that are too sharp.

Advantageously, the insert (2) is retained within the body (10), and may even be attached to it. Stop mechanisms or retention resources (20, 25) are described in the present application as examples of insert retention (stop or attachment, fixation) mechanisms. Omitting such mechanism is considered, however, because in certain embodiments the insert (2) can be retained in the body by means of a thickened portion of the insert that comes into contact with the walls of the body passage so that the insert is forcibly inserted into the passage and is held there by friction. In fact, the insertion trajectory of the insert into the body is sufficiently different from the orientation along which the forces on the insert will be exerted that the insert may be retained in the body with no other specific means. Thus, upon being inserted into the body of the implant, the insert constitutes a means of retaining the implant between the spines, whether or not the insert itself has means for being retained within the implant. Likewise, instead of a thickening, it is possible for the insert to be retained within the body due to the fact that its curvature is so great compared to the dimensions of the passage that it must be forcibly inserted in the passage and is retained there by its own contact with the walls of the passage. A less flexible insert would then be preferred to avoid having it be too easily dislodged from the passage by deforming under the effect of forces. Nevertheless, to ensure good retention of the insert, various stop (i.e., retention) mechanisms including specific stop (i.e., retention) means or resources are also considered.

Figure 5A:
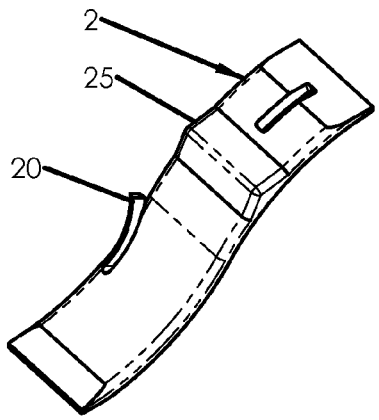
FIGS. 5A, 5C and 5E show perspective view of sigmoidal inserts intended to be retained within interspinous implants according to various embodiments, FIGS. 5B, 5D and 5F showing side views of the inserts of FIGS. 5A, 5C and 5E, respectively, FIG. 5G showing a view in profile of the insert of FIGS. 5E and 5F.
Figure 5B:
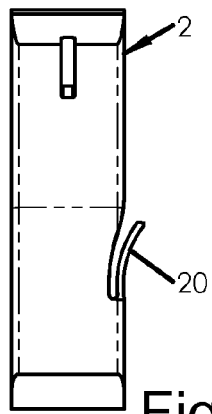
Figure 5C:
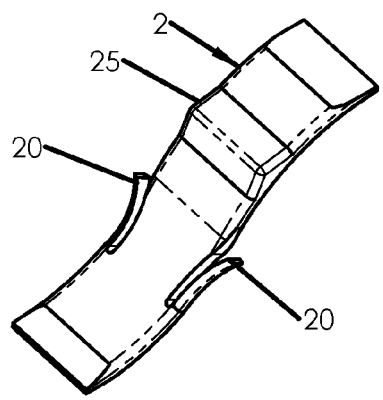
Figure 5D:
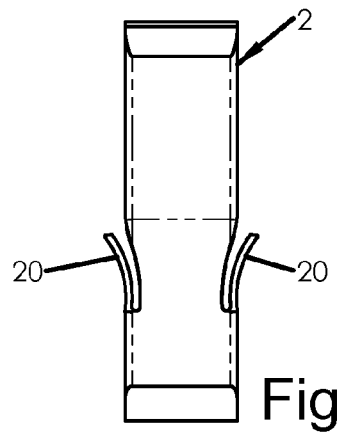
Figure 5E:
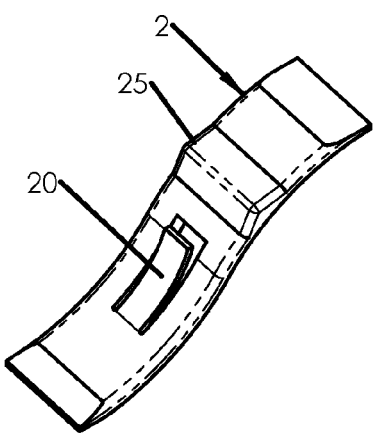
Figure 5F:
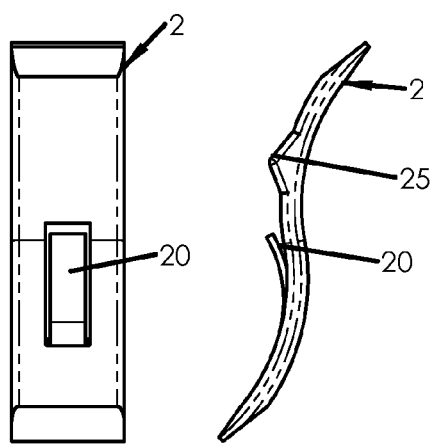
Figure 5G:
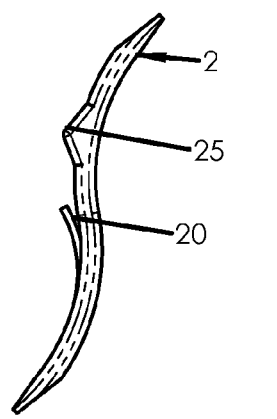
Figure 10A:
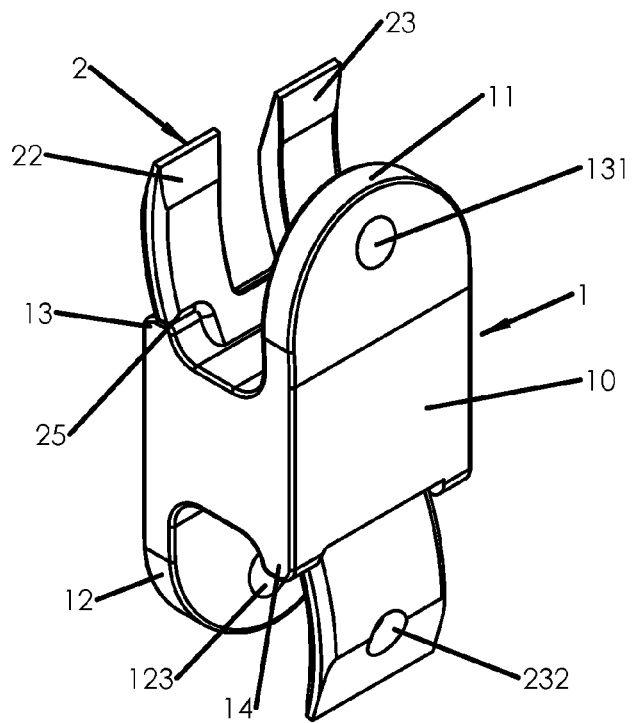
Figure 10B:
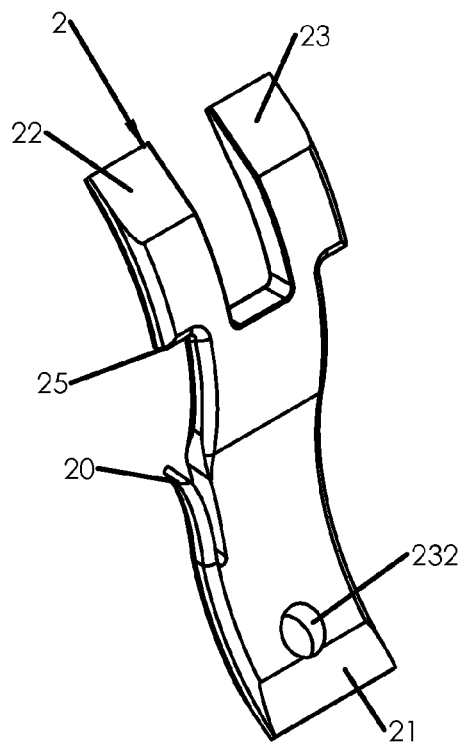
Figure 10C:
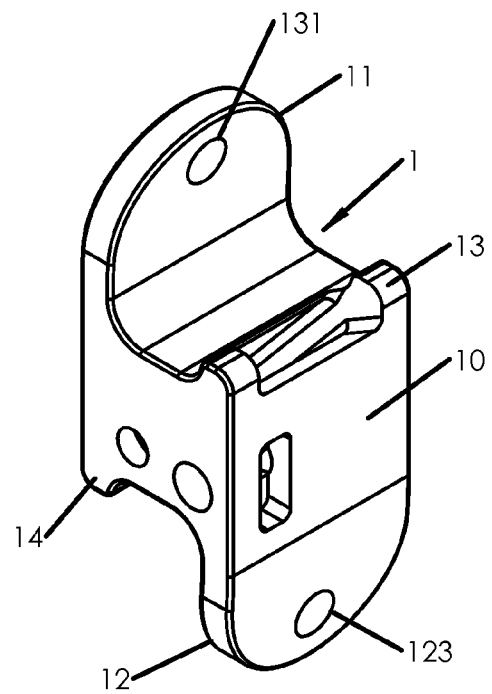

In certain embodiments, the stop mechanism includes at least one insertion stop (25) for the insert (2), located preferably on a back part of the insert (2) (near the back lateral face of the implant) and including an abutment surface facing preferably the anterior end of the insert to make contact with a complementary surface of the body (10) preferably facing the posterior end of the insert (2). The orientation of the abutment surfaces is not necessarily orthogonal to the antero-posterior direction of the insert, but it preferably will provide stable abutment to retain the insert (2) and avoid having it penetrate too far into the passage (15). The abutment surface of the body (10) will preferably be near the passage (15) to receive the insertion stop (25) of the insert (2), even inside the passage (15) if the insertion stop (25) of the insert is further forward than the posterior end of the insert (2). Thus insertion stops (25) are shown in the illustrative examples in FIGS. 1A through 1C in the form of tabs arranged at the posterior end of the insert (2). These tabs (25) are preferably bent back toward the inside of the curve of the insert (2) to provide a better abutment surface preventing the insert (2) from penetrating farther into the passage. Additional examples of insertion stops (25) are shown in the illustrative examples of FIGS. 5A, 5C, 5E and 5G in the form of an embossment or thickening of the insert. Various shapes can be considered for this embossment and the triangular-section shape that can be seen in particular in FIG. 5G is not limiting because it is understood that a correctly oriented abutment surface is sufficient to carry out the function. Likewise, in the illustrative examples of FIGS. 10A and 10B, the insertion stop (25) is obtained due to the fact that the insert (2) has a shoulder which will come into contact with the body at the entrance to the passage (around the passage). The possible variations for the shape of the insertion stop (25) can be understood from these various examples.

In certain embodiments the stop mechanism preferably includes at least one withdrawal stop (20), arranged to impede the withdrawal of the insert (2), in order to avoid having the insert leave the passage (15) unintentionally. Such a withdrawal stop (20) preferably does not impede the insertion of the insert (2) into the passage (15). In some embodiments, the withdrawal stop is preferably made up of at least one flexible tab (20) arranged, firstly, to be able to move from its rest position during the insertion of the insert (2) into the passage, so as to allow the movement of the insert (2) and, secondly, to return to its rest position so as to abut a complementary surface (122) when the insert reaches its final position within the body (10). The flexible tab is preferably provided on the insert (2) and oriented substantially in the direction of the posterior end of the insert (2), but it will be noted that it is also possible to provide at least one flexible tab on the body (10) instead of on the insert (2) and the tab will then be oriented in the direction of the anterior end of the insert (2) which will then include an abutment surface (122) to receive the end of the tab, for example with a shoulder provided at an appropriate distance from the ends of the insert (2). The tab preferably moves in the direction of the structure on which it is mounted (attached or built-in, in one piece or not) to allow the insertion of the insert. Preferably, it moves within a recess provided for the purpose so as not to extend out of the structure on which it is mounted. Thus for example, as can be seen in FIGS. 5A through 5D, the tab folds into a recess in the edges of the plate, so as not to project outside the width of the plate. Various withdrawal stop configurations, and in particular flexible tabs, are thus considered in the present invention. In certain embodiments, an example of which is illustrated in FIGS. 5A and 5B, the flexible tab (20) is located on a lateral edge of the plate constituting the insert (2). In other embodiments, an example of which is illustrated in FIGS. 5C and 5D, two flexible tabs (20) are located each on one lateral edge to provide symmetrical locking of the insert (2). In other embodiments, an example of which is illustrated in FIGS. 5E through 5G, a flexible tab (20) is arranged on one of the faces of the insert. It is possible moreover to select a tab on a concave or a convex part, but the concave surface is generally preferred to ensure better retention of the insert (2). Optionally, several withdrawal stops (20) can be provided on one or several faces and/or edges of the insert's plate and the body can be provided with several complementary stop surfaces (122) for receiving these withdrawal stops.

The use of a stop mechanism combining the insertion stop (25) and the withdrawal stop (20) is preferred, provided on the insert (2) at positions suited to simultaneous operation, so that the insert (2) engages the insertion stop and the withdrawal stop at the same time once it is inserted far enough into the implant to extend to the desired part of the lateral faces of the spinous processes. Thus, the flexible tabs forming the withdrawal stop (20) of the insert (2) will preferably be oriented in the direction of the insertion stop (25).

In certain embodiments, the insert (2) can include at least one means of retaining the insert, designed to receive a tool allowing a pull to be exerted on the insert (2) in order to disengage it from the passage (15), for example when it is desired to withdraw the implant. For example, as shown in the illustrative examples of tabs in FIGS. 1A, 1C, 2A and 2C, a recess is provided on the tabs (25) constituting the stop to receive a tool. By inserting the end of a tool into this recess, the insert can be pulled on to withdraw it. It will be noted that other gripping means than a recess can be provided, and a male structure instead of a female structure in particular. In addition, these means of gripping the insert can be provided on the stop (25) or at various places on the insert, preferably accessible on the back lateral face of the implant, according to various possible embodiments. For example, other types of inserts (2) are shown in FIGS. 13A, 13B and 13C which also include such retention means, such as ring (26), at the posterior end of the insert (2). This retention means (26), made up in this example of a cylindrical recess provided on at least part of the width of the insert to allow good retention of the insert (2), can be used for removal of the insert (2), but also during implantation of the insert to facilitate the entry of the insert (2) into the passage, as detailed in the present application.

Figure 12A:
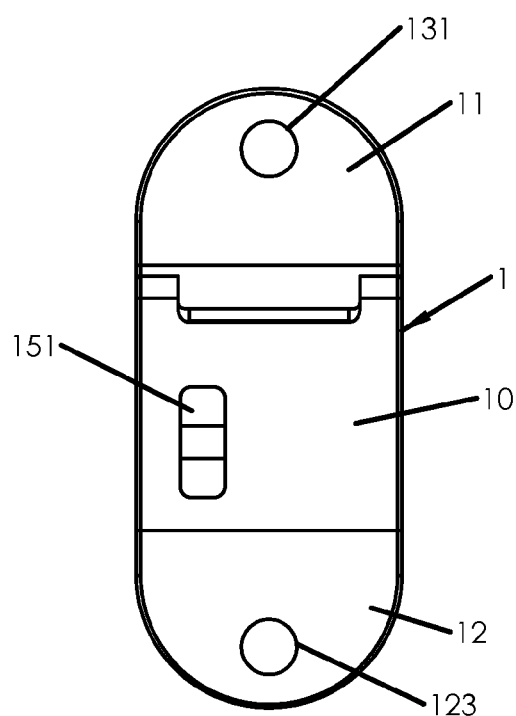
FIGS. 12A, 12B and 12C show a side view, a top transparency view and a longitudinal section view, respectively, of an interspinous implant according to certain embodiments.
Figure 12B:
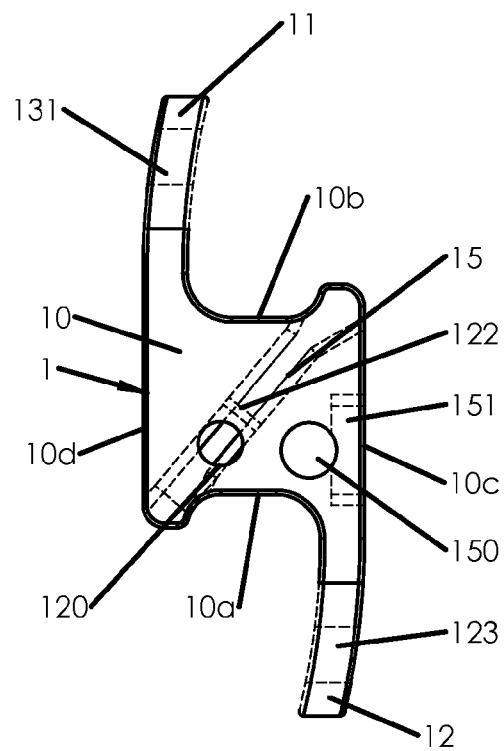

As mentioned previously, in certain cases it is desirable to be able to withdraw the insert (2) and a gripping means can be provided for withdrawal, but in the case where the insert also includes a withdrawal stop, as for example flexible tabs, a means for disengaging the withdrawal stop is then provided. Flexible tabs (20) are particularly advantageous for that because they can be moved in order to allow the insert to back down the passage. In the case where the flexible tab is so arranged that the withdrawal stop is accomplished within the passage, an access duct (120) to the flexible tab is provided in the body. On the other hand, in certain embodiments, the flexible tab (20) is arranged outside the passage (whether on the insert or on the body) and is therefore directly accessible to be disengaged from its complementary surface in order to allow removal of the insert. It should be noted here that the stop surface (122) arranged to receive (complementary to) the flexible tab (20) can be formed by the walls of the access conduit (120) or by a surface specifically provided elsewhere in or on the body (10) of the implant. For example, in FIGS. 8C and 12B are shown by transparence the stop surface (122) which does not coincide with the walls of the access conduit (120). It will be understood that the access conduit allow one to press on the tab (20) but that the abutment of the latter will occur at the surface (122) which is inside the passage shown in these figures. However, it will be understood that it is simply possible that the access conduit or housing forms itself, by its walls, a stop surface that can accommodate the free end of the flexible tab which can then be directly operated to be disengaged. Indeed, for example as shown in FIGS. 18A, 18B and 18C, and also on FIGS. 19A, 19B and 19C, the access recess or conduit (120) may be arranged so that at least one of its walls forms the stop surface (122). Hence, the free end (the one used as a stop surface) of the flexible lug (20) can directly abut a wall (122) of the conduit or other retainer structure disposed in or along the access conduit (120). One can thus directly access the free end of the flexible lug (20) to disengage it from its stop (122).

Moreover, the complementary abutment surface (122) for receiving the tab (20) is preferably provided in the walls of the passage, but it can be near the passage (15), that is at the entry or the outlet of the passage, as for example and preferably a surface at the entry to the passage. The access duct (120) can then be an indentation running along the passage (15) and accessible at the entry to the passage. A stop mechanism located in the passage (15) is generally preferred, or at least an indentation near the passage (15), to avoid having the flexible tab (20) disengage unintentionally, and an access duct (120) will then preferably be arranged in the body (10) as shown for example in FIGS. 4A through 4D, 6A through 6F, 7A through 7D or 8A through 8C. This access duct (120), and hence the tab (20), as well as the surface complementary to it, will preferably be arranged to be easily accessible, by adjusting their positions and/or their orientations so that the tab can be actuated, preferably from a lateral or posterior or oblique approach to the vertebral column.

Figure 1A:
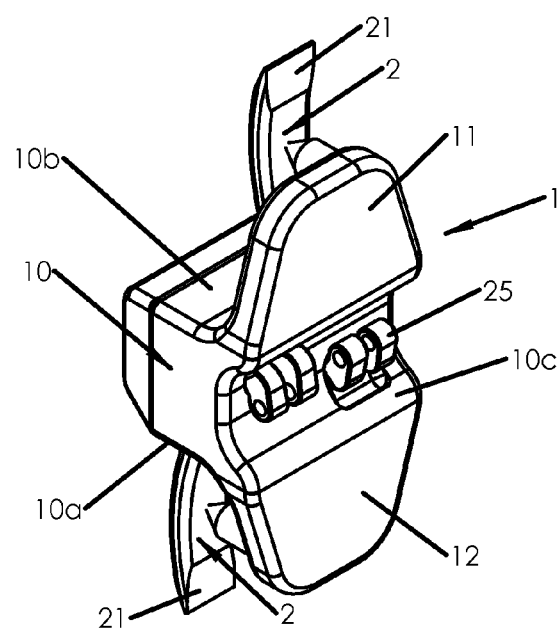
FIGS. 1A, 1B and 1C show respectively a perspective view, a side view and a top view of an interspinous implant according to certain embodiments.
Figure 1B:
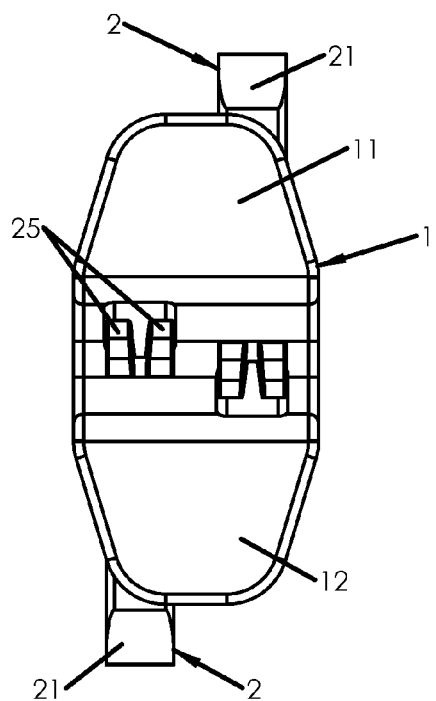
Figure 1C:
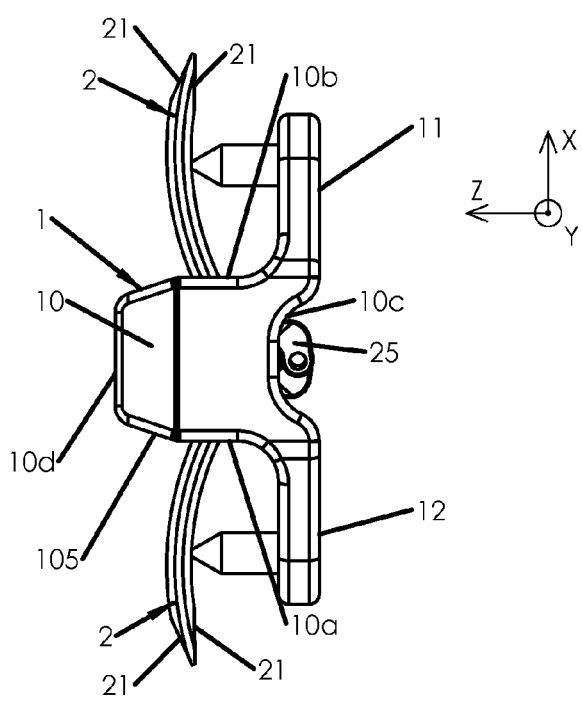

For the embodiments illustrated for example in FIGS. 1A and 1C, the body (10) includes a lower face (10a) and an upper face (10b). These upper and lower faces are arranged to come into contact with, respectively, the upper edge (E2) of the lower spinous process (EI) and the lower edge (E3) of the upper spinous process (ES), as can be seen in particular in FIGS. 17A through 17C. Thus, depending on the dimensions and possibly the shape selected for the body (10), and particularly the height of the body, that is the distance between its lower (10a) and upper (10b) faces, the interspinous space can be maintained or increased, for example to restore it to a physiological value when it had been reduced to a pathological value. It is understood that these considerations of upper and lower faces and of implant height are applicable to all the embodiments detailed in the present application. In these embodiments, contact of the adjacent edges (E2, E3) of the two spinous processes (EI, ES) with the upper (10b) and lower (10a) surfaces of the implant occurs on at least a part of these surfaces (10a, 10b). The spacing of these two spinous processes (EI, ES) obtained by the insertion of the implant between the adjacent edges (E2, E3) of the two spinous processes is therefore determined by the distance between these two parts where contact takes place. It will be noted that, in certain embodiments, particularly those where compression of the spinous processes is provided for by a pivoting motion of the insert or pivoting of two inserts relative to one another, or even pivoting of different parts and portions of the retainers (as detailed later in the present application, for example with reference to FIGS. 43A, 43B and 43C), contact with a spinous process can occur both on a part of one of the surfaces, lower (10a) or upper (10b), of the body (10) and on part of one of the concave surfaces of the insert (2). Body dimensions (distance between the lower and upper surfaces of the body) and an arrangement of the implant (position of the insert passage and positioning of the insert in the body) are then provided that allow the desired spacing between the spinous processes.

In certain embodiments, examples of which are illustrated in FIGS. 1A through 1C and 2A through 2C, the interspinous implant (1) includes two wings (11, 12) arranged on a single lateral face of the implant (1) so as to each lie along only one of the two spinous processes (EI, ES), on the same lateral face (E4, E5) as the other wing. This implant includes two passages (15) provided in the body (10) for the insertion of two inserts (2) each projecting toward one of the spinous processes (EI, ES) to both lie along the same lateral face (E5, E4) which is opposite that which the wings lie along. These two inserts (2) therefore constitute said at least one retainer of the implant, supplementing the two wings. The passages (15) are accessible for insertion of the inserts (2) in the same lateral face as the wings (11, 12) so that the implantation between the spinous processes (EI, ES) can be performed from a single one of their lateral faces (E4, E5). In these embodiments, the implant (1) preferably has substantially a T shape, the vertical branch of which is formed by the body (10), with the horizontal branches of the T being made up of two wings (11, 12) arranged on the same lateral face (10c) of the implant (1) to lie along the same lateral faces (E4, E5) of the spinous processes (EI, ES). The two passages (15) being arranged to receive the insert (2) on the same lateral face as the two wings, they are preferably arranged in an indentation of this lateral face (10c) between the two wings (11, 12), to allow for a stop (25) of each insert (2) remaining at the entry to the passages (15) not extend beyond the width of the body (10), as can be seen particularly in FIGS. 1C and 2C. In these embodiments, the inserts (2) preferably include at least one plate of which at least a part is curved. Preferably, the insert (2) has the shape of a curved plate having a radius of curvature on at least its longitudinal axis.

Preferably, one of the two passages is arranged to pass through a part of the body from a lateral face (10c) toward the upper face (10b) of the body (10) and the other passage is arranged to pass through a part of the body (10) from the same lateral face (10c) toward the lower face (10a).

The two passages (15) are preferably side by side, that is located a distance from one another along the Y direction, but they can be stacked, that is located a distance from one another along the X direction. If they are stacked, given the curvature of the insert (2), if it is desired that both inserts (2) be able to be inserted at the same time (by a single manipulation, for example using an appropriate instrument), they must be sufficiently separated depending on the radius of curvature, while when they are side by side, the 2 inserts (2) can be inserted at the same time regardless of their curvature and of the spacing between the two passages (15). Nevertheless it is possible to insert the two inserts (2) in succession without that resulting in too great an inconvenience, in particular thanks to the stability of the implant provided by the first insert (2) which would have already been put in place. In addition, as indicated previously, as the inserts (2) can be provided with a means of retention, it will be easy to insert them, even in succession. It will also be noted that it is possible to provide a single duct, for example with the two passages (15) for these two inserts (2) forming a common duct separating into two divergent channels to guide each of the inserts toward one of the two spines, whether the two passages are one above the other or side-by-side. Further, it is also possible to provide inserts with a curved plate that is separated into two branches (e.g., 253, 254; FIG. 42B), at least on a posterior portion of the curved plate, such that the two inserts can be nested inside one another and inserted at the same time. Thus, one branch of each insert passes between the two branches of the other insert and the two inserts can follow their opposite trajectories at the same time without interfering with one another. An example of such a two-branched insert is described in more detail in the present application, but only in certain embodiments where the two inserts are pivoting about a common hinge (a common articulation pin) shown in FIGS. 42A, 42B and 42C. However, it will be understood here that it is possible to provide two-branched inserts which are not assembled on a common axis and which simply have two branches (253, 254) allowing them to be nested together so that they can be inserted at the same time. In addition, it will be understood from the detailed description hereafter of the inserts having a common hinge that it is possible to also use such inserts having a common hinge in implant embodiments such as those shown in FIGS. 1A through 1C and 2A through 2C. Preferably, the hinge will not extend beyond the two inserts so as to be able to penetrate into the passage and the inserts will be provided with stop arrangements (preferably at least one withdrawal stop) to avoid having them come back out of the passage (15) in the implant. On the other hand, an insertion stop is not necessarily required because at least one wall of the passage will provide a stop for the common hinge and/or the nesting of the inserts of the branches, thus making it possible to avoid having the latter penetrate too deeply into the passages (15). In the case of two nested inserts without a common hinge, it is preferably provided that the two branches do not join at the posterior end of the inserts, to allow each of them to be pushed into the passage all the way without projecting too far from the surface of the implant (this also facilitates the manufacture of the inserts since they would have to be in two parts to be able to be assembled by nesting them one in the other if the branches of each of them were joined).

In certain embodiments where the body includes two passages (15) for receiving two curved inserts (2) inserted in succession, the two inserts (2), and possibly the body (10) are designed so that the insertion stop (25) of a first insert (2) having a withdrawal stop (20) extend to the second insert (2) to constitute a withdrawal stop (20) for this second insert (2). The insertion stop (25) therefore makes it possible to stop the insertion of the second insert but also extends to bear on a portion of the second insert (2). The first insert (2) which includes a withdrawal stop (20) preventing it from withdrawing from its passage, provides due to its insertion stop (25) a withdrawal stop preventing the second insert from withdrawing from its passage (15). In addition, in certain of these embodiments, the withdrawal stop (20) of the first insert is designed to bear on the second insert (instead of bearing on the body of the implant).

In certain embodiments, in particular those where the implant (1) includes two wings on the same lateral face, the body preferably, but without limitation, includes on its anterior part (intended to be inserted first), at least one chamfer (105) to facilitate its insertion into the interspinous space (particularly through the interspinous ligament). For example, as can be seen particularly in FIGS. 1A, 2A, 1C and 2C, the body can be provided with chamfers (105) at the anterior end of the upper and lower faces, but also of the faces arranged in the directions forward and rearward of the patient. Thus, the lateral anterior part of the body (referred to the direction of insertion) has smaller dimensions than the rest of the body to facilitate its insertion between the upper edge (E2) of the lower spinous process (EI) and the lower edge (E3) of the upper spinous process (ES).

Figure 3A:
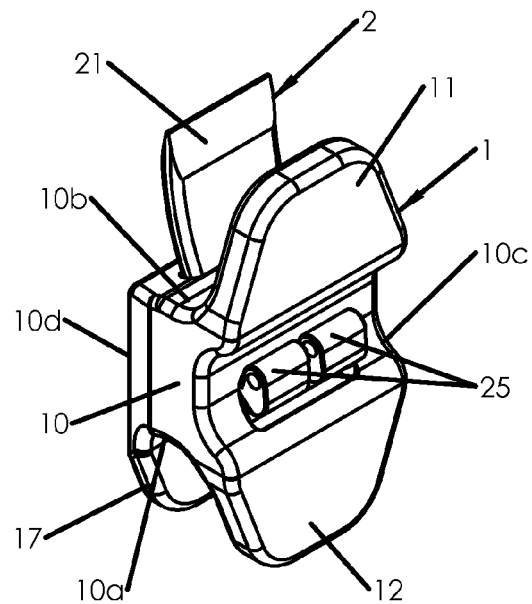
FIGS. 3A, 3B and 3C show respectively a perspective view, a side view and a top view of an interspinous implant according to certain embodiments.
Figure 3B:
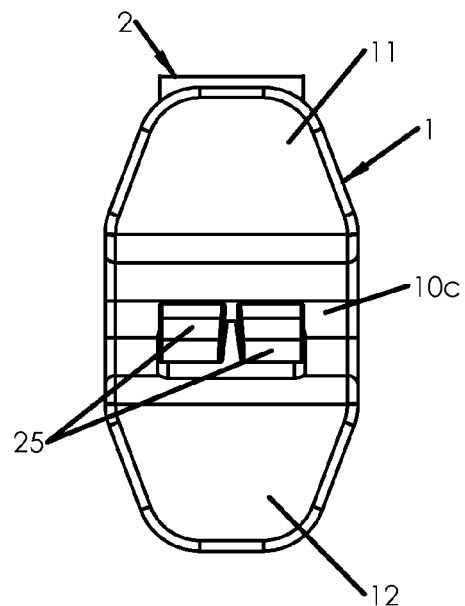
Figure 3C:
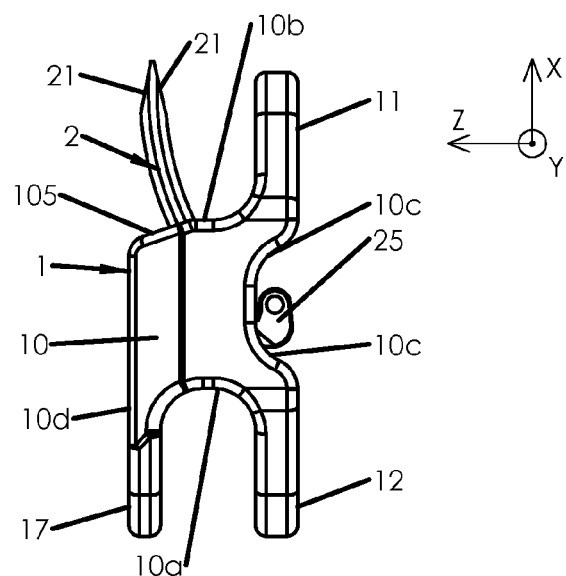

In certain embodiments, an example of which is illustrated in FIGS. 3A through 3C, the body (10) includes two wings (11, 12) arranged on the same back lateral face (10c) of the implant (1) to lie each along one of the two spinous processes, but on the same back lateral face (E4, E5), and a third wing (17) arranged on the front lateral face (10d) (the opposite face), to lie along the front lateral face (E5, E4) of a first of the two spinous processes (EI, ES). Said at least one retainer can then include a curved insert supplementing these three wings in the function of retaining the implant. Indeed, a passage (15) is then provided in the body (10) for the insertion of an insert (2) projecting toward the second spinous process (ES, E1), so that this insert (2) lies along the same lateral face (E5, E4) as the third wing (17) (but f the second spinous process while the third wing lies along the first spinous process). This passage (15) is accessible for insertion of the insert (2) on the back lateral face (10c) of the implant equipped with the three wings (11, 12, 17), so that the implantation between the spinous processes (EI, ES) can be performable from a single one of their lateral faces (E4, E5). In these embodiments, a chamfer is preferably arranged on the upper (10b) or lower (10a) face equipped with a single wing (on the lateral face having only one wing), so as to facilitate the insertion of the implant into the interspinous space. In addition, these embodiments are better suited to cases where it is desired to allow a certain amount of lateral play to the implant thanks to sufficient spacing between one of the wings (12) and the third wing (17). It is then possible to have a spacing between the wing (11) and the insert (2) which allows or does not allow play because the insertion of the insert (2) imposes less constraint on the implantation, while the insertion of the upper or lower part of the implant (depending on the orientation given) equipped with the third wing is more awkward, particularly if the height of the implant is selected so as to restore an interspinous space height greater than the value that it has before the implantation. It is therefore understood that the embodiments where said at least one retainer include(s) two curved inserts are preferred over those where the implant includes three wings and where the retainer includes a curved insert, particularly if no other retainer arrangement supplements this curved insert. Indeed, here the implant must, in order to be easy to implant, have a space between the third wing and its counterpart which does not ensure optimal support along the Z axis. Other arrangements, or at least combining this embodiment with other retainers, will therefore be preferred, as for example a ligament (L) or a bone anchorage means, the advantages whereof are detailed in the following. Likewise, rather than the embodiments whose body has three wings, the embodiments described in the following will also be preferred, in which the body has only two wings, of which one wing lies along a lateral face of a spine and the other lies along the opposite face of the other spine.

In certain embodiments, examples of which are illustrated in FIGS. 4A through 4D, 6A through 6F, 7A through 7D, 8A through 8C, 9A and 9B, 10A and 10C, 11A and 11B, 12A through 12C, 13A through 13C, 14A, 15A, 15B and 17A through 17C, the body includes two wings (11, 12) each arranged on one lateral face (E4, E5) opposite the other wing (12, 11) and each projecting toward one of the two spinous processes, so that the wings each lie along a spinous process (EI, ES) but on opposite lateral faces (E4, E5). Thus, a first wing lies along a first spinous process on one lateral face and another wing lies along a second spinous process, on the opposite lateral face. These are particularly advantageous embodiments, particularly due to their ease of implantation and the simplicity of their shape, and they are used with various types of retainer as detailed in the present description. In certain of these particularly advantageous embodiments, it is possible to use only a single insert (2) as a retainer. This has the advantages of reducing the number of parts (which reduces costs and the number of parts which might possibly migrate within the interspinous space or its edges), facilitating the manufacture of the body (which has only one passage instead of two) and being able, for the same body size, to provide a larger insert (particularly in thickness) to as to be more robust (than in the case where two inserts have to be run into a body). Further, the fact that the two wings are on opposite faces of the insert allow one wing to be on the face opposite to that by which the vertebral column is possibly approached for implantation, which can be an advantage in terms of the stability of the implant, but the implant is mainly easier to implant even if the spinous processes must be spread apart. Indeed, the implant can be used to restore sufficient interspinous spacing as explained previously. In this case, the fact that the insert has its two wings on opposite faces means that one wing is inserted first to make the body pivot until the two wings lie along the spinous processes. Thus, in the case of a very tight interspinous space, the body and the first inserted wing can serve as spreaders for separating the two spinous processes and forcing the insertion of the body between the two spinous processes. In the three-wings embodiments, this passage will be even more difficult and in the two-wings embodiments where the two wings are on the same face, it is the body which is inserted first and the chamfer, if any, at the front will not necessarily be sufficient to allow the front of the body to be inserted and to progressively spread apart the two spinous processes. However, if the two spinous processes are closer from each other than the height of the body at these chamfers, these embodiments will prove especially effective.

Figure 12C:
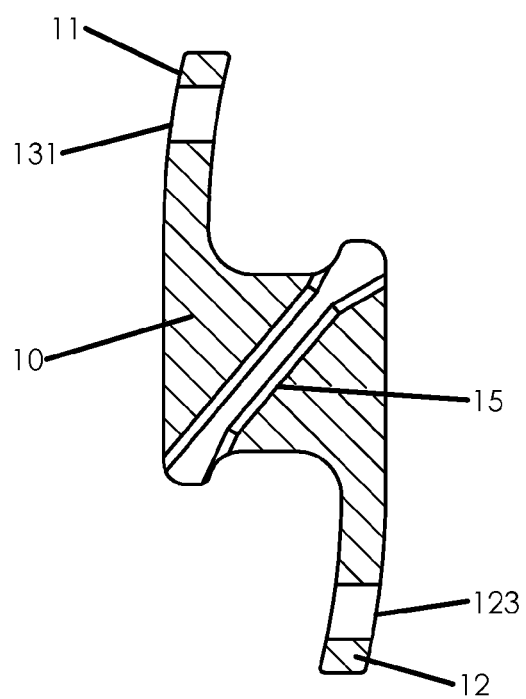

In the case of these implants with two opposite wings wherein the retainer includes an insert, this insert (2) includes two curves of opposite orientations. This insert (2) is then generally of substantially sigmoidal shape due to the fact that its plate includes at least two radii of curvature of opposite orientations, so that two faces of the plate each have a concave part and a convex part. The passage (15) and the insert (2) are then arranged so that, when the insert (2) is lodged in the passage (15), at least a part of said convex parts of the two faces of the insert (2) each lies along at least a part of the spinous processes (EI, ES), on lateral faces (E5, E4) opposite to those along which the wings lie (11, 12). The insert (2) is then still inserted along a single back lateral face (10c) of the implant (1) while still obtaining good retention on the two lateral faces (E4, E5) of the spinous processes (EI, ES). The insertion of the insert is therefore performed along an axis that is more parallel to the vertebral column than in the other embodiments, but generally without thereby causing a problem of bulk since the axis lies substantially along a lateral face of the spinous processes. The illustrative examples in FIGS. 12A, 12B and 12C illustrate the shape of the passage (15) in which the sigmoidal-shaped insert (2) is inserted and shows examples of anchorage means (150, 151) arranged for grasping the body (10) using an instrument as explained in the present application.

In certain embodiments, the insert (2), whether having a single curve or two curves of opposite orientation as described in the present application, has at least one rib to stiffen it. This rib (not shown) is preferably on at least a portion of the convex face of the insert (2), such that it is not set facing or in contact with lateral faces of the spinous processes. In such embodiments of the insert, the passage (15) for the insert (2) in the body (10) of the implant includes at least one groove arranged to receive this rib on the insert (2). A stiffened insert (2) is thus obtained which is stably held within the body due to the complementary shape of its rib and the groove present in one of the walls of the passage in the body.

In certain of these embodiments having two opposed wings and a sigmoidal insert, the implant then includes at least one ridge (13, 14) on at least one of its lower (10a) and upper (10b) faces, preferably near or at the junction with the lateral faces not having wings (11, 12). Such a ridge (13, 14) impedes the implant (1) from disengaging from the space between the adjacent edges (E2, E3) of the two spinous processes (EI, ES). The ridge can have the shape of a shoulder, preferably slightly rounded, or any other shape giving greater height to the implant at the shoulder than between the lower and upper faces, so that the implant will be impeded by the ridge if it were to slip between the two spinous processes before the insertion of the insert (2). The ridge (13, 14) is preferably chamfered or rounded on its part located toward a lateral face of the implant (1), so as to facilitate the insertion of the body (10) between the adjacent edges (E2, E3) of the two spinous processes (EI, ES). It will be noted that such a ridge can also be provided in the embodiments where the wings are on the same lateral face and examples of which are shown in FIGS. 1A through 1C and 2A through 2C, even though these examples do not show such a ridge. However, a ridge will preferably be provided on only one of the upper (10b) or lower (10a) faces so as not to hinder the insertion of the implant (1). A possible chamfer (105) on the lower (10a) or upper (10b) face other than that provided with a ridge will then facilitate the insertion of the implant (particularly by allow it to be slightly tilted to allow the ridge to pass into the interspinous space). On the other hand, in embodiments equipped with three wings, it will be preferable not to provide a ridge on the upper (10b) or lower (10a) face provided with only a single wing, so as not to impede the insertion of the implant (1) into the interspinous space.

Figure 9A:
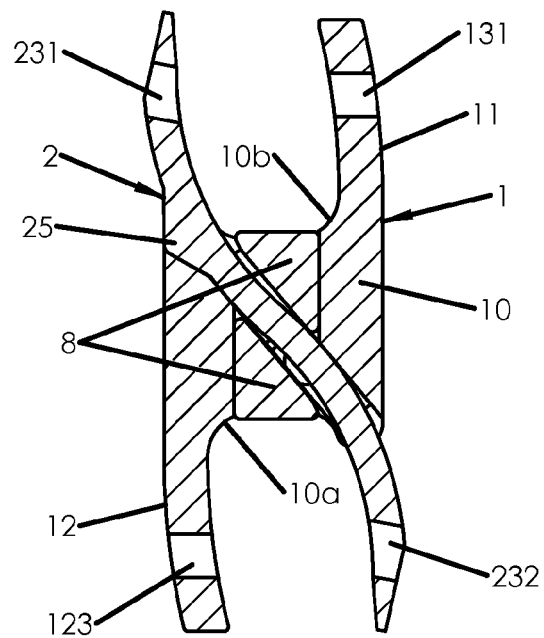
FIGS. 9A and 9B show longitudinal section views of interspinous implants according to various embodiments.

In certain particularly advantageous embodiments, an example of which is illustrated in FIG. 9A, the body (10) includes, at least on its upper (10b) and lower (10a) faces in contact with the adjacent edges (E2, E3) of the two spinous processes (EI, ES), at least one material (8) favoring bone growth to allow the fusion of the upper (ES) and lower (EI) spinous processes. The bone-growth-favoring material (8) can for instance be bone, such as a graft or any other substitute. Preferably, the bone-growth-favoring material (8) is not simply arranged on the upper and lower faces of the body, but instead is arranged so as to provide continuity allowing fusion of the two spinous processes. Thus the body preferably has a central hollow or duct, substantially cylindrical or honeycombed, for example, running across the body (10) from side to side between the upper and lower faces (10a, 10b) in contact with the adjacent edges (E2, E3) of the two spinous processes (EI, ES). This duct filled with bone-growth-favoring material (8) then provides continuity allowing bone growth through the implant and allows the upper (ES) and lower (EI) spinous processes to fuse together. As the bone growth trajectory through the body crosses the insert (2), as can be seen particularly in FIG. 9A, a passage (not shown) will preferably be provided in the insert to allow bone growth through the insert and/or the duct will be larger than the insert (2) and the passage (15) to provide room on either side of the passage so that bone growth can occur, respectively, through and/or around the insert. For example, it can be arranged that the duct that crosses the body between its upper and lower faces receives bone graft material or a substitute to allow the bone tissue of the spinous processes to grow through the implant, for example by inserting the insert through the graft or substitute. Preferably, these embodiments providing for the addition of a bone-growth-favoring material (8) will use means for bone anchorage of the wings and/or the insert into the spinous processes, as detailed in the present application, so as to immobilize the spinous processes and thus facilitate spinal fusion.

Figure 9B:
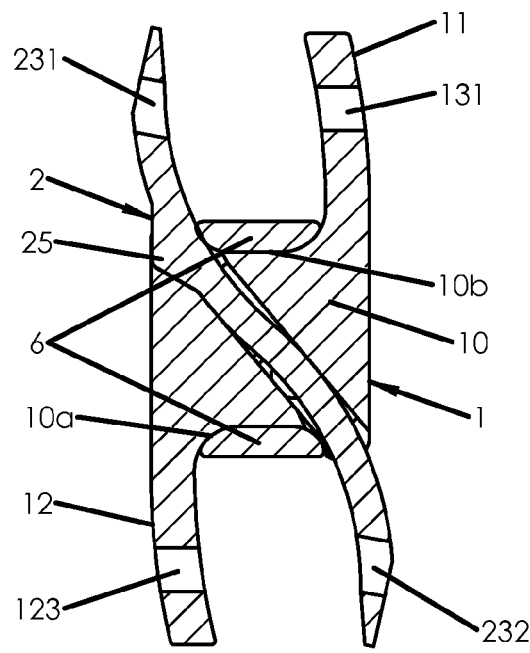

In certain particularly advantageous embodiments, an example of which is illustrated in FIG. 9B, the implant includes at least one cushion (6), which may be made of various types of cushioning, (dampening, flexible) material (6), on at least one of its upper (10*b*) and lower (10*a*) faces in contact with the adjacent edges (E2, E3) of the two spinous processes (EI, ES), so as to cushion the longitudinal (vertical) motions of the dorsal spinous processes (EI, ES). Generally, fusion of the spinous processes is accompanied by fusion of the vertebral bodies (for example with an interbody cage in addition to the interspinous implant) and/or sometimes the joints (articular processes). All embodiments described are preferably designed to stabilize the movement of spinous process, whether for purposes of fusing or not. The embodiments with dampening/cushioning and/or play are usually aiming at a flexible and controlled maintenance (that is to say, do not impose excessive constraints on the spinous processes), but are not exclusive from embodiments allowing a fusion (by bone anchor and/or bone growth material). Thus, in the embodiments with a damping/cushioning and/or play, one might want a mobility or a damping, for example with the damping material (6) to facilitate the implementation, while providing a lock with bone anchorage resources though. Thus, for example, the flexible material (6) may help compress the implant during installation, waiting to fix the compressed ensemble by means of anchoring resources. This flexible material (6) therefore generally offers a flexible interface between the implant and the spinous processes, allowing the implant to be more readily welcomed into the interspinous space.

In certain particularly advantageous embodiments, the implant (1) is suited to multi-level surgery, that is to the implantation of several implants between several consecutive spinous processes, each within an interspinous space. For example, in certain embodiments, at least one of the wings (11, 12) and/or at least one insert (2) is (are) arranged with shapes and/or dimensions designed so that two implants (1) can be implanted in at least two consecutive interspinous spaces of three adjacent vertebrae, with or without overlap of the wings (11, 12) or the inserts (2), but preferably without any overlap so as to avoid a reciprocal damage of the insert and wings. Thus for example, in various embodiments, the length of the insert (2) or inserts (2) can be arranged to extend farther than, less far than, or as far as the wings (11, 12) extend along the lateral faces (E4, E5) of the spinous processes (EI, ES). For example in the illustration in FIG. 1C, the two inserts (2) extend farther than the wings (along the longitudinal X axis of the vertebral column), while in the illustration in FIG. 2C the inserts do not extend farther than the wings. It will be understood that with a configuration such as that in FIG. 1C, by implanting, firstly, in a first interspinous space an implant such as that of FIG. 1C through a lateral face, according to the orientation shown in FIG. 1C and secondly, in an interspinous space adjacent to the first, a second implant with the same configuration, but via the opposite lateral face (hence with an orientation that is inverted with respect to that of FIG. 1C), inasmuch as the dimensions of the wings and the inserts are correctly matched to those of the lateral faces of the spinous processes, a succession of two implants is obtained which do not overlap and which are therefore suited to this multi-level surgery, while still affording good retention around the two consecutive interspinous spaces. Thus, each of the interspinous spaces will receive an implant from a lateral face opposite the one from which the implants of adjacent interspinous spaces will have been inserted, forcing to make incisions on both sides on the spinous process, but for different inter-spinous implants. Moreover, the absence of overlap can be obtained without reducing the length of the wings (11, 12). For example, the wings (11, 12) and the inserts (2) can have shapes arranged so as to be mutually complementary so that the wings and/or inserts of two implants can be arranged about the same dorsal spinous process (EI, ES). The illustrative examples in FIGS. 13*a*, 13*b* and 13*c* show for example two identical interspinous implants having complementarities of shape for multi-level surgery. In these examples, the lower part of a first implant (1) and the upper part of a second implant (1) are arranged to surround in a complementary manner the same dorsal spine (EI, ES). In this example, the upper end of a wing of the second implant (1) (on the front lateral face) has an indentation a notch or a cutting, for example in a U shape, in the sagittal plane, capable of receiving a lower end of the sigmoid insert (2) of the first implant (1). Moreover, a lower end of a wing (12) of the first implant (1) has (on the back lateral face) a cutaway giving for example this end a substantially L-shaped curve in the sagittal plane, capable of receiving the upper end of the complementarily-shaped insert (2) of the second implant (2), provided in particular with a retention means (26) deployed as a ring in this example. It is understood from these illustrative examples that implants can be provided that are intended to be implanted in the same mediolateral direction or in opposite directions, with male or female shapes at the ends of their wings (11, 12) and inserts (2) to make it possible to receive the ends of the wings and inserts of another implant implanted in an adjacent interspinous space. Likewise, in the illustrative example shown in FIGS. 10A through 11A, the sigmoid insert (2) has an indentation (or a notch or a cut) at one end, splitting the curved plate into two branches (22, 23), giving the insert a Y shape. In this example, the wings are not represented as being complementary to this type of insert, but it is possible to provide a complementary arrangement to allow multi-level surgery. However, this example is shown here rather for illustrating another aspect relating to bone anchorage in the spinous processes.

Figure 2A:
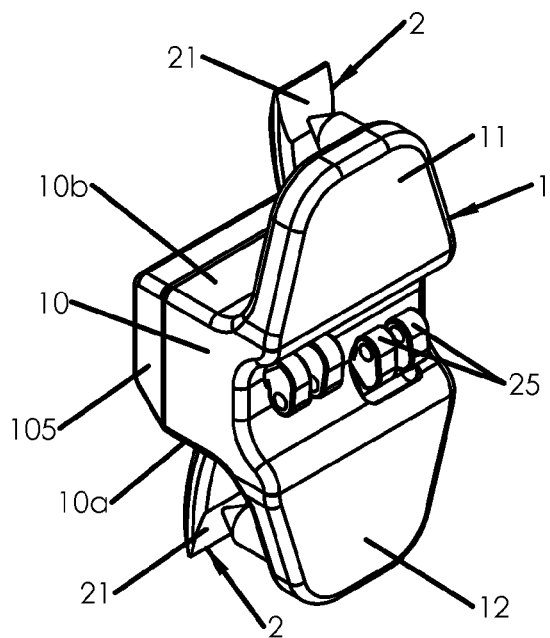
FIGS. 2A, 2B and 2C show respectively a perspective view, a side view and a top view of an interspinous implant according to certain embodiments.
Figure 2B:
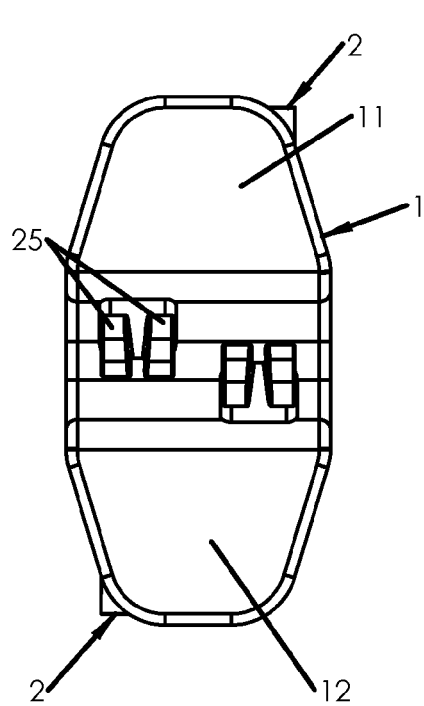
Figure 2C:
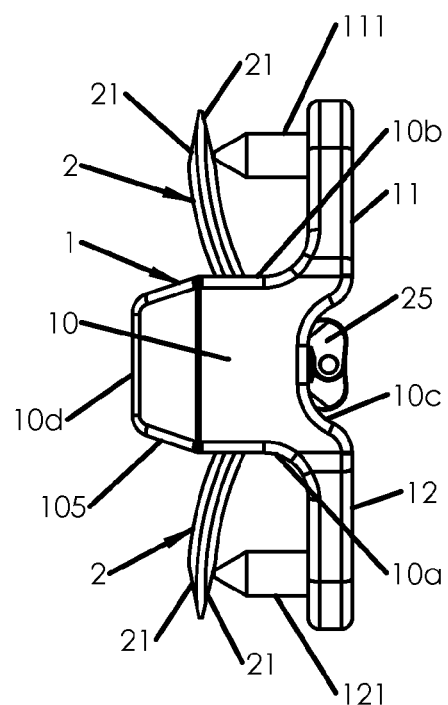
Figure 4A:
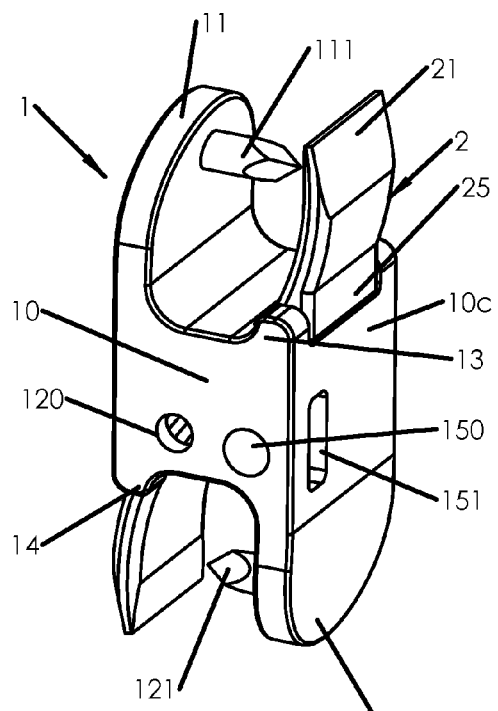
FIGS. 4A and 4B show respectively a perspective view and a top view of an interspinous implant according to some embodiments, FIGS. 4C and 4D showing respectively a perspective view and a top view of an interspinous implant and of an insert according to certain embodiments.
Figure 4B:
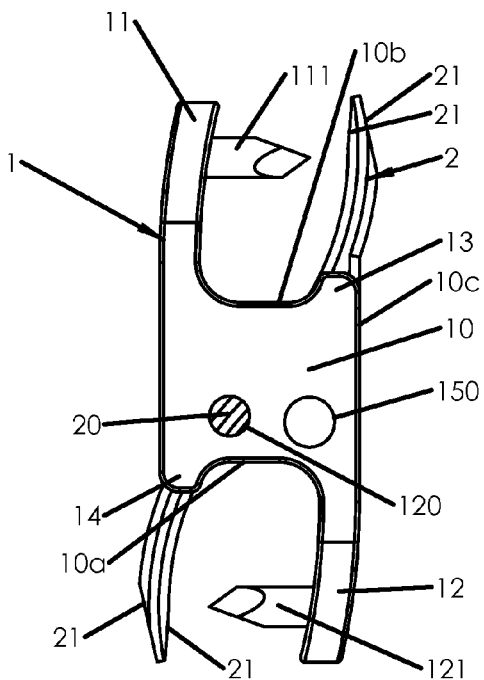
Figure 4C:
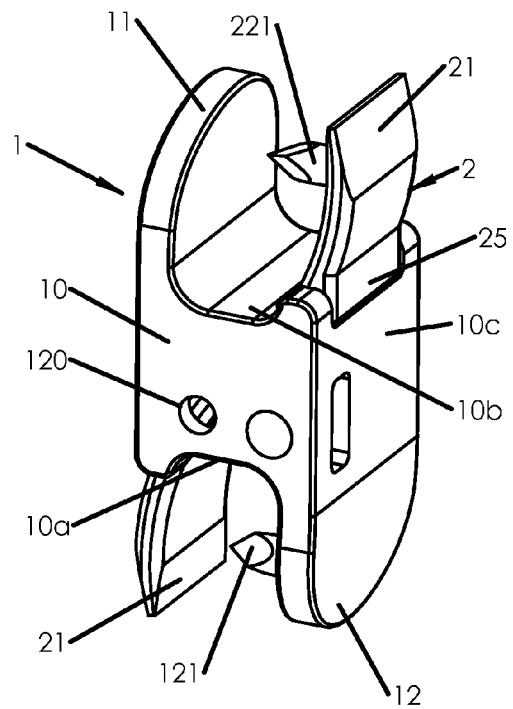
Figure 4D:
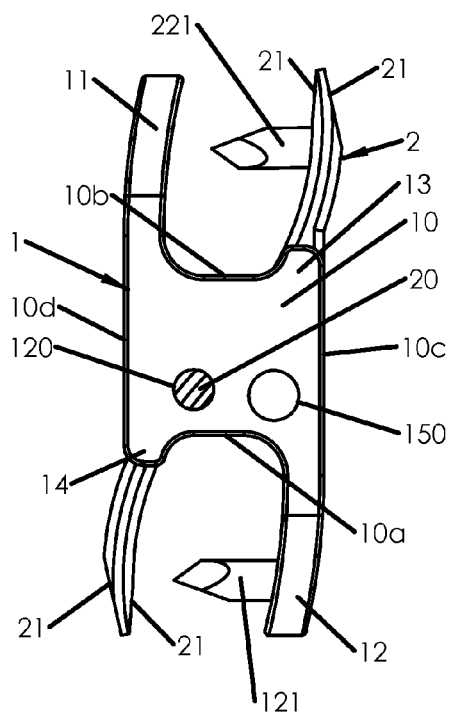

Indeed, in certain particularly advantageous embodiments, used particularly when fusion of the two spinous processes (EI, ES) is desired, or at least when a further stabilization is desired, the retainer of the implant includes bone anchorage means (3, 111, 121, 221, 7, 28) arranged so as to anchor the implant in the spinous processes. These bone anchorage means favor the retention of the implant relative to the spinous processes, but also allow the spinous processes to be held relative to one another, which provides supplementary stabilization (and even permits fusion of the two spinous processes). These anchorage means make it possible to anchor the implant, for example at the level of the wings (11, 12) and/or the inserts (2), in at least one of the lateral faces (E4, E5) of at least one of the spinous processes (EI, ES). For example, in certain embodiments, at least one wing (11, 12) of the implant (1) includes at least one point (111, 121) arranged so as to anchor itself in the lateral face (E4, E5) of the spinous process (EI, ES) along which said wing lies (11, 12). An example is illustrated in FIGS. 2A through 2C, where points (111, 121) on the wings (11, 12) are arranged so as to anchor themselves in the lateral face (E4, E5) of the dorsal spine (EI, ES) along which the two wings lie (11, 12). In other embodiments, the sigmoidal insert (2) includes, on at least one of its concave parts, at least one point (221) arranged to anchor itself in the lateral face (E4, E5) of the spinous process (EI, ES) along which this convex part lies. An example is illustrated in FIGS. 4C and 4D; a point (221) is present near the rear end (posterior, in the insertion direction) of the insert (2). This point of the insert (2) is preferably curved in the direction of the anterior end of the insert (2), so as to more easily anchor itself in the lateral face of the spinous process during placement of the insert (2) in the body (10). The end of the insert (2) opposite the one equipped with this point (221) is inserted first into the passage (15). This point (221) can be a fixed point placed on the concave part of one of the faces of the insert (2), preferably close to or at the posterior end. The point (221) can also be a point pivotably mounted on the insert (2) so that it can be folded along one face of the insert (2) or unfolded in the direction of the spinous process. The pivoting point can then be mounted on the convex face, but it will then be offset so as to be anchor in osseous tissue beyond the end of the insert and its actuation will have to be carried out during insertion to orient it so that it penetrates into the spinous process.

In other embodiments, such a pivoting bone anchorage means can be mounted on the convex face or on the lateral edges of the insert (2), for example by extending beyond the posterior end of the insert (2), to be able to be applied to the spinous process, particularly after full insertion of the insert (2). For example, in the examples of FIGS. 7A through 7D, the posterior end of the insert (2) includes at least one pivoting hook (28). Likewise, the lower end of at least one of the wings can include at least one pivoting hook (28), in particular a series of pivoting hooks in these examples. It will be understood that one or more hooks can be arranged on each wing or insert. Bone anchorage means for the inserts, however, are generally only possible for the posterior ends of the inserts, and preferably only for sigmoidal inserts. Pivoting anchorage means are preferably associated with actuating means arrange to allow them to be pivoted so as to anchor them in the spinous processes. For example, in FIGS. 7A through 7D, the hooks (28) are assembled integrally with a pivot axis rotatably mounted in the insert and/or the wing and provided with an actuation means (280) having in this example a hexagonal (or generally polygonal) head able to be actuated by a tool to pivot the hook(s) (28). The shape of the hooks (28), like that of the points (221) of the insert (2), will preferably be optimized for penetration into bone, depending on the axis of implantation (the axis of rotation of the hook and the pivot axis of the insert in the body, respectively, particularly in the case of the sigmoidal insert the insertion of which can be performed along a sigmoidal trajectory with several consecutive pivot motions).

In certain embodiments, the interspinous implant comprises at least one retainer including at least one bone anchor or bone anchoring resources (3, 111, 121, 221, 7, 28), as previously mentioned. One may consider that the implant (1) comprises these resources (3, 111, 121, 221, 7, 28) or that these resources are independent, in particular in some embodiments of the latter in which they can be used with other types of interspinous implants. In fact, the bone anchoring resources detailed in the present application may be formed directly on the implant and/or the insert, but can also form a distinct device allowing to anchor the implant and/or the insert into a spinous process.

Figure 6A:
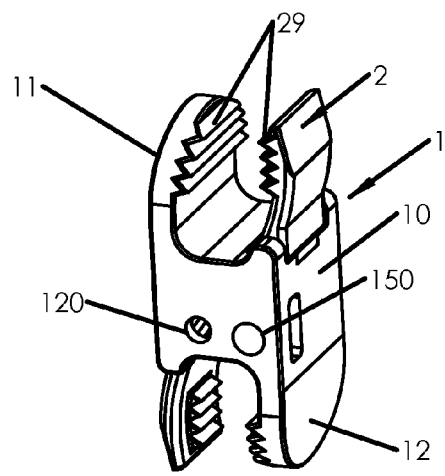
FIGS. 6A, 6C and 6E show perspective views of interspinous implants according to various embodiments, FIGS. 6B, 6D and 6F showing top views of the implants of FIGS. 6A, 6C and 6E, respectively.
Figure 6B:
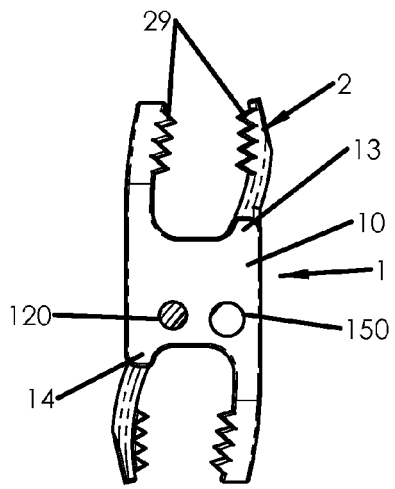
Figure 6C:
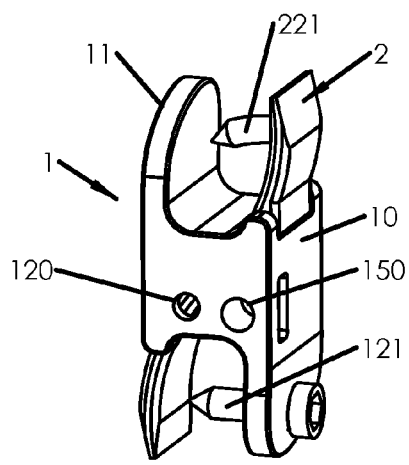
Figure 6D:
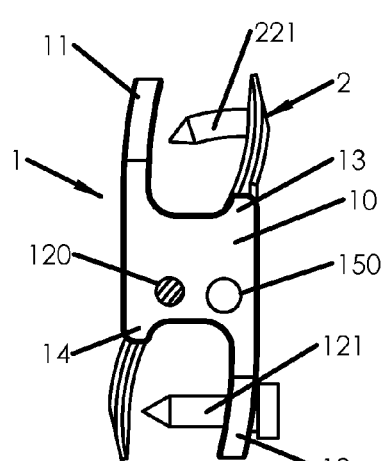
Figure 6E:
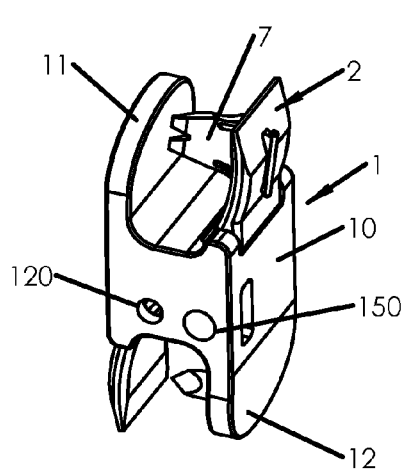
Figure 6F:
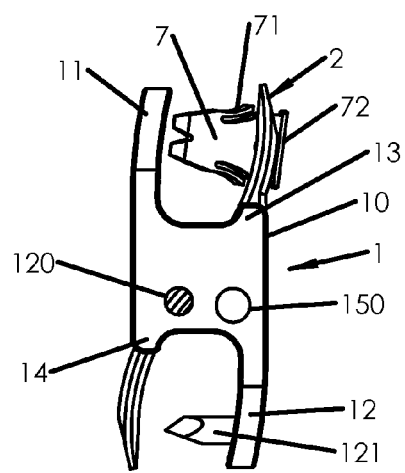
Figure 7A:
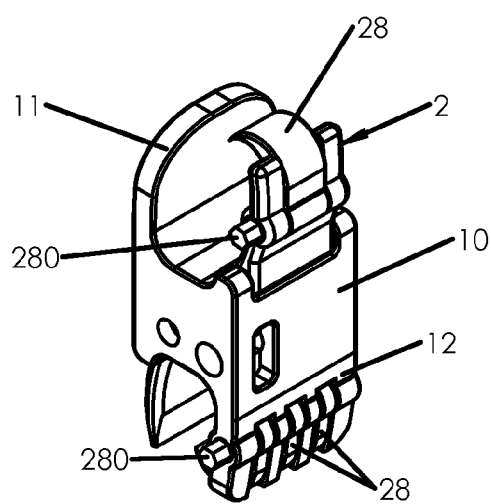
FIGS. 7A and 7C show perspective view of interspinous implants according to various embodiments, FIGS. 7B and 7D showing top views of the implants of FIGS. 7A and 7C, respectively.
Figure 7B:
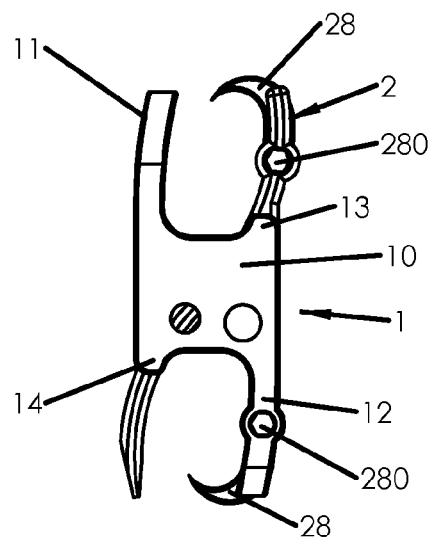
Figure 7C:
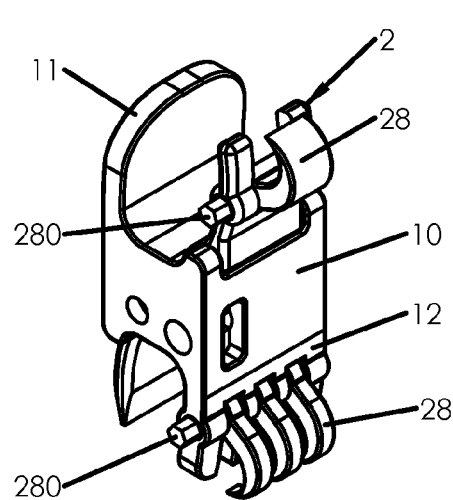
Figure 7D:
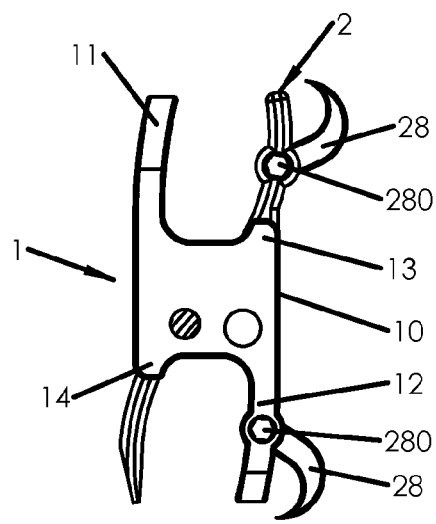

In certain embodiments, at least one of the wings (11, 12) and/or at least one insert (2) includes at least one passage such as a hole (131, 231, 123, 232) or a slit arranged to receive a bone anchor (3), as for example at least one pin (31, 32) of at least one bone anchorage device (3). The bone anchorage resources comprise preferably at least one pin. The pin preferably has a pointed end to be planted in the lateral face of a spinous process. In some embodiments, the bone anchoring resources comprise attachment resources for their attachment to the implant (1) and/or the insert (2), the latter comprising complementary resources for allowing the attachment of the bone anchoring resources thereon. For example, the pin can include at least one threaded portion, complementary to a tapped thread in the hole in the wing or insert, to allow screwing. A pin provided with a head that allows screwing along an axis substantially perpendicular to that of the pin will then be preferred, as for example a hexagonal head. In other embodiments, the pins are not threaded. For example, in the examples in FIGS. 6C and 6D, a point (121) is present near the posterior end of the insert (2) while the lower wing (12) is anchored in the lower spinous process using a screw. This screw runs through a hole in the wing, which preferably has a tapped thread complementary to the thread of the screw which includes a head with actuation means such as a polygonal shape or socket. The insert (2) shown in the example in FIGS. 5A and 5B can be used in an implant as shown in FIGS. 6E and 6F, because this insert includes an opening designed to allow passage of a bone anchorage means made up of a small anchor (7) which is driven into the lateral face of the spinous process. This anchor is preferably curved to facilitate its implantation from the implantation approach of the implant and includes preferably an insertion stop (72) and a withdrawal stop (71) similar to those detailed for the implant in the present application. This anchor is preferably made up of a metal plate, preferably sharpened at its anterior end to facilitate its penetration into the bone, and preferably includes an indentation at its anterior end for the same reason. This anchor thus has resources for attachment to the insert (2), formed by the insertion stop (72) and withdrawal stop (71). In other embodiments, these resources for attachment of the bone anchorage resources may be formed by a latch (35), such as a flexible leg provided with a tooth arranged to be clipped onto a shoulder of the implant and/or insert, such as in the illustrative and not restrictive FIGS. 19A, 19B and 19C. It will be understood from the various examples that various types of attachment resources are contemplated for the bone anchorage resources, in particular when the latter are formed by a device distinct from the implant and/or the insert. It will be noted that in the case of resources provided with a tooth clipped into the implant and/or the insert, a housing may be provided to allow access for disengaging the tooth from the shoulder, so as to enable withdrawal of the bone anchor. The access recess can be provided in the anchoring device and/or the implant and/or insert on which the attachment resources allow to attach the bone anchor.

In certain embodiments of the bone anchoring resources (3), two pins (31, 32), preferably pointed or sharp, are connected, at the ends opposite the pointed ones, by a transverse bar (30), substantially (i.e., at least approximately) perpendicular to the axis of the pins (31, 32), so as to form a bone anchoring device (3) substantially having the shape of a staple. In certain embodiments, the staple is designed so that its two prongs (31, 32) penetrate the spinous processes through holes in the implant. However, depending on the dimensions of the staple compared with those of the implant, the staple can be designed to penetrate into the spinous processes beyond the wings of the implant. In this case, means of attaching the staple to the implant will preferably be provided so that the staple constitutes a retainer for the spinous processes. It will be noted that this type of bone anchorage device (3) can be used with various types of implants described in the present application, particularly implants including a means of retaining the implant other than an insert, as for example a ligament (L), a complementary body, etc. In the examples of FIGS. 8A through 8C, the interspinous implant (1) has two wings (11, 12) having two holes (231, 232) and an insert of sigmoidal shape (2) having two holes (123, 131). A bone anchorage device (3) is then provided, with two points (31, 32), designed to first pass through the hole (231) in the insert (2) and the hole (123) in the wing (12), then, secondly, to pass through the two dorsal spines (EI, ES) and finally, thirdly, to embed itself in the hole (131) in the wing (11) and the hole (232) in the insert (2) on the other side of the spinous process. The bone anchorage device (3) including a pin or a bar (30) between the two anchorage points or pins (31, 32) can preferably have a pin or a bar (30) having at least one plane surface on the face where the points originate, and preferably the insert will include around the hole (231), for one of the points, at least one plane part to receive the plane part of the bone anchorage means, which allows the anchorage means to conform well to the shape of the implant, as can be seen particularly on FIG. 8C.

In such cases of bone anchorage means (3) forming a kind of staple, which provides means for retaining the spinous processes and thus supplements the implant's retainer formed by an insert (2), it is possible to provide an insert (2) arranged so as to be placed during the anchoring of said staple. For example, the sigmoidal insert (2) can include, at one of its ends an indentation, a notch, a cutting, or a split separating the curved plate into two branches (22, 23) and including an abutment surface intended to receive a transverse bar (30) of a bone anchorage device (3) including two pins (31, 32) perpendicular to said bar (30), the anchorage device (3) being arranged so that said bar (30) bears on the abutment surface of the indentation in the insert (2) and causes the insert to enter the through passage (15) of the implant (1) when the pins (31, 32) penetrate a lateral surface (E4, E5) of the vertebral spinous processes (EI, ES). While one of the pins (31, 32) passes between the branches (22, 23) of the insert for penetrating into one of the spinous processes, the other pin penetrates into the other spinous process, either through a hole (123, 131) in one wing (11, 12) of the implant as shown in FIGS. 11A and 11B for example, or directly as shown on FIGS. 18A, 18B and 18C and on FIGS. 19A, 19B and 19C for example. The bottom of the split thus provides an abutment surface for the bone anchorage means. This surface will preferably be curved (convex) in the sense of a portion of the outside of a cylinder, to facilitate the pivoting of the insert with respect to the bone anchorage means, particularly in the preferred case where those anchorage means have a plane face for better contact with the implant assembly once assembled, as described with reference to FIG. 8C and as can also be seen here in FIG. 11B.

Other illustrative examples of insert (2) arranged to be inserted during the anchoring of bone anchorage resources (3) forming a kind of staple are shown in FIGS. 18A, 18B and 18C and 19A, 19B and 19C. In the illustrative and nonlimiting examples of FIGS. 18A, 18B and 18C, the implant (1) and insert (2) represented are adapted to a multi-level surgery as detailed in this application. Of course, the same mechanism of simultaneous anchoring and insertion of the insert can nonetheless be provided with implants and inserts of other shapes. In the illustrative examples shown in FIGS. 18A, 18B and 18C, the bone anchorage resources and the insert are also arranged for the insertion of the insert during the anchorage of the anchoring resources. The insert, with an indentation separating the plate into two branches, comprises a connection (27) which links the two branches and protrudes out of the plane of these two branches. This connection keeps the bone anchoring device in place once implanted and thus forms an attachment resource as detailed above, but also facilitates the handling of the ensemble during the insertion of the insert and the bone anchoring. Indeed, the bone anchoring device (3) is introduced between the two branches of the insert (2) and retained relative to the insert thanks to this connection (27), as particularly shown in FIG. 18B. Moreover, in some embodiments, the implant is provided with at least one housing, recess, groove, slot, or other accommodation for at least a portion of at least one bone anchor. For example, in FIG. 18C, we see that the implant (1) has a groove on its lateral side receiving the bone anchoring device. The groove is sized and located so as to accommodate the crossbar (30) of the bone anchoring device (3). This housing will prevent the anchoring device from protruding too much outside the body (10) of the implant and thus present an overly large encumbrance. In the illustrative examples shown in FIGS. 19A, 19B and 19C, the bone anchorage resources are also formed by a staple (3), preferably with the crossbar (30) received in a longitudinal groove on a side face of implant (1). In this example, the crossbar (30) is provided with an attachment resource formed by a latch (35) comprising a flexible leg provided with a tooth designed to be clipped onto a shoulder (135) present in the body of the implant (1). In this example, the shoulder (135) is formed by the intersection between the prehension housing (150) of the body and the side groove receiving the staple. Other arrangements can of course be provided but the latter is particularly advantageous in terms of space since it allows the combination of two means (the lateral groove and the gripping housing) to provide a further synergistic technical effect, obtained by the intersection of both resources.

In some embodiments of the bone anchorage resources, especially when they contain at least one sharp (pointed) pin or tip, the latter may include teeth, detents, notches, protrusions, or any variations of shape adapted to oppose the removal of this pin once planted in the bone. Illustrative and non-limiting examples of such shape variations are represented for the sharp ends of the pins (31, 32) of bone anchors (3) in FIGS. 18A, 18B, 18C and FIGS. 19A, 19B and 19C.

In some embodiments of the bone anchorage resources distinct from the implant and/or insert, these bone anchorage resources comprise at least one grip or other grasping structure (36) to facilitate their removal. This grip or other grasping structure (36) of the bone anchorage resources (3) may include a housing, a projection or shape variation on a surface of the bone anchorage resources, to be gripped or held, for example with the end of a tool for removal of bone anchorage resources. In the example shown in illustrative and non-limiting FIGS. 18A, 18B and 18C, a housing (36) present on the crossbar (30) allows the introduction of a tool to pull on the bone anchorage resources.

In certain embodiments, said at least one retainer of the implant includes anti-slip means (29) allowing to retain the spinous processes, particularly on at least one part of at least one of the wings and/or on at least one part of at least one insert, to limit the motions of the implant (2) with respect to the spinous processes and conversely. For example, in FIGS. 6A and 6B, the wings (11, 12) and the insert (2C) have toothed surfaces or notches (29) to inhibit motion of the dorsal spines (EI, ES) relative to the implant (1) or conversely. When the insert (2) includes such notches (29) and/or points (221) near its anterior end, or at least on the portion which must pass through the body (10) of the implant, the passage (15) in the body (10) of the implant preferably is designed for the passage of these notches (29) and/or points (221). Thus, in certain embodiments, the passage (15) can be enlarged to allow the notches (29) and/or points (221) to pass. Likewise, in other embodiments, the entire width (i.e. dimension along the Y axis) of the insert is not occupied by such notches (29) and/or points (221), as shown for example in the figures of plates 36, 37, 38, 39 and 40. The passage (15) can then include grooves (155) for the passage of the notches (29) and/or points (221) instead of having to be enlarged over its entire height.

In some embodiments, hooking resources (4, 24) for hooking the spinous processes (EI, ES) are designed to improve the retention of the implant between two spinous processes, by hooking at least one of the spinous processes. In some of these embodiments, hooking resources (4, 24) are designed to hook the two adjacent spinous processes between which the implant is placed and, then, they provide a function of retaining the spinous processes, in addition to the function of retaining the implant. Here, "hooking resources" is used to designate structures which are arranged to extend so as to hook along at least part of an edge of a spinous process which is opposite to the edge of the spinous process against which the body (10) of the implant is disposed. It will nevertheless be noted that so-called "laminar" hooks are known in the field of vertebral column implants, which are arranged so as to hook around at least part of the edge of the vertebral lamina (that is the portion extending between the spinous process and the transverse process). It will therefore be understood that the hooking resources described here can generally be arranged to hook onto at least part of an edge of a spine and/or of a vertebral lamina. Double hooks can also be provided, for example with one branch that hooks onto an edge of a spine and another branch that hooks an edge of the lamina adjacent to this edge of the spinous process. This set of concepts is simply designated here by the term "hooking resources." Thus, for example, with an implant (1) inserted between the upper edge (E2) of a lower spinous process (EI) and the lower edge (E3) of an upper spinous process (ES), the spinous process's hooking resources (4, 24) are arranged to hook over the upper edge (E2) of the upper spinous process (ES) and/or the lower edge (E3) of the lower spinous process (EI). The simplifying term of "opposite edge" is used here to refer to the edge of a spinous process which is opposite the edge (E2, E3) which is in contact with the body (10) of the implant. The term hooking is used to denote the fact that these resources extend partially around an edge, like a hook that is hung on this edge. It will be understood that this hook shape is not limiting and that various shapes can be provided, as long as it allows hanging or retaining the implant on a portion of said opposite edge. Similarly, the extent of this hook, that is to say the portion to which it extends on the lateral face opposite the one from which it is implanted, may vary, preferably in a range allowing reliable holding of the implant. Preferably, these spinous hooking resources (4, 24) are arranged to be used from one side face of the spinous process, as most of the elements detailed in this application. These hooking resources (4, 24) allow, by extending to the opposite edge of two adjacent spinous processes, to limit or prevent the spinous processes from spreading apart, for example beyond the value at which they are maintained by the body (10) of the implant (1). Indeed, the implant is interposed between two adjacent edges and can impose a minimum distance between two edges of the two spinous processes, but these spinous processes may deviate from each other (spread apart), except in the case of bone anchoring resources designed for anchoring in both spinous processes. Thus, these spinous hooking resources (4, 24) can also maintain a maximum separation, by preventing the spinous processes from departing from each other, as do bone anchoring resources, but with the additional benefit of limiting the risk of injury to bones and of reducing the risk of degradation of the binding obtained. Another potential advantage of hooking resources (4, 24) is the variable setting of maximum separation obtained in some embodiments detailed in this application. In addition, since not all the spinous processes have the same "height" or "length" (that is to say the same dimension along the X axis), it is desirable to provide hooking resources (4, 24) with adjustable size or to provide various sizes of hooking resources (4, 24) in order to be able to hook the various spinous processes of the rachis.

In some embodiments, these hooking resources (4, 24) are formed on the implant (1) itself and/or the insert (2), but preferably only on one side and arranged to extend at least partially around the opposite edge of at least one of the spinous processes. Note that it is possible to combine bone anchoring resources on one spinous process with hooking resources on the other spinous process, for example as shown in FIGS. 20A and 20B, but also that both resources (hooking and anchoring) can be combined on a single spinous process or even that hooking or anchoring resources can be used on both spinous processes (EI, ES). These various resources are not necessarily exclusive from each other, although it's generally preferred that a spinous process is retained by only one of these resources. In addition, in the case where bone anchoring resources for a spinous process are combined with hooking resources (4, 24) for the other spine, the anchoring resources will preferably be chosen on the wing of the body that is on the side through which the spinous processes are accessed to, while the hooking resources (4, 24) will be on the side of the implant that is not equipped with wing (on the same side face of access), so as to avoid providing various sizes of implants (1) including hooking resources (4, 24). One advantage is then to be able to have the same type of implant (1) for use with various hooking resources (4, 24) of different sizes (to be adapted according to the size of the spinous processes). This is especially true when the hooking resources (4, 24) are formed on the insert (2), especially the sigmoid insert. However, in some embodiments, the position of the hooking resources (4, 24) can be adjusted as detailed below and this problem of the size of the spinous processes can be overcome. For example, a hook-shaped extension (24) can be attached to a wing of the body of the implant (1) at varying positions so that they can adapt to different sizes of spinous processes. In general, the hooking resources (4, 24) comprise at least one hook (24) which can be formed by a portion of the implant or of the insert, but which can also be separate and attached to the implant or the insert, for example through an attachment structure. One can for example choose for the first spinous process a first hook attached to the implant or the insert, and for the second spinous process a second hook attached to the implant.

In some of these embodiments having hooking means (4, 24) formed on the implant (1) and/or insert (2), these hooking resources (4, 24) are pivotally mounted on the implant and/or the insert. Thus, for example as shown in FIGS. 20A and 20B illustrating, without limitation, those two aspects on the same device (i.e., the aspect of combining anchoring and hooking resources and the aspect of pivoting hooking resources), an implant equipped with bone anchorage resources, for example, hooks (28) pivoting on one of its wings (12) is associated with a sigmoid insert (2) provided with hooking resources (24) which are pivoting. These hooking resources (24) are pivoting and mounted on the insert (2) so as to be handled from the same lateral implantation face as the other elements, by placing the hook-shaped portion against the opposite edge of the spinous process. In some embodiments of the pivoting hooking resources (4, 24), they are preferably lockable in their rotation, so that once they are placed on the opposite edge, the risk that they rotate in the opposite direction is limited. Thus, it is preferably provided that locking resources (241) allow locking the pivoting of the hooking resources (4, 24) (or at least resources limiting the risk that the pivoting hooks rotate in the opposite direction, that it to say that they disengage from the edge of the spinous process). For example, cuts, tangs, teeth or notches (241) opposing the pivoting of the hooking resources (24) in a direction away from the spinous process can be provided to abut the hooking resources (24). Alternatively, at least one tooth on a flexible structure that clips onto the edge of the pivoting hooking resources (4, 24) can be provided. On the other hand, in some embodiments of these pivoting hooking resources (4, 24), actuating resources (240) are provided for ease of pivoting. Thus, for example as shown in FIGS. 20A and 20B, the hooking resources (4, 24) are formed by rotating a hook (24) mounted on an axis (240) mounted freely rotatable in the insert (in this example, but possibly on the implant in other examples). In the same or similar manner as described above for the actuation means (280) of the pivoting hooks (28) for bone anchoring, the axis (240) may include a structure for its actuation by a particular tool (for example, in the illustrative and nonlimiting example shown, a hexagonal head manipulated by various types of known tools).

In some embodiments, the hooking resources (4, 24) are formed by the insert (2), for example by the sigmoid insert which is preferred in this case. Such type of insert (2) may include, at its rear end, a hook-shaped extension (24) to hook the opposite edge of the spinous process along which this insert runs, for example as shown in FIGS. 21A, 21B, 21C and 21D. In these embodiments, the shape of this hook extension (24) will be adapted to the shape and size of spinous process and to the radii of the plate (for example the shape of the sigmoid) to allow for hooking the opposite edge of the spinous process during the introduction of the insert (2) in the implant (1). In some embodiments, the insert (2) includes a plurality of withdrawal stops (20), but no insertion stop (25). Thus, in some embodiments, the retaining mechanism will be formed only by withdrawal stops (20) and the extension (24) which abuts on the opposite edge of the spinous process and thus forms an insertion stop for the insert (2). Preferably, a plurality of withdrawal stop will be chosen, for example in the form of flexible tabs (20) as detailed in this application. The plurality allows the insertion of the insert (2) to be gradual and variable in the implant. Thus, depending on the height (or length, i.e., dimension along the X axis) of the spinous process, the insert will abut on one tab (20) more or less close to the anterior or posterior end of the insert, when its hook extension (24) abuts on the opposite edge of the spinous process. Preferably, this type of mechanism will be configured with the curvature of the insert and the curvature of the hook extension providing a good hold on the opposite edge, whatever the tab (20) which stops the insert (2). The plurality of tabs (20) forms a mechanism similar to a rack for adjusting the hooking of the spinous process by the insert. The desired maximum separation can thus be chosen, for example with a continuous contact between the hook extension (24) and the opposite edge of the spinous process or with a slight play between the hook extension (24) and the opposite edge of the spinous process. For such a rack mechanism with several tabs, the housing accommodating the tabs will preferably be large enough to allow the unfolding of the tabs that have already passed the stop surface (122), so as to minimize or avoid unintentional folding of the tab (20) which corresponds to the stop position suited for the desired maximum spacing of the spinous processes. As seen in FIG. 21C, the flexible tabs (20) are preferably close to each other, to allow for fine tuning, but also possibly so that they strengthen each other. However, with this arrangement, when a tab closer to the front end than the other tabs folds by encountering a wall of the passageway in the insert, it will press on the following tabs and tend to fold them. So here, the housing in which lies the stop surface (122) within the implant (1) is large enough to avoid the problem of unwanted folding. For this, the housing may have dimensions along the axis of the passage through the implant, at least equal to the dimension between the free ends of the last tab (the posterior) and the first tab (most anterior). In these embodiments of insert (2) provided with a hook extension (24), the implant can have a hook-shaped wing to hook the opposite edge of the spinous process other than the one hooked by the insert, or provide anchoring resources for this other spinous process (or even simply provide no retainer for the other spinous process if one wants only to improve the retaining of the implant without limiting the distance between the spines). In the examples of FIGS. 21A and 21B, the implants (1) shown have a wing (12) extended by an extension (24) forming hooking resources for a spinous process. It should be noted here that the curvature and extent of this hook-shaped extension (24) of the wing is designed so that the implant can hook the opposite edge of the other spinous process (not the one hooked by the insert), according to the chosen location for the implant, in a manner similar to that shown in FIGS. 17A, 17B and 17C. Thus, this extension should not extend too far or be too curved to prevent it from passing the opposite edge of the other spinous process, but still have enough curvature to provide the hooking function.

In some embodiments, the hooking resources (4, 24), forming a retainer for retaining the implant and/or the spinous processes, are formed by at least one hooking device (4) distinct from the implant (1) and insert (2). This allows adding the hooking device (4) if desired and allows this device to be used with any type of implant described in the present application, preferably with an attachment structure or other means of connecting or attaching this hooking device on the implant (for example as detailed hereafter). This distinct type of device (4) has the advantage, in particular compared to the above embodiments where it is the insert that combines the two functions, of avoiding the insert (and its mechanism for retaining it within the body) from bearing the extension forces exerted by the patient bending frontward. Various illustrative and nonlimiting examples of such hooking devices (4) are shown in FIGS. 22A, 22B, 22C and 22D and FIGS. 23A, 23B, 23C and 23D. It will be understood from the present application that such devices are distinct structures from implants and inserts used for interspinous implants of various types, including those presented in this application. Thus, these distinct hooking devices may be claimed as such in association or not with an interspinous implant, of the type of this application or not. Indeed, in some embodiments, the hooking device (4) comprise linking or connecting resources (246) for linking or connecting the hooking device (4) to the implant (1) and/or the insert (2). The implant (1) and/or insert (2) can then comprise complementary resources (e.g., slot 245 as shown in FIG. 23A) for receiving the linking resources (246). Thus, these hooking devices (4) may be associated with and linked or connected to implants, for example the type of this application using an insert (2). In the case of implants different from those presented in this application, but linked to such a hooking device (4), it is possible to provide an extremely simple interspinous implant, for example simply forming a block to maintain a minimum distance between the spinous processes, while hooking device (4) form a structure for holding the implant in the interspinous space (by its link to the implant) and a structure for maintaining the maximum spacing between the spinous processes. Such embodiments provide a simple alternative with the advantage of a unilateral and minimally invasive implantation. In other embodiments, the hooking device (4) does not include linking resources for the implant or the insert and can therefore be used alone, although they may still be associated with an interspinous implant, which may generally not have the complementary linking resources (245) and will then preferably be provided with resources for keeping it stable in the interspinous space (as wings and/or insert in the present application for example).

In some embodiments, these hooking devices (4) preferably comprise two parts, preferably in the form of plates, each comprising, on the one hand, a curved portion forming a hook (24) for hooking the opposite edges of adjacent spinous processes and, on the other hand, at least one attachment structure (243, 244, 42, L, 41, 46, 47, 48, 49, L2, L3, L4, 44, 45). For example, one or both parts may comprise a female structure (244) receiving a male structure (243) of the other part, so that both parts can be attached to each other. Preferably, attachment structures are provided for adjustable attachment to enable adjustable fastening of both parts of the hooking device and obtain a hooking device (4) having a height (dimension along the X axis) which may vary depending on the size of the spinous process and the interspinous space. The result is a hooking device in which the distance between the two parts is adjustable and which allows controlling the spacing (the maximum distance) between the spinous processes. FIGS. 22A, 22B and 22C show illustrative and nonlimiting examples of such adjustable attachment structures. These examples include, first, a male portion (243) of one of the two parts of the hooking device (4), which include a series of teeth, cuts, notches, grooves or housings and, secondly, a female portion (244) equipped with a flexible tab, leg, tang, prong, or other protrusion configured to engage the teeth, cuts, notches, grooves or housings of the male part. Preferably, flexible tabs are chosen with one or more teeth to engage notches, so as to facilitate the setting of the penetration of the male portion into the female portion. The notches are then oriented to oppose the withdrawal of the male portion, so that it can be pushed easily into the female portion to adjust the hooking device (4) to the size of the spinous processes and so that the hooking device (4) is fixed once the desired size is achieved. It will be understood that the flexible tab or other protrusion can be provided on the male portion and that the series of teeth, cuts, notches, grooves or housing can be provided in the female portion, or even other arrangements for adjusting the height (or length, that is along axis X) of the hooking device (4). With such an adjustable mechanism, it is possible to adjust the size of the hooking device (4) to the desired maximum spacing between the two spinous processes, with or without play, by compressing the spinous processes or not (ie, by forcing the two spinous processes to approach each other or not). It will be understood that various types of adjustable attachment structure are contemplated, such as a male portion sliding in a female portion and immobilized by a screw or pin passing through a portion of the female portion and pressing on or extending through the male portion. For example, FIGS. 34A and 34B show an illustrative example of this type of adjustable attachment structure (243, 244, 42 L, 41, 46, 47, 48, 49, L2, L3, L4, 44, 45). The male portion (243) enters the female portion (244) to a variable depth and its position is locked by a clamp (42), such as a screw for example. FIGS. 35A and 35B shows another illustrative example of adjustable attachment structure. Hooks (24) each include a duct (44) in which enters a bar or rod (43) extending between the two hooks (or brackets) (24) each comprising a clamp (45) to fix their position along the rod (43). However, the notches are generally preferred because they facilitate assembly by avoiding the use of tool like required by a screw or nut and because they allow an easier adjustment thanks to the rack mechanism.

In some embodiments of the hooking device (4), each of its two parts comprises a curved portion (247) forming an offset so that the male and female portions are not aligned with the rest of the hooking device (4). Thus, these portions preferably remain parallel to the rest of the hooking device (4), but offset so that at least one instrument anchorage (151) of the implant remains accessible even when the hooking device (4) is placed on the implant (1), such as shown in FIGS. 22A and 23A for example. In other embodiments, the male and female portions are aligned with the rest of the hooking device (4), such as shown in FIG. 22C for example. Indeed, depending on the depth of the implant (ie, dimension along the Y axis) and the presence or not of this anchorage (151) on the implant, as well as the location of this anchorage (151) on the implant (1), it may not be necessary or desirable to provide such an offset (247). This offset (247), when provided, allows the hooking device (4) to be positioned in the middle of the height of the spinous process (dimension along the Y axis) and provides a hold as stable as possible. Nevertheless, it can be provided that the hooking device (4) is arranged to be placed deeper between the spinous processes (closer to the front of the patient). Inversely, the hooking device can be placed more at the rear of the patient and be tightened so as to bring the spinous processes closer from each other by using the body of the implant as a pivot so as to provide a (preferably slight) lordosis (the adjacent edges of the dorsal spines then being slightly less apart form each other than the height of the body). On the other hand, the size of the hooking device (4) in the depth dimension (Y axis) can be chosen so that it covers more or less of the depth of the edges of each spinous process.

Some embodiments of the hooking resources comprise an attachment structure for linking it to the implant (1) and/or the insert (2), as mentioned above. Thus, some embodiments of the hooking device (4) comprise connectors or other connecting means (246) for the implant (1) and/or insert (2), forming an attachment structure. These linking resources (246) generally cooperate with complementary resources (245) of the implant (1) and/or the insert. For example, the hooking device (4) may have a male part (246) arranged to engage a female part (245) of the implant, or vice versa. In the illustrative and non-limiting example of FIGS. 23A, 23B, 23C and 23D, the male part of the hooking device (4) is formed by a protuberance (246), for example such as a dovetail (or a T shape or similar restraining shape), protruding for example from its face intended to come into contact with the implant (1) and which is configured to engage the female part (245) of the implant on the corresponding face of the latter. This protuberance (246) preferably has a width smaller at its base than at its top end and cooperates with a housing, channel, or slot (245) of complementary shape in the implant (1). The width is then larger at the bottom of the housing (245) than at its surface, complementarily to the protuberance (246) of the hooking device (4). In some embodiments, non-sliding linking resources can be provided, such as a lug provided with a notch as in the case of the latch (35) provided for attachment of certain bone anchorage resources described in this application, cooperating with a recess in the implant and/or the insert.

However, in some embodiments, it is preferably that the linking resource (246) allowing sliding, along the X axis, relative to the implant (1). This type of sliding link is particularly advantageous because it allows the position of the two parts of the hooking device (4) to be adjusted in relation to each other and to the implant. Indeed, the inter-spinous spaces and the spinous processes themselves do not have the same size depending on the level along the rachis and of the patient receiving the implant, so generally it is advantageous to obtain adjustable positioning of each hook (24) of the hooking device (4) in relation to the spinous processes. This avoids having to dimension and/or configure the hooking device (4) or a portion of it depending on the size of the spinous processes. Thus, to facilitate the coupling between the implant (1) and the hooking device (4) and get an adjustable device, it the housing (245) of the implant may, for example, form a groove opening on at least one side of the implant, such as the upper and lower surfaces in the example shown in FIG. 23A, and that the protrusion (246) form a rail to slide into the groove of the implant, as shown in FIGS. 23A and 23B. This type of link is sufficient because the desired fixation of the hooking device (4) on the implant principally concerns the Z axis (and may concern the Y axis too) and the fact that the implant (1) can slide relative to the hooking device (4) along the X axis is not a problem since these latter will be held together by their relations with the edges of the spinous processes. Instead, this sliding along the X axis allows the two parts of the hooking device (4) to be as adjusted to the size of the spinous processes, and allows such adjustment to be performed during the implantation itself. The result is a stable assembly, in particular by adjusting the penetration of the male portion into the female portion of the hooking device (4), to adjust the maximum separation of the spinous processes. It is therefore understood that in embodiments where the hooking device (4) is arranged to be slidable relative to the implant and of adjustable height in relation to the spinous processes, the implant (1) can be inserted first in the interspinous space, then the insert (2) can be introduced in the implant, then the rail (246) for attachment of the hooking device (4) can be introduced into the groove (245) of the implant, and then the sliding of the two parts of the hooking device (4) can be adjusted relative to the implant. All these operations can advantageously be performed from one side face of the spine, which facilitates the implantation as described in this application.

Various embodiments may include hooking resources (4, 24) having at least one attachment structure on the implant and/or on the insert and/or at least one attachment structure between two parts of the hooking resources (mainly the hooks or brackets). The examples of bar or rod and of male and female portions provided above are not exhaustive and various types of attachment structure (243, 244, 42 L, 41, 46, 47, 48, 49, L2, L3, L4, 44, 45) can be provided. For example, FIGS. 30, 31, 32 and 33 show other embodiments of hooking resources (4, 24), in which the attachment structures include at least one flexible link (L) or ligament (L) which may for example be of the type described below as a retainer for the implant. In some of these embodiments, the hooking resources preferably comprise two hooks (24) each hooking one spinous process and connected together by at least one ligament (L). Preferably, the insertion of the ligament (L) on the hooks (24) is obtained by adjustable resources so as to adjust the distance between the two hooks (brackets). Thanks to the flexibility of the ligament, these embodiments are particularly advantageous because they facilitate the adjustment. In addition, the ligament may have elasticity allowing application of tension during the adjustment. Thus, the maximum spacing between the spinous processes may be limited to a range depending on the tension applied to the ligament during its installation. Various options are provided for the adjustment of the ligament and examples of these possibilities are shown in FIGS. 30, 31, 32 and 33. In these examples, a first end of the ligament (L) is attached to a first hook (24). For example, a loop (L3) at one end of the ligament (L) is attached to the first hook (24).

In some illustrative and non-limiting examples of hooking resources (4, 24), shown in FIGS. 32 and 33, this loop (L3) passes in the first hook (24), and a loop (L3) of a second ligament (L) passes in the second hook (24). Once the two hooks (24) are in place, the two ligaments (L) are manipulated to extend towards each other and they are both threaded into a locking means (41), such as a pressure-crimped attachment, collar, clamp, crush sleeve, etc. This type of locking means (41) may naturally have various shapes, including cylindrical (FIG. 33) or rectangular (FIG. 32). In addition, this type of locking means (41) may have notches, teeth, or hooks on the inside to improve the retention of the ligament and may have slots to facilitate the crushing of the ligament during crimping (for example in FIGS. 32A and 32B in which these two characteristics of slots and notches are combined). FIGS. 32A and 33A show this type of arrangement before the crimping of the locking means (41) while FIGS. 32B and 33B show the same arrangement once the crimping is performed.

In another illustrative and non limiting example of hooking resources (4, 24), shown particularly in FIG. 30A, the ligament (L) is attached to a hook (24) through the loop (L3) at one end and extends toward the other hook in which it can pass through at least one passage (46). It is generally preferred to have a plurality of passages (46) for adjusting the length of the ligament (L) (and thus its tension if it is elastic) by choosing one or other of the passages (46) in the second hook (24). The second end of the ligament (L) has a hook (L4), for example attached to the ligament with a weaving, a loop or a crimping mechanism. The ligament extends from the second hook to the first hook at which the hook (L4) of the ligament (L) can be inserted into a plurality of housings (47) allowing adjustment. FIG. 30A, with its expansion in FIG. 30B, shows this arrangement before insertion of the hook (L4) of the ligament in the housing (47) of the first hook, while FIG. 30C, with its expansion in FIG. 30D, shows the arrangement with the hook (L4) of the ligament (L) introduced into the housing (47) chosen. The shape of the hook (L4) of the ligament provides an adequate lock which, with the tension of the ligament (L), prevents the ligament from withdrawing. FIG. 30E shows a top view of the ensemble.

In another illustrative and non limiting example of hooking resources (4, 24), shown particularly in FIG. 31A and its expansion in FIG. 31B, the first hook (24) has an axis (48) of rotation. A rod, perpendicular to this axis (48) and carrying a plurality of fingers (49) substantially perpendicular to the rod, is mounted free in rotation around this axis (48) to allow pivoting of the fingers around the axis of rotation (48). Loop (L3) of the first end of the ligament (L) is fixed around the axis (48) of rotation, as shown particularly in FIG. 31C (this loop was not shown in FIGS. 31A and 31B to better show the axis and pivoting fingers). The ligament extends from the loop (L3) to the second hook in which it can pass through at least one passage (46). It is generally preferred to have a plurality of passages (46) for adjusting the length of the ligament (L) (and thus the tension if it is elastic) by choosing one or other of the passages (46) in the second hook (24). The second end of the ligament (L) has a second loop (L2) which can be slipped over any of the fingers (49) of the first hook (24) to allow adjustment of the insertion of the ligament (L) on the first hook (24). The rod (and the plurality of fingers (49) that it bears) is designed to be folded towards the first hook. Locking means are provided for retaining the plurality of fingers (49) in folded position. Preferably, the fingers are maintained in the thickness of the hook (24) so that it does not jut out when in folded position. For example, as shown in FIGS. 31C and 31D, the rod and the plurality of fingers (49) are arranged to fit in a window on the first hook (24) and to be retained in this window, for example using a clipping mechanism. The fact that the ligament (L) can be slipped over a finger facilitates the adjustment and the fact that the fingers rotate around the axis facilitates the tensioning of the ligament when locking it. Note that the adjustment or setting can also be carried out during the passage of the ligament in the passages (46) of the second hook. Note also that in the various examples above, the loops (L3, L4) of the ligament may have been provided in advance or can be performed by the surgeon himself during the implementation, for example by folding a free end of the ligament (L) on itself and sewing the end to a selected position on the ligament (L).

It will therefore be understood that in some embodiments, a first retainer means formed by the insert is complemented by a second retainer formed by a first hooking resource having a hook partially surrounding a first spinous process. Both retainers can be complemented by a third retainer formed by a hooking resource having a hook partially surrounding the second spinous process. This second hooking resource can then provide, in cooperation with the first hooking resource (when the hooking resources are connected to the implant and/or to each other), a function of retaining the spinous processes at a determined spacing or range of spacings, in addition to the function of retaining the implant.

In various embodiments, particularly the preferred ones, that is those in which a first wing lies along a lateral face of a spinous process while the second wing lies along the other face of the other spinous process, various types of retainers for retaining the implant and/or the spinous processes are provided, replacing or supplementing the insert (2), the anchorage or the hooking means or resources described above.

Advantageously, in certain embodiments, the retainers of the implant are preferably arranged in a substantially symmetrical fashion to the arrangement of the body (10) with respect to the sagittal plane (A) passing through the center of the implant (1), but the different parts of these retainers are not necessarily symmetrical to one another.

In certain embodiments, the at least one retainer has/have a flexible connector (L) such as a cord or lace for example, which passes through the body (10). The flexible connector, also called a "ligament" in the present application with reference to its physical properties and its use as a connector between elements in relation to the skeleton) can be composed of synthetic fibers, such as Dacron® polyester fiber produced by E.I. du Pont de Nemours and Company of Wilmington, Del. for example, and/or other polymers or plastics, and/or other suitable materials. To suit the use to which it is put, the connector or ligament must preferably have good resistance to elongation and generally show a certain elasticity allowing it to be stretched during its implantation and/or after implantation when it is subjected to forces due to the movements of the patient. Often, such a connector is in fact made of fibers, generally woven (or knit or felted) to lend elasticity to the connector. These fibers are generally strong and the connector is therefore robust despite its elasticity.

Such a flexible link (L) can be included in the attachment structure of the hooking structures (4, 24) as detailed above. On the other hand, such a flexible connector (L) can also be used itself as a hooking resource or as a means of hooking the spinous processes, similarly to what is described for the latter in the present application, with the difference that the flexible link lies generally along the two faces of the spinous processes instead of only hooking onto one edge of them from a single lateral face. This flexible connector (L) can either pass through the spinous processes, being then called "trans-spinous," or encircle the spinous processes, then being called "peri-spinous." It will be noted, however, that a trans-spinous path can be selected for one of the two spinous processes and a peri-spinous path for the other spinous process, for various reasons such as for example when an implant for multilevel surgery is desired as explained in the present application (the trans-spinous path being then preferred for the spinous process that will be located between the two implants).

In the embodiments where the flexible connector (L) is trans-spinous, it passes through the dorsal spinous process at a hole previously made by the surgeon through the spinous process, that is along an axis that is not parallel to the sagittal plane (or of the spinous faces), preferably an axis substantially perpendicular to the sagittal plane (A).

Preferably, a passage (100) passing through the body (10) and designed to receive the flexible connector (L) allows the latter to run from one lateral face (E4, E5) to the other (E5, E4) between the two spinous processes (EI, ES). In the case where the flexible connector is designed to be trans-spinous, the wings (11, 12) of the implant preferably also include a hole or duct (125, 128, 110) serving as a passage and/or attachment for the flexible connector (L). Especially advantageously, the passage (100) passes through the body (10) from one lateral face (E4, E5) to the other (E5, E4) following an oblique path, orienting the flexible connector (L) toward the portion of each lateral face (E4, E5) not having a wing (11, 12), as can be seen particularly in FIG. 25B.

In certain embodiments of the trans-spinous flexible connector, this flexible connector (L) has a first end integral with a first wing (11), preferably by means of an attachment of the flexible connector to that wing. For example, the flexible connector (L) is affixed to the wing (11) or attached at a hole or duct (110) in the first wing (11), for example by a knot in the flexible connector which bears on the edges of the hold or duct passing through the wing (11) and in which the flexible connector (L) runs. The second end of the flexible connector (L) passes through the hole or duct (125) in the opposite wing (12). In FIG. 25B, the holes or ducts (110, 125) in the wings (11, 12) are shown as being arranged symmetrically from one wing to another, but any other arrangement can be contemplated, in particular if it is desired that the flexible connector (L) run higher or lower relative to the two dorsal spinous processes (EI, ES), that is more toward the edges of the dorsal spinous processes opposite the edges between which the implant is inserted. In addition, these holes are shown centered relative to the depth of the implant (Y axis), but other arrangements can also be considered if it is desired that the flexible connector run more toward the crests or more toward the vertebral bodies, in other words more rearward or more forward of the patient, respectively. It is understood that in various embodiments, the flexible connector (L) lies along at least part of the lateral faces of the two spinous processes and has substantially an S shape in the coronal plane (defined by the X and Z directions).

Locking means or resources (125, 128, 1280) is preferably provided for locking the flexible connector (L) relative to the implant, generally relative to this second wing (12) since that is the one that remains on the side through which the interspinous space is approached in the figures shown (the reverse configuration can also be contemplated, as the body is often symmetrical). For example, this locking means can comprise a conical or trunconical element having a duct at its center allowing passage of the flexible element (L), and preferably a slit along part or all of its height to facilitate its compression. This conical element can then be set on the ligament, then inserted into the duct (125) to be compressed there and thus clamp the flexible connector (L). An example of such locking means consisting of a truncated cone (1280) is shown in FIGS. 26A and 26B. This split truncated cone (1280) is designed to receive the ligament (L) and to be inserted into a duct (128) provided in a boss on the body. In the example of Plate 25 in the figures, such a truncated cone would be inserted into the duct (125) in the second wing (12). In the example of FIGS. 26A and 26C, such a duct (128) is oriented parallel to the wing such that the path of the ligament is peri-spinous for this spinous process. In FIG. 26B, it is seen that the hole or duct (110) in the first wing is located near the upper edge of the lower spinous process. It is understood that with the oblong or elliptical coronal section of the spinous processes, this location leaves enough space for a knot to be set between the spinous process and the first wing (11) of the implant. Thus, in this example, a knot (not shown) in the ligament constitutes an attachment of the ligament (L) to the implant. This ligament, with its knot at one end to bear on the first wing (11), passes through the duct (110) in this first wing (11) then goes around the lower spinous process to pass through the passage (100) in the middle of the body, then goes around the upper spinous process to be locked by this locking means (128, 1280). It is understood by examining the figures in Plates 25 and 26 that the implant can be designed with ducts (110, 125) perpendicular or parallel (128) to the longitudinal axis of the implant (X axis) and set at different distances from the ends of the wings, so that an implant (1) having only two wings and having only one ligament (L) as a retainer can be peri- or trans-spinous. It is also understood how a peri-spinous path is obtained for one spinous process and a trans-spinous path for the other spinous process, by using various combinations of the configurations described above. It will also be noted that they are not necessarily mutually exclusive. Indeed, FIG. 26 shows for example that the duct perpendicular to the second wing (12) can be retained in addition to the duct (128) parallel to the wing (this duct, not labeled in this figure, is retained an visible behind the ligament at the second wing).

An example of placement of the interspinous implant the retainer whereof is a flexible connector (L) is illustrated in FIG. 25C. This placement occurs for example in the following manner: The flexible connector (L), attached to a first wing of the implant (the lower wing (11) in FIG. 25C), is run into the interspinous space which is to receive the implant, then by the use of a curved tool (such as a curved needle for example), through a first spinous process (or around the spinous process in the case of a peri-spinous implantation). The connector is then inserted through the passage (100) in the implant, then again into the interspinous space to be run into (or around) the other spinous process using a curved tool, for finally run into the hole or duct (125) in the second wing (12). Finally, the surgeon pulls on the free end of the flexible connector (L) sliding in the implant and the spinous processes, while inserting the first wing first to place it on the lateral spinous process face opposite that where the approach is performed. By pulling on the flexible connector, the surgeon allows the two wings of the implant to each press against one lateral face of one of the two spinous processes. The surgeon then locks the flexible connector (L) relative to the second wing and can cut off the protruding part of the flexible connector.

In certain embodiments, of which illustrative and non-limiting examples are shown in FIGS. 27A, 27B, 27C, 27D, 27E and 27F, the retainer of the implant relative to the spinous processes, and particularly for maintaining the position of the body (10) relative to the two dorsal spinous processes (EI, ES), comprises a so-called complementary body (90), with dimensions designed to maintain a distance between the adjacent edges (E2, E3) of the two spinous processes (EI, ES) and designed to be placed on top of the body (10) such that two wings (91, 92) of the complementary body (90), each extending along an opposite lateral face (generally substantially parallel to said sagittal plane), are each located on a lateral face opposite to that of a wing (11, 12) of the body (10). It is therefore understood that, in these embodiments, the two bodies (10, 90) in fact constitute mutually complementary half-implants. Thus, these two half-implants constitute for example, once assembled, an interspinous implant with an H or X shape in top view (in the coronal plane defined by the X and Z directions), the two wings (11, 12) of the body constituting two opposite half-branches of the H or X and the two wings (91, 92) constituting the other two opposite half-branches.

In certain of these embodiments, the wings (11, 12, 91, 92) of each of the two bodies (10, 90) extend over the part of the other body (90, 10) which is not provided with a wing. The wings extend for example, on their lateral face parallel to the sagittal plane (A), up to the lateral face of the other body (90, 10). In other words, the dimensions of the wings (11, 12, 91, 92) in depth, that is along the Y axis, are greater than those of the body, such that the wings of each of the two bodies (10, 90) extend over the part of the other body (90, 10) which is not provided with a wing in addition to the part of the body from which they originate. Thus wings can be provided for both bodies which have dimensions of depth (i.e. along the Y axis) substantially equal to those of the two stacked bodies (in their parts located between the wings). Thus the wings of each body complement the wings of the other body to constitute a complete implant the wings whereof extend to the same depth (along the Y axis) as the two bodies combined. The wings can also be designed to cover substantially the same surface (substantially parallel to the sagittal plane) as the two stacked bodies, but it will be noted that they can nevertheless cover a larger or smaller surface according to various possible variations. Moreover, the height dimensions of the wings (along the X axis) can vary so as to lie along a greater or smaller portion of the lateral faces (E4, E5) of the spinous processes (EI, ES).

Locking means (910, 900, 101) are designed to maintain the two bodies (10, 90) stacked by fixing their positions relative to one another, such that the wings (11, 12, 91, 92) of each body (10, 90) maintain the orientation of the other body (90, 10) relative to the two dorsal spinous processes (EI, ES). Thus, it will be understood that the complementary body (90) constitutes a retainer for the implant by providing the wings complementary to those of the first body. In addition, according to various embodiments, the two bodies (10, 90) can be mounted so as to pivot relative to one another or to be separated and designed to be assembled together. The locking means then allow locking of the position of the two bodies which constitute the ultimate implant. It will be noted here that the first body and the second body are mentioned and that this could refer, respectively, to the body (10) of the implant and to the complementary body (90), but that the configuration could be inverted, so long as the locking means were suitably arranged. The fact that the implant is made up of two bodies has the advantage of facilitating implantation. For example, when a first body is set between the spinous processes, with the wings lying along a first lateral face of each spinous process, the other body mounted pivotably on the first can have a different orientation from that of the first body, then be turned to a position, called the deployed position, in which its wings lie along the other lateral face of each spinous process. One example of this pivoting from a given orientation to the deployed position is shown in FIGS. 27C and 27D. In the case of two separate bodies, they can be designed to be inserted in the interspinous space either simultaneously or in succession. When they are designed to be inserted simultaneously, as shown for example in FIGS. 27A and 27B, the two previously assembled bodies are inserted together, but the wings of the first body will be placed so as to lie along a first lateral face of each spinous process, while the second body will have a different orientation from that of the first body (perpendicular to it, for example) to facilitate insertion of the first body, then once that is completed it will be turned to the deployed position. In the case of two separate bodies designed to be inserted into the interspinous space in succession, as shown for example in FIGS. 27E and 27F, the first body is inserted and its wings are placed to as to lie along a first lateral face of each spinous process. The second body will then be inserted afterward, with an orientation different from that of the first body already in place (oblique or perpendicular for example), then it will be turned to the deployed position.

It will be noted that in certain embodiments, and particularly in the case where the two bodies (10, 90) are designed to be inserted in succession, one of the wings of the second body can be dimensioned to facilitate its insertion into the interspinous space where the first body is already situated. Thus, as shown for example in FIG. 27F, a single wing (91) of the complementary body (90) extends over the entire lateral face of the body (10) which is not provided with wings, while the other wing (92) of the complementary body (90) does not extend substantially farther than the body (90) and does not cover the other lateral face of the body (10) which is not provided with wings. The fact that this second wing has dimensions of depth (along the Y axis) which does not exceed or exceeds only slightly the dimension of the body allows facilitation of the insertion of the complementary body (90) into the interspinous space when the body (10) is already in place between the two dorsal spinous processes (EI, ES) because it will need less space for passing (which may prevent pushing or even wounding the subspinous ligament). The second wing of this complementary body can, however, have larger dimensions without complicating the implantation.

It is therefore understood that in these various embodiments, the two bodies (10, 90) will pivot relative to one another, whether or not they are mounted one on the other and are therefore inserted simultaneously or successively into the interspinous space; this pivoting will preferably be centered on the center of the implant, for example centered on an axis oriented along the Y axis and passing through the center of the implant. Locking means (910, 900, 101), eccentric (offset) with respect to this pivoting axis, are therefore provided to clamp the relative position of these two bodies and the latter constitute the at least one retainer of the implant (for one another). For example, in FIGS. 27C and 27D, the two bodies are mounted so as to pivot about an axis of rotation (not shown). A first of these two bodies, for example the body (10), has for example a central stud and the second of the two bodies, for example the complementary body (90), has a matching recess so as to pivot about the stud while remaining stacked on top of the first body (10). Provision can be made for the two bodies to be assembled by a rotation pivot holding them together to avoid them disassembling, while still allowing them to pivot relative to one another. Locking means (910, 900) such as a screw for example (910) passing through a duct (900) in the complementary body (90) into a bore threaded into the first body (10) to be screwed into it, thus allowing the two bodies to be locked together. It will be noted that the eccentricity (offset) of these locking means (900, 910) not only allows the rotation of the two bodies to be locked, but also facilitates access for locking when the implant is in place between the spinous processes. The embodiments having two bodies pivoting relative to one another are generally arranged to allow rotation such that a portion of each of the wings (91, 92) of the complementary body (90) can come into contact with a portion of a wing (11, 12) of the first body (10), as shown for example in FIG. 27C, to facilitate the insertion of the implant between the spinous processes (EI, ES), then so that the rotation allows deployment of the wings (91, 92) of the complementary body (90) to a deployed position where the two bodies form the interspinous implant whose wings are able to lie along the spinous processes, as shown for example in FIG. 27D. It will be noted that the eccentric (offset) locking means can possibly be oriented along an oblique axis as in FIGS. 27E and 27F for example. An oblique axis generally facilitates locking when the implant is in place between the spinous processes. Indeed, once the implant is in place between the spinous processes its body is in the axis of the spinous processes and access to these locking means can be impeded by the interspinous and subspinous ligaments, injuries to which will preferably have been minimized. The eccentricity (offset) and/or oblique axis of the locking means (910) therefore facilitates access to them to allow locking or unlocking of the two bodies.

In certain embodiments, particularly those where the two bodies are separate but pre-assembled together and designed to pivot relative to one another, as shown for example in FIGS. 27A and 27B, locking means (or resources) can constitute the rotation pivot for the two bodies. For example, in these figures, a screw (910) running through a duct (900) in the complementary body (90) to a threaded bore in the first body (10) to be screwed in there is set in the center of the implant and can serve as a rotation pivot. In this example, but also in the embodiments where the two bodies are designed to be inserted in succession, as for example those shown in FIGS. 27E and 27F, rotation locking means are provided for preventing the rotation of the bodies relative to one another. For example, projecting studs (101) on the first body (10) are arranged to cooperate with matching recesses (not shown) in the complementary body, when the latter has attained its deployed position, as shown in these FIGS. 27A, 27B, 27E and 27F. Driving the screw (910) then allows the complementary body to come into contact with the first body (10) and allows these studs to penetrate into the recesses in the complementary body to lock the rotation. It is therefore understood that with such studs, the two bodies assembled using the screw are stacked but are held at a distance from one another, requiring a larger space for their insertion between the spinous processes than in the embodiments having a central rotation pivot and eccentric locking means, like those shown in FIGS. 27C and 27D detailed above, for example. In the embodiments of FIGS. 27E and 27F, the axis of the locking means is eccentric with respect to the implant and obliquely oriented, facilitating the locking of the two bodies inserted in succession between the spinous processes as detailed above.

The present application describes in detail various embodiments of an implant comprising firstly a body (1) including at least two wings (11, 12) extending so as to each lie along a lateral face of a spinous process and additionally at least one retainer for the implant (and possibly for retaining the spinous processes). Various possible arrangements for these various types of retainers (2, 3, 4, 7, 111, 121, 221, 24, 28, 29, L, 90), as well as their respective advantages, are described in the present application. Moreover, these various types of implant retainers are not necessarily mutually exclusive, whether they also constitute retainers for the spinous processes or not. Thus for example the flexible connector (L) constitutes a particularly advantageous retainer due to its ease of implantation given that it is a flexible element, but in certain cases (certain pathologies for example), a greater stiffness in the support is preferred and it is possible, instead of replacing the ligament (L) with another design, to combine it with another design, such as for example an insert (2). Examples of such a combination of a flexible connector (L) and an insert (2) are shown in Plates 28 and 29 of the figures. In such a combination, the insert constitutes the retainer for the rigid implant while the ligament constitutes a more flexible retainer and will therefore essentially play the part of restraining the motion of the spinous process which the insert (2) allows (hence mainly extensional motion, but also possible rotational motion if the wings and the insert are designed to allow lateral clearance). The ligament or flexible connector (L) can be combined with bone anchorage means (3, 7, 111, 121, 221, 28, 29), as for example a staple (3), or with spinous process hooking means (4, 24), but in these cases, the flexible connector (L) will generally play essentially its part of retaining the implant while the role of retainer for the spinous processes will essentially by provided by the other means. Nevertheless, the combination of the two designs offers greater safety for the implant, particularly through synergistic effects. For example, when a ligament (L) surrounds two spinous processes and a staple (3) or a hooking means (4), the latter are held on the spinous processes and will be less liable to become unhooked. Likewise, when a ligament supplements a hooking means consisting of an insert (2), the ligament (L), by preventing the spinous processes from spreading, relieves the withdrawal stops of the insert (2).

In certain embodiments, examples of which are shown in Plates 28 and 29, the implant comprises an insert constituting a retainer for the implant (1) and a ligament also constituting an implant retainer, but primarily a retainer for the spinous processes. In the example of FIGS. 28A and 28B, the ligament (L) or flexible connector is used peri-spinously for a first spinous process (for example the upper spinous process) and trans-spinously for the second spinous process (for example the lower spinous process). The ligament, for example with a knot bearing on the entrance of the duct (128) oriented parallel to the first wing (12) runs along this first wing (12) then runs around the first spinous process (the upper spinous process (ES) in FIGS. 28A and 28B), then runs along the rear end of the insert (2). The insert (2) then preferably includes an indentation, a cutout or a notch separating its rear end into two branches (22, 23), as can particularly be seen in FIG. 28D, to facilitate passage of the ligament (L). The ligament (L) then runs through a passage (100) through the body (10). This passage (100) is preferably, in these embodiments, parallel to the passage (15) in the insert, and for example provided in a wall of this passage (15) in the insert, as can be seen particularly in FIG. 28C. The ligament then emerges on the other lateral face of the implant and runs along the front end of the insert. Preferably, this insert (2) includes an indentation, a cutout or a notch separating its front end into two branches (220, 230), as can particularly be seen in FIG. 28D, to facilitate passage of the ligament (L). This ligament then runs through the second spinous process (the lower spinous process (EI) in FIGS. 28A and 28B), as can particularly be seen in FIGS. 28A and 28B, then enters a duct (156) passing through the second wing (11). Preferably, the entrance to this duct, or even the entire inner face of the wing, is provided with a gutter or groove (157) to receive the ligament (L) so as to avoid the latter being squeezed between the wing and the spinous process, as can particularly be seen in FIG. 28C. A locking means (18) is provided for locking the ligament in its passage through the duct (156). Such a locking means can be constituted by a screw or other element that can be screwed into the body or by a rod (181) provided with a hole (182) for passage of the ligament (L) and with a thread for screwing on a nut (18), as can for example be seen in FIG. 28C. This rod (181), when the nut (18) is screwed on, rises within the body and squeezes the ligament (L) between the walls of the duct (156) in the implant and the hole (182) in the rod. The ligament thus squeezed is locked relative to the implant. The dimensions of the male and/or female thread are preferably designed to prevent the ligament from being completely crushed, or even cut through by the locking means, while still providing sufficient locking. In can be seen particularly in FIGS. 28A and 28B that the ligament re-emerges from the implant on a lateral face, at the exit of the duct (156) in the implant and this free end can be cut if it is too long, so as to avoid having it snag neighboring tissues for example. It is understood that for such an implantation, the ligament is preferably first run into the duct (128) in the first wing, then hooked around the upper spinous process, then inserted in the passage (100) in the implant, then run through a hole previously made in the lower spinous process, and finally run into the duct (156) in the implant, leaving enough slack in the ligament to facilitate the manipulation of the ligament (L) and the implant (1). Then, by inserting the first wing (12), then the body (10) between the spinous processes, the surgeon can progressively pull on the ligament to apply the two wings of the implant against the spinous processes, then lock the ligament.

In the example of FIGS. 29A and 29B, the ligament (L) or flexible connector is used peri-spinously for a first spinous process (but the lower spinous process this time, in this example) and trans-spinously for the second spinous process (the upper spinous process this time). In this example, the ligament (L), with a knot bearing on the outside of a hole (125) through the first wing (12) runs through this wing (12) and the upper spinous process, then runs along the rear end of the insert (2). The insert (2) preferably includes a indentation, a cutout or a notch separating its rear end into two branches (22, 23), as can particularly be seen in FIG. 29B, to facilitate the passage of the ligament (L). The ligament (L) then runs through a passage (100) through the body (10). This passage (100) is preferably, in these embodiments, parallel to the passage (15) in the insert, and for example made in a wall of that passage (15) in the insert. The ligament then emerges on the other lateral face of the implant and runs along the front end of the insert. Preferably, this insert (2) includes an indentation, a cutout or a notch separating its front end into two branches (220, 230), as can particularly be seen in FIG. 29B, to facilitate the passage of the ligament (L). This ligament then runs around the second spinous process (the lower spinous process (EI) in FIG. 29A), then enters a duct (156) parallel to the second wing (11), being locked there by a locking means (18), as described above for example with reference to Plate 28 in the figures. Preferably the entrance to this duct, or even the entire outer face of the second wing (11) is provided with a gutter or a groove (157) designed to receive the ligament (L) so as to avoid having the latter projecting too far outside the implant and snagging neighboring tissues for example. Likewise, it can be seen in FIG. 29A that the ligament re-emerges from the implant on a lateral face, at the exit of the duct (156) in the implant and this free end can be cut if it is too long, so as to avoid having it snag neighboring tissues for example. It is understood that for such an embodiment, the ligament is preferably first run into the duct (12) in the first wing, then hooked through a hole made previously in the upper spinous process, then inserted into the passage (100) in the implant, then hooked around the lower spinous process, and finally run into the duct (156) in the implant, leaving enough slack in the ligament to facilitate the manipulation of the ligament (L) and of the implant (1). Then, by inserting the first wing (12) then the body (10) between the spinous processes, the surgeon can progressively pull on the ligament to apply the two wings of the implant against the spinous processes, then lock the ligament.

It is understood from reading the present application, while examining Plates 28 and 29, that an implant with an insert and a ligament can be contemplated which is peri-spinous for both spinous processes or trans-spinous for both spinous processes, by combining the various designs described above. The various types of possible combinations of the various embodiments described will also be understood. In addition, it is understood that by using a peri-spinous ligament (L) for the two spinous processes, this ligament (L), particularly when it passes within the gutters or grooves (157) along the insert (2) and/or the wings (11, 12), makes it possible to hold the insert (2) and the wings (11, 12) of the implant pressed against the lateral surfaces of the spinous processes, which provides a resource for compressing the spinous processes (for example and in particular by applying pressure on the lateral faces) stabilizing the implant, in addition to the stabilization provided by the peri-spinous hooking accomplished by the ligament (L). Thus, certain embodiments provide compression of the spinous processes for stabilizing the implant by allowing the wings (11, 12) and the retention arrangement to be pressed against the lateral surfaces of the spinous processes. Such a compression of the spinous processes can be accomplished, for example, with an implant that includes compression resources arranged so that the wings (11, 12) and the retainers (2, 3, 4, 7, 111, 121, 221, 24, 28, 29, L, 90) are pressed against the lateral surfaces of the spinous processes.

In certain embodiments, the compression of the spines is obtained by the retainer itself, without requiring additional means, resources, or arrangement. For example, FIGS. 42A through 42C and 43A through 43D show embodiments wherein the compression can be obtained directly by the retainers. FIGS. 43, 44, 45, 46, 47 and 48 also show additional examples of embodiments in which compression of the spinous processes is achieved thanks to the retainers themselves. These figures show a double insert with two parts articulated about a common hinge. This structure will be designated for the following description of these embodiments as including two inserts (2) pivoting relative to one another about a common hinge (250), even though these two inserts are in fact two parts of one and the same structure inserted into the implant (the terms "insert" or "double insert" will thus be used interchangeably in the singular or plural, which is also the case for the term "retainer"). In this example, each of these two inserts (2) includes a curved plate (or body) separated into two branches (253, 254), over at least a posterior portion of the curved plate, such that the two inserts can be nested one inside the other as previously explained with reference to possible variations for the embodiments such as those of FIGS. 1A through 1C and 2A through 2C. Thus, one branch (253) of each insert (2) passes between the two branches (253, 254) of the other insert (2) and the two inserts (2) can be inserted at the same time into the passage (15) and follow their opposite paths without interfering. Preferably, the two inserts are connected by a common hinge (250), at their posterior end, enabling the deployment of the two inserts from a folded position where the inserts are in contact or close to each other to a deployed position in which the inserts are spaced from one another. The deployment of two inserts takes place in these embodiments due to the hinge and the contact of the inserts with at least one wall in the passage (i.e., at least one wall located in the axis of the passage and opposite the entrance of the latter), and the degree of deployment (i.e., the orientation of the inserts in the deployed position) depends on the position of the hinge in the passage. Such a hinge is preferably formed by an articulation axis (250) on which are assembled, free to rotate, the posterior ends of the branches (253, 254) of each of the two inserts (2), for example thanks to eyelets (260) formed at these posterior ends. The axis (250), for example formed by a pin, screw, rivet, or other structure, may include, at a first end, a cap (252) forming a stop for retaining one of the inserts (2) in translation along the axis (250), the other insert then also being retained by its nesting with the first one. Preferably, the eyelet (260) of the branch (254) which comes to a stop against this cap (252) includes an enlargement (264) forming a shoulder for receiving and stopping the cap (252). This enlargement makes it possible to receive the cap (252), preferably in such a way that the latter does not project from the insert (2) once the ensemble is assembled, for example as shown in FIGS. 42A and 42C. Further, the axis is preferably provided at the second end with a thread accepting a nut (251), but other clamping structures may be used. In these embodiments proposing compression of the spines, the pin may be longer than the height of the two inserts that are slipped onto it, such that this nut (251) can be held at a distance from the second insert. As is particularly visible in FIGS. 43A and 43C, this ensemble is inserted into the passage (15) of an implant (1) provided with two wings (11, 12) on the same lateral face of the body (10) and this passage splits into two in the direction of the upper and lower surfaces of the body to guide each of the two inserts (2) in the direction of one of the spines. This passage is preferably provided with a longitudinal opening (158) on the upper edge of the body (10), that is to say the edge that will be situated in the direction rearward of the patient. This longitudinal opening has dimensions designed to receive the articulation pin (252) of the two inserts (2) and allow it to slide along the opening as the inserts penetrate into the passage (thanks to the space or gap between the nut and the second insert which allows the pin to slide along the opening). The nut (251) may be arranged so that it can be tightened against the edges of the opening (158) in order to be able to block the position of the pin (in translation along the opening) and of the insert (2) in the body of the implant. It is understood that thanks to this arrangement the pin and the two inserts can be positioned according to the width of the spines and that thanks to the pivoting of the inserts about the pin and to their curvature, a compression of the spines between the inserts (2) and the wings (11, 12) of the implant can be obtained. The degree of compression depends on the position of the pin in the passage (15) and of the nut (251) along the opening (158). Indeed, the position of the nut determines the orientation of the two inserts because of their deployment thanks to their contact with at least one wall of the passage (15) in the implant and this orientation (or the degree of deployment) will determine the compression of the spinous processes. By adjusting this position, more or less complete pivoting of the two inserts (2) which bear on the bottom of the passage (15) is obtained, and the compression of the spines can be maintained by locking this position by tightening the nut (251) which presses the double insert against the inner wall of the body wherein the opening (158) is provided, using the cap (252) of the pin (250).

In certain of these embodiments, an implant equipped with two inserts having a common hinge can be supplied pre-assembled with the inserts, in the folded position, inside the implant. A pin (81), such for example as that shown in FIGS.

43A and 43B, can for example be provided for blocking the two inserts within the implant. Such a pin includes a shank (814) which passes between the branches of the two inserts assembled on their common hinge, as is particularly visible in FIG. 43B. Contact of the branches (253, 254) of the two inserts (2) with the walls of the passage (15), on the one hand, and the shank (814) of the pin (81), on the other hand, prevents the inserts from further entering and/or leaving the passage (15) inopportunely. Additionally, a notch (159) can be provided in the opening (158) of the passage to receive a rib or a boss present on the pin. Thus, blocking of translation of the ensemble is completely provided for. In addition, the pin can include a head (812) including a stop (830) conforming to the outer shape of the nut (251) such that it cannot loosen inopportunely. Also, the pin can be provided with a stem (810) so that it can be more easily withdrawn when the implantation of the implant is in progress, when it is desired to proceed with the positioning of the inserts (2). Such a stem (810) can be provided, for example, with a cap (811) at its end make it easier to grip. Further, as can be seen in FIG. 43C, the entrance to the passage (15) can be flared, for example by means of at least one chamfer (154), so as to facilitate the insertion of the inserts (2) into the passage (15). It will be understood from the foregoing that an implant is thus available which can be pre-assembled with its two inserts. It is then sufficient to insert the implant having generally a T shape between the spines until the wings (11, 12) of the latter are pressed against the same lateral face of the two spines, then to withdraw the pin (81) so as to be able to press on the inserts (2) at their common hinge until the desired compression of the spines is obtained, then to tighten the nut (251) to lock the ensemble into the interspinous space. Preferably the body of the implant, the passage and the inserts (2) with their pin will be dimensioned so that even during maximum compression of the spines, the nut remains on the same lateral face as that by which the elements are inserted into the interspinous space. Thus, for example, the nut (251) remains accessible from the same implantation side, so as to minimize the invasiveness of the operation, in particular by preserving the supraspinous and inter-spinous ligaments (which could possibly be slightly pressed upon by the nut driving instrument, but which preferably will not have to be cut or damaged).

Preferably, this type of implant provided with two inserts having a common hinge will be made of durable material. Metal or PEEK will generally be preferred because the large upper and lower openings of the passages (15) that are necessary for the pivoting of the inserts and the opening (158) for guiding the inserts' pin impose heavy constraints on an implant of reduced size (suited to interspinous spaces).

It will be noted that in FIGS. 43A through 43D, the implant is provided with wings (11, 12) which are not exactly aligned in the plane of the implant's height (XY plane designed to be substantially parallel to the sagittal plane of the vertebral column), but are slightly oblique, to conform to the shape of the spines. Indeed, the spines are often thicker at their base than at their peak. Implants can therefore be provided, the wings (11, 12) of which are oriented so as to better conform to this shape of the spines. This alternative configuration applies of course to all the embodiments described in the present application, whether an implant with a dual, sigmoid or other kind of insert is considered. Thus, the considerations provided in the present application regarding an orientation of the wings (11, 12) of the implant (1) in the sagittal plane must not be interpreted in a limiting way, but rather as including the possibility of a slight oblique offset, this concept being developed with reference to the implantation of the implant between the spines as previously mentioned. It will further be noted that it is also possible to provide in certain embodiments of an implant with two inserts having a common hinge that the curved plate forming the inserts not have the same thickness from one insert to the other, so that the inserts are also arranged to conform to the shape of the spines. However, it will sometimes be preferable to have two identical inserts for obvious reasons of manufacturing cost, given that they can be assembled symmetrically and that it is not necessary to produce different types of inserts to make an assembly such as that of FIGS. 42A and 42C for example. Finally, it will also be noted that points (111, 121) are preferably provided on the wings (11, 12) of the implant, designed to penetrate into the lateral faces of the spines upon compression. Thus, the implant also adjusts itself in relation to the spines thanks to the length of these points and the stability of the implant is improved while still providing adequate compression. This further justifies a preference for two identical inserts rather than inserts of variable thickness because the improvement in production cost does not occur to the detriment of quality and stability of the implant. On the other hand the inserts (2) in these embodiments are preferably provided with notches (29) rather than points, to be able to pivot and lie along the spinous process more easily during compression and thus position themselves in the best way possible on the lateral faces of the spines. These notches (29) can be omitted but they are preferred for their stabilizing role.

Preferably, this type of implant receiving two inserts having a common hinge is provided with holding arrangements (150), formed for example of a threaded hole near at least one corner of the implant, on the side of the wings (11, 12) and oriented obliquely (between the sagittal plane and the coronal plane, preferably closer to the sagittal), to allow gripping along an oblique axis facilitating access to the interspinous space, while allowing access for a tightening tool for driving the nut. It is generally preferred to use two holding arrangements (150) to provide good holding and to have a lever arm available for acting on the implant, as already explained in the present application. Preferably, these embodiments with pivoting inserts are provided with a first holding arrangement (or attachment resource) formed by a threaded hole and a second attachment resource formed by a simple hole, to facilitate assembly of the implant on an implantation instrument (by requiring only a single screw). The second attachment resource is preferably located on the same side of the implant, on the same side edge and with the same orientation as the primary attachment resource, but near the opposite corner. This type of implant is preferably implanted using a specific instrument (5) of the type exemplified in FIGS. 44A and 44B. This instrument preferably includes a main tube (50), preferably provided with a handle (51) for gripping it. In some embodiments, a thumb wheel (52) is provided for adjusting the tightening of at least one step (500) arranged in the tube and penetrating into the holding arrangement (150) of the implant (for example a threaded rod for a threaded hole). As explained above, two holding arrangements are preferred on the implant. In the case of implants with double pivoting insert, it is generally preferred to provide for the implant, at the back (referring to the patient, that is to say the face disposed toward the rear of the patient), a threaded hole (150) and a simple hole (151). Thus, for example, the main tube (50) contains a threaded rod (500) configured to be screwed into the threaded hole (150) and the instrument has a branch (502) parallel to the main tube (50) and including a pin at its end to enter the simple hole (151). This branch (502) emanates, for example, from the main tube (50) by extending parallel to it, down to the implant. The space between the main tube (50) and branch (502) extending from it is sized so that the clamping/locking nut (250) of the pivoting inserts can pass between the main tube (50) and branch (502) during the introduction of the inserts into the body of the implant and during their deployment. In addition, a driving rod (55) of the instrument is mounted so as to pivot about a pin (53) on the tube (50) for driving the two inserts by pushing on their posterior end, as can be seen in FIGS. 44A and 44B for example. The end of this driving rod is preferably provided with an end (555) curved towards the implant mounted on the principal tube (50) (and the branch (502) parallel to it) for pushing effectively on the inserts, and preferably with a reinforcement such as a rib (5550) for example, to avoid having the end bend under the influence of the large forces exerted during compression. In addition, the driving rod is preferably guided by an axis (559), such as a pin for example, perpendicular to the tube to avoid having it twist when it is driven. This axis (559) is preferably provided with at least one stop for limiting the travel of the driving (actuating) rod. Such a stop could for example be arranged to limit the approach of the driving rod (55) from the principal tube (50), which prevents unintended actuation of the driving (actuating) rod (55) and/or limits the thrust of the insert in the implant. A stop can also, alternatively or in addition to the previous stop (FIG. 44A represents the two stops in the form of rings), be provided to limit the distance between the driving rod (55) and tube (50), which facilitates manipulation of the instrument. Such a stop can allow the inserts, introduced in the implant and deployed until they contact the spinous processes, to be maintained in position by the driving rod (55), leaving the surgeon's hands free, for example to screw the locking nut on the axis of the inserts to lock the position of inserts and the implant. The stop(s) is(are) preferably adjustable along the guiding axis (559), in order to be set according to the need. Preferably, the two stops (limiting the approach and spacing) have complementary configurations. These stops can be, for example, rings mounted at adjustable positions along the guide axis (559). For example, the axis can be a threaded rod and rings can be tapped, but various types of stops or rings can be provided with a position that can be moved along the axis and secured to prevent any further movement.

In some of the embodiments with double inserts such as those detailed above, the compression is determined by the deployment of the inserts (the orientation of the inserts) obtained as a function of the displacement of their hinge in the body of the implant and freezed (locked) by immobilizing the hinge of the double insert at the desired position (for example by tightening the nut in the examples described above). In some embodiments of implants with double inserts pivoting with respect to each other, at least one stop for locking the pivoting of the two inserts can be provided, and configured so that the inserts, deployed through the passage, can't fold back on themselves (and get out from the passage). With such a stop, when a deployed position (configuration) is reached, the locking of the inserts in this deployed position helps bringing the inserts in the direction of the spinous processes, so as to adjust the compression of the spinous processes without the inserts changing their orientation The compression can then be freezed (locked) by immobilizing the hinge of the double insert at the desired position (for example by tightening the nut in the examples described above). For example, in the case of a common hinge equipped with an axis (e.g., a pin and a nut) sliding along the longitudinal opening, as described above, it is possible to pull the pin and/or nut, to set their position relative to the body of the implant, for adjusting the compression of the spinous processes. This allows the compression to be adjustable by the position of inserts deployed in the body rather than, or in addition to, adjusting the orientation of the inserts (i.e., the level or degree of deployment of inserts) as in the embodiments described above. It will be noted that in the case of a plurality of locking stops, the level or degree of deployment can be chosen using one or another of these stops to determine the orientation of the inserts pivoting with respect to each other, so as to optimally match the shape of the lateral faces of the spinous processes (which are more or less curved and rarely perfectly flat, with a section rather elliptical which can be matched at best, by the shape of the curved inserts if their best orientation is properly adjusted). Thus, the inserts deployed with the optimum orientation relative to the lateral faces of the spinous processes are locked in this position and can be pressed more or less strongly against these lateral faces of the spinous processes by adjusting the position of inserts with a displacement in a direction approximately perpendicular to the sagittal plane (i.e., in the Z direction). However, in such cases with several locking stops, the compression may also occur by the deployment itself (depending on the deployed position reached and the size of the spinous processes) and an additional compression can be applied by the displacement of the inserts. Such stops may be formed for example by at least one notch formed on each of the two inserts with an orientation complementary to each other. For example, FIGS. 45A and 45B are embodiments of such inserts provided with teeth or notches (2531, 2541) allowing to lock the two inserts in the deployed position. In these embodiments, for example, the eyelet (260) of the upper branch/arm (253) of the lower insert has a notch (2531) on its lower surface and the eyelet of the lower branch/arm (254) of the upper insert has a notch (2541) on its upper surface (the terms "upper" and "lower" being used here in reference to the figures available and to the disposition of the inserts along the axis (250) forming the hinge on which the eyelets are mounted, the upper part of the pin being the one receiving the nut). Each of these notches (2531, 2541) comprises a first surface having a slope configured so that during the deployment of inserts, the eyelet of each insert pivots relative to the other eyelet due to the fact that the two branches (253, 254) of each of the inserts depart from each other (spread apart) gradually by the contact of these slopes of opposite orientations (due to the elasticity of the inserts, even if this elasticity may be low since the notches are of small size). Note that the branches of the inserts are sized relative to the passage in the body of the implant in order to be able to spread apart. These notches (2531, 2541) each include a second surface forming an abutment surface (with opposite orientation from one eyelet to the other), configured to oppose to the rotation of the inserts in the direction of the folded position. Thus, the two inserts can be rotated during deployment thanks to the spreading apart of their branches and get locked in the deployed position by their respective notch engaging each other spontaneously by the return of the two branches to their normal positioning. Note that it is possible to provide a release mechanism, for example such as at least one housing (2540) on the periphery of at least one eyelet and configured to receive the flat head of a tool (such as a screwdriver for example) which, through rotation of the flat head, allows to spread the branches apart and release the two notches, for example during the actuation of the two inserts in the direction of folding (towards the folded position). Note also that it is possible to provide the notches between the lower branches (254) of the two inserts or, preferably, between the upper branches (253) of the two inserts (the upper surface of the upper eyelet for the lower insert and the lower surface of the upper eyelet for the lower insert). This limits the spreading necessary between the branches to one of the inserts (respectively lower or upper) and thus facilitate the deployment of the inserts, but also to limit the extent to which the passage should be larger than the two inserts (parallel to the shaft or axis (250) of the inserts) to allow pivoting. In these examples with a single notch, the slope formed by the notch for allowing the spreading of the branches of the insert is very smooth, such that the spreading is progressive and thus facilitated. However, if several notches are desired, it is more important for the notches to be close enough to each other to provide locking positions which are useful, that is with a sufficient extent (degree) of deployment. The smaller the distance between the notches, the higher the slope of each notch. Thus, if a fine (precise) setting is desired, it is necessary to provide for notches close to each other, with slopes allowing the spreading of the branches despite their steep inclination. It will be understood here that the two inserts lock each other spontaneously in the deployed position by the fact that the distance between the branches of the inserts (at rest, in the absence of contact between the slopes of the notches) is equal to the dimension of eyelet (parallel to the axis (250) rotation) in the portions where the eyelet does not have notches. It will be noted that, conversely, it is possible to provide some embodiments in which the spacing of branches is greater than or equal to the size of the eyelet in the portions where the notches are. In this case, the lock is not spontaneous but occurs during the tightening of the nut (251) on the axis (250), tending to crush the branches (against each other and against the inner wall of the passage in the body of the implant), when the notches thereby engage each other. These types of embodiments allow more easily to obtain a fine/precise setting thanks to notches which are close to each other because the constraints of a slope allowing the spreading of the branches no longer exists. Thus, in some such embodiments where the engagement is achieved by tightening the nut (251), it is easier to provide several notches on each of the eyelets (such as shown in FIG. 45C) or several notches on the eyelet of an insert and at least one rib on the eyelet of the other insert taking place between these notches. In these embodiments with a plurality of locking stops, a locking is possible in several different deployed positions (different relative orientations of the two inserts), depending on the optimum orientation chosen, as described above. In the illustrative and non-limiting example shown on FIG. 45C, the two eyelets are equipped with a plurality of notches. It will be noted that, around the portions bearing the notches, for each eyelet having these notches, openings are provided for receiving the notches of the other eyelet in various deployed positions. These opening of each eyelet are dimensioned, in degrees around the central axis of the eyelet, as a function of the desired number of deployed positions. Furthermore, these openings are dimensioned, in height (parallel to the central axis of the eyelet), as a function of the respective size of the notches on each eyelet (for example of the order of half the height of the notches). Thus, when the notches of the two eyelet are engaged with notches of the other eyelet, the notches which are not engaged in notches of the other eyelet are received in the openings without disturbing the engagement of the notches, preferably by allowing that the eyelets contact each other on their whole circumference.

In some of these embodiments with lockable pivoting double inserts, the compression obtained by displacing the hinge of the inserts towards the entrance of the passage (15) in the implant can be performed using a compression instrument (2550). FIGS. 48A, 48B and 48C show illustrative and non-limiting examples of such instrument (2550). Such an instrument (2550) has for example two arms (2551, 2552) mounted to pivot about an axis in the manner of a clamp. A first arm (2552) preferably includes contact resources (2558) for pressing against the hinge between the two inserts. In embodiments where the hinge of the double insert includes a pin and a nut, the contact resources (2558) are preferably contacting the axis rather than the nut, to exert pressure more evenly distributed across the two pivoting inserts. In some embodiments, for example as shown in FIG. 48A, a second arm (2551) has one end bearing against the implant, preferably near the entrance of the passage, and formed for example by a spatula (2557). It will be noted that the spatula (2557) and both arms are generally configured so that the instrument is not oriented in the sagittal plane but obliquely towards the lateral face from which the inter-spinous space is accessed, to facilitate handling and minimize congestion at the levels of the spinous processes. In the examples of FIGS. 48A, 48B and 48C, the contact resources (2558) are formed by a finger entering the longitudinal opening of the body along which slides the axis (250) of the inserts, so as to push on this axis (preferably below the nut, so as to leave free access to the latter). In these examples, the first arm (2552) has one end (2559) deported from (i.e., non colinar even if it's preferably parallel to) the axis of the first arm (2552) and at the end of which is disposed the finger forming the contact resources (2558), preferably collinear with the axis of the arm (2552). Thus, the contact resources (2558) is aligned with the clamping axis while the end bearing it is deported so as to leave around the nut (251) of the inserts a space needed for the introduction of a screwing tool of the nut (such as a wrench or nut driver, for example) so as to freeze (lock) the compression thus obtained. Note however that this example is not limiting and that it is possible to provide other shapes and arrangements for the end and the contact resources (2558), such as and end having the shape of a plate, comprising a recess for the screwing of the nut and comprising a finger for pressing against the axis. It will be understood that the instrument preferably makes it possible to achieve compression while allowing access for locking the inserts when the desired compression is obtained. In addition, it is possible to provide, for example, kind of a rack mechanism (2556) to lock the approach of the two arms (2551, 2552) during the compression.

In other embodiments of lockable pivoting double inserts, such as the illustrative and non-limiting examples shown in FIGS. 46A and 46B, the compression of the spinous processes may be achieved through traction resources (255, 256, 257) fitted on the double inserts. In these figures, for example, such traction resources (255, 256, 257) are formed by at least one loop (255), preferably flexible, mounted on at least one ring connected to the pivoting double inserts. For example at least one ring provided with a first eyelet through which passes the loop can be designed to pull on the inserts which have been locked in the deployed position. The figures show two rings (256, 257) of this type, each receiving one end of the loop (255). Such rings can be formed directly on the eyelet of the inserts in a predetermined position so as not to interfere with insertion of the inserts (in the folded position) in the passage (15) of the body (such as in FIG. 46A) and be oriented towards the entrance of the passage in the body when the inserts are deployed through the implant (such as in FIG. 46B). In other embodiments, such rings may have a second eyelet configured to be slipped onto the shaft (250) of the two inserts, like the eyelets of the latter. These rings (256, 257) are thus free to rotate around the axis and their orientation can be adjusted before tightening the nut, which despite the disadvantage of limiting the size of the eyelet inserts, may have several advantages, especially in cases where inserts have several locking stops allowing several possible deployment positions. Note also that traction resources formed by at least one ring (256, 257) of the type described above can be provided, the first eyelet of such ring being configured to directly receive a tool for pulling the double inserts to which it is linked. However, for ease of handling, it is generally preferred to use a loop (255) on such ring, such loop being easier to grasp to achieve traction to obtain compression of spinous processes. These various embodiments may be associated with a compression instrument (2550), for example as shown in FIGS. 47A, 47B and 47C. Such a compression instrument (2550) is then actuated to perform a pull instead of pressure as shown in FIG. 48A, for example. This compression instrument (2550) may have two arms (2551, 2552) pivoted around an axis set to depart from each other when the instrument is operated. A first arm then has hooking resources (2555) to enter the traction resources (255, 256, 257) of the inserts. For example, a curved finger (2555) can be threaded through the loop (255) to pull on the inserts as shown in FIGS. 47B and 47C. In some embodiments, for example as shown in FIGS. 47B and 47C, a second arm (2551) has one end bearing against the implant, preferably near the entrance of the passage, for example formed by two branches (2553, 2554) separated by a distance allowing the traction resources to be actuated to pull the inserts. Such instrument preferably leaves enough space on the implant and/or insert for freezing (locking) the compression thus obtained, for example by immobilizing the hinge of the double insert at the desired position (e.g., by tightening the nut in the examples described above). In addition, it is possible to provide kind of a rack or ratchet mechanism (2556) to lock the position of both arms (2551, 2552) during the compression achieved through traction. Note that the compression instruments (2550) described above, operated in compression (such as in FIG. 48) or traction (such as in FIG. 47) may actually contain only the first arm (2552) acting on the inserts, but in this case, the arm will be configured to be mounted on an implantation instrument (5), such as those described herein. Indeed, the various embodiments of the implantation instruments (5) described herein are configured to hold the implant and often contain at least one axis (56) on which is mounted an actuating rod (55). It is possible to provide for the actuating rod (55) to be removable and for the first arm of the compression tools (2550) to be configured to be mounted in the place of the actuating rod and perform the compression or traction as described here. These embodiments can limit the number of instruments needed, but changing instruments may be preferable and both possibilities are thus considered.

It is thus understood that various embodiments allow the compression of the spinous processes by the retainer(s) itself (themselves), in particular when comprising a double pivoting insert with a lockable deployment. This compression, performed by a traction or a pressure on the insert, is obtained by displacing the deployed insert towards the entrance of the passage. These embodiments also present the advantage that such an insert locked in the deployed position is capable of matching at best the shape of the spinous processes, and in particular when the two spinous processes, between which the implant is introduced, don't have the same width (i.e., the same dimensions between their lateral faces, that is along the axis Z). Indeed, the two inserts of such double deployed insert will be pressed against a lateral face of each spinous process and, because the respective passage for these inserts in the body of the implant is larger than the dimensions of these inserts, the latter can orient through the passages for matching at best the lateral faces of the spinous processes, even by positioning themselves not parallel to the sagittal plane if required by the configuration of the spinous processes. Most of the embodiments providing double insert with lockable deployment thus offer a compression of both spinous processes even when the latter don't have the same dimensions, one with respect to the other.

In certain embodiments, the compression of the spinous processes is obtained due to the fact that the implant includes additional specific compression resources or arrangements (16, 19). These embodiments are generally used when fusion is desired, but can be useful for improving stabilization without necessarily obtaining fusion. It will be noted as well that in these embodiments, the wings (11, 12) and/or the insert (2) can be provided with notches (29) and/or points (11, 121, 221) arranged so as to allow better retention of the spinous processes (by slightly penetrating into the lateral surfaces of the spinous processes), but that it is also possible to not provide them, even though they are generally preferred, particularly when fusion and/or compression is desired. Various illustrative and non-limiting examples of such compression arrangements (16, 19) are shown in the figures of plates 36, 37, 38, 39 and 40. It will be noted that the points (111, 121, 221) used in these embodiments are preferably of reduced size with respect to the anchoring arrangements described in the present application because here it is preferred to simply avoid slipping of the spinous processes without necessarily penetrating too deeply into the bony tissue. These various examples have the advantage, as do most of the elements described in the present application, of allowing implantation by a unilateral approach to the spinous processes, and generally with reduced invasiveness. In these embodiments with a pivoting insert, it is generally preferred that the body of the implant be made of metal because these embodiments require the provision of more ducts, passages, recesses and grooves than other embodiments. Thus the strength of the implant is a constraint that can be easily overcome with a body made of metal rather than of PEEK.

Generally, in these examples the compression arrangements (16, 19) are arranged so as to press, against a lateral surface of each of the adjacent spinous processes, a sigmoid insert (2) constituting the retention resources of the implant. This insert (2) and the passage (15) in the body (10) are arranged so that the insert (2) is able to pivot inside the body (10) to accomplish the compression of the spinous processes under the influence of the compression arrangement (16, 19). Preferably, the insert (2) pivots thanks to rotation about at least one axis arranged so as to be oriented substantially along the Y axis, in the sagittal plane (A) wherein are aligned the two adjacent spinous processes between which the implant is inserted. Thus the pivoting of the implant is accomplished symmetrically with respect to the center of the interspinous space and allows reliable compression, ensuring better stability. This axis of rotation is generally obtained by at least one interior surface of the passage (15) against which the insert bears during its pivoting obtained by driving the compression arrangements. This bearing surface is preferably curved and, in certain embodiments, the bearing point of the insert moves along this surface during pivoting of the insert and thus performs translation in addition to the rotation. Indeed, a certain amount of play can be provided so that the insert pivots more easily and its position in the passage adjusts according to the configuration of the spinous processes between which it is inserted. For example, in FIGS. 36B and 36C which show the implant in a top view but show by transparency the passage (15) and the insert (2), it is observed that the insert (2) bearing on part of the surface of the passage (15) before pivoting, can be located bearing on another part of this surface of the passage after pivoting. This type of configuration, with a slight play of the insert within the passage, may possibly allow compensation for the fact that the two adjacent spinous processes do not necessarily have the same thickness and require that compression be asymmetrical on the two sides of the implant.

In certain embodiments, an example of which is shown in FIGS. 36A, 36B and 36C, the compression arrangements (16, 19) include at least one screw (16) running through a duct (163) in the body (10) and opening into the passage (15) of the insert (2) at a point located above (toward the upper spine ES) or below (toward the lower spine E1) the pivoting axis of the insert (2). Thus, by driving this screw (16), for example by its screw head (160), which includes for example a hexagonal cavity (164), the portion (161) of the screw (16) which penetrates into the body (10) presses on the insert (2) and causes it to pivot, which allows the anterior and posterior ends of the insert to approach the lateral surfaces of the spinous processes and exert a compression force on the latter thanks to the wings (11, 12) of the implant lying along the opposite faces. In these embodiments, the passage (15) visible by transparency in the example of FIGS. 36B and 36C is preferably arranged so as to be larger than the thickness of the insert so that the latter is able to pivot. In addition, in this example, at least part of a surface of the walls of the passage (15) serves as an abutment for the insert and thus constitutes the axis of rotation about which the insert (2) pivots. As mentioned above, this axis of rotation can actually move along this bearing surface, if it is desired to adjust the positioning of the insert (2). FIGS. 36B and 36C show that the portion (161) of the screw (16) which penetrates into the body projects into the passage (15) at the level of the insertion stop (25) of the insert (2). This portion (161) of the screw (16) therefore provides a stop surface so that the insertion stop (25) carries out its task and stops the advance of the insert into the passage. In addition, the insert (2) can include a withdrawal stop (20) such as a flexible lug as detailed in other embodiments and the body will then be arranged so that the stop surface (122) receiving the free end of this finger (20) is arranged so that the finger comes to rest against the stop surface (122) of the body once the insert has pivoted. It can be seen for example that in FIG. 36B where the insert (2) has not yet pivoted, the finger (20) is not yet in its recess while in FIG. 36C where the insert (2) has pivoted, the finger (20) is located in its recess and then acts as a withdrawal stop. It can be provided, as before, that this recess be accessible from outside the body by means of a duct (120), as shown in FIG. 36C. It will be noted that it is also possible to provide that the flexible lug (20) of the insert is arranged on the insert in such a way that it is bearing on a complementary surface (122) of the passage located as close as possible to the axis (or successive axes) of rotation of the insert during pivoting. Thus, continuous locking of the insert is obtained without too much play, instead of obtaining locking only in the position where the insert has pivoted and is compressing the spinous processes. In this case, it will be preferred not to be able to facilitate the adjustment of the insert in the event of asymmetry of the spinous processes, but to have some play to make the attachment more reliable.

In these embodiments, the compression arrangement (16, 19) is therefore oriented substantially perpendicularly to the alignment plane of the spinous processes (generally the sagittal plane), which has the advantage that the driving of this compression arrangement (turning of the screw for example) results directly in thrust on the insert. However, this arrangement is not ideal for driving the compression arrangement because the approach to the lateral face of the spinous processes is not always possible. It is then necessary to resort to a tool the end whereof is curved (as for example an Allen key) to be able to drive the compression arrangement from below (i.e. the rear of the patient). Other embodiments therefore provide for compression arrangements the driving whereof can be accomplished from above (that is from the rear of the patient). Various examples of such embodiments are shown in the figures of plates 37, 38, 39, 40 and 41.

In these embodiments where driving takes place from above, the screw (16) may constitute the driving arrangement of a compression arrangement (19) consisting of a pivoting latch. In most of these embodiments, this screw (16), accessible from above, not only makes it possible to more easily drive the compression arrangements, but it can also constitute a holding arrangement allowing the implant to be held by an instrument as detailed in other embodiments. Indeed, it is observed on the illustrative and non-limiting examples of the figures of plates 37, 38, 39, 40 and 41 that the screw (16), with its recess (164) provides a holding arrangement (150) similar to that described in other embodiments with reference to the implantation instrument (5). This recess (164) makes it possible to receive the end of the stem (500) of the instrument (5). Here, the instrument can have a stem (500) which is not threaded and the end (560) whereof has a section complementary to the internal shape of the recess (164) of the screw (16). Preferably, such a stem is combined with a hook (520) oriented along an axis that is not parallel with that of the stem (500) and which enters the lateral recess (151) of the body to ensure proper holding of the implant (1) on the end of the instrument (5). FIGS. 41B and 41D show an example of the use of such an end (560) of the stem (500) for holding the implant, but also for driving the compression arrangements.

Certain examples illustrating these embodiments of the compression arrangements (16, 19) drivable from the top (i.e., from above) of the implant are shown in FIGS. 37A, 37B, 37C and 37D. FIGS. 37B and 37D show a section view of such an implant wherein the compression arrangements (16, 19) include a driving arrangement (16) and a transmission arrangement (19). In particular, the transmission arrangement (19) includes a latch (191) mounted within a recess (192) inside the body (10) and pivoting about an axis of rotation (190) oriented along the Z axis. The driving arrangement (16) can consist of a screw (161) the head (160) of which is accessible and drivable from the top of the implant, for example thanks to a recess (164) provided for the insertion of a tool. This screw (161) penetrates into a duct (163) provided in the body (10) and opening onto the latch (191). The end (165) of the screw opposite the head (160) can thus press on the latch, for example by means of a finger (165) having a rounded tip. The latch (191) preferably has substantially the shape of a plate the orientation whereof is aligned with that of the duct (163) of the screw and the axis of rotation (190) is offset with respect to the axis of the duct (163) such that the thrust exerted by the screw (161) when it is driven causes rotation of the plate about that axis. It is observed for example in FIGS. 37B and 37D that this eccentric axis (190) above the duct allows pivoting of the latch (191) when the screw (161) is driven into the duct (163). The latch (191) then presses on the insert which is inserted in the passage (15) of the implant, which tends to make it rise and pivot thanks to at least part of a bearing surface constituting at least an axis of rotation in the passage (15). In the examples shown in FIGS. 37A and 37C, the latch (191) presses against the insertion stop (25) formed by a thickening of the insert. This insertion stop (25) extends beyond at least one edge of the insert to bear on a chamfer (105) on the edge of the passage (15). Thus, when the insert (2) pivots, its insertion stop (25) remains bearing against this chamfer (105) at the edge of the entrance of the passage (15) in the body (10). In these embodiments, the withdrawal of the insert can be prevented, as detailed in other embodiments, by a flexible lug (20) bearing against a surface (122) along the walls of the passage (15).

FIGS. 38A, 38B, 38C and 38D show other embodiments of an implant wherein the compression arrangements (16, 19) include a driving arrangement (16) and a transmission arrangement (19). In particular, the transmission arrangement (19) includes a latch (191) mounted in a recess (192) within the body (10) and pivoting about an axis of rotation (190) oriented along the Y axis. The driving arrangement (16) can consist of a screw (161) the head (160) of which is accessible and drivable from the top (above) of the implant, for example thanks to a recess (164) provided for the insertion of a tool. This screw (161) penetrates into a duct (163) provided in the body (10) parallel to the axis of rotation of the latch, and opening onto the recess (192) of the latch (191) oriented perpendicularly to the duct (163) of the screw and so arranged as to only partially obstruct the duct (163) when it is in the lower position. The end of the screw opposite the head (160) can thus press on the latch, for example by means of a finger with a rounded or pointed tip or one including at least one bevel, such that the tightening of the screw (161) in the duct allows this end to press the latch upward and causes it to pivot. The latch (191) preferably has the shape of a plate the orientation whereof is perpendicular to that of the duct (163). FIGS. 38B and 38D show an example of this actuation (pivoting) of the latch (191) by tightening the screw (161). The latch (191) then presses on the insert which is inserted into the passage (15) of the implant, which tends to cause it to rise and to pivot thanks to at least part of a bearing surface constituting at least one axis of rotation in the passage (15). In the examples shown in FIGS. 38A and 38C, the latch (191) presses against the insertion stop (25) formed by a thickening of the insert. This insertion stop (25) extends beyond at least one edge of the insert to bear on a chamfer (105) on the edge of the passage (15). Thus, when the insert (2) pivots, its insertion stop (25) remains bearing against this chamfer (105) on the edge of the entrance of the passage (15) in the body (10). In these embodiments, the withdrawal of the insert can be prevented, as detailed in other embodiments, by a flexible lug (20) bearing against a surface (122) along the walls of the passage (15). It will also be noted here that in the examples of FIG. 37, the body (10) preferably includes a holding arrangement (151) on one of its lateral faces, to receive a hook (520) of an instrument (5) as explained in the present application. In FIG. 38, such a holding arrangement can be obtained by the fact that the recess (192) of the latch can open onto the lateral face of the insert and can have sufficient dimensions, compared with those of the latch, to receive such a hook (520).

FIGS. 39A, 39B, 39C and 39D show other embodiments of an implant wherein the compression arrangements (16, 19) have a driving arrangement (16) and a transmission arrangement (19). These examples are similar to those of FIG. 38, but the latch (191) also has a bevel to facilitate its cooperation with the pointed or rounded or beveled end of the screw (161), as can be seen in FIGS. 39B and 39D. Another difference relates to the fact that the latch has an extension (195) serving as a withdrawal stop (and consisting in this example of a plate oriented perpendicularly to the plate forming the pivoting latch). In such embodiments, it is possible to dispense with a flexible lug (20) as a withdrawal mechanism because the extension (195) of the latch conforms to the insertion stop (25). This insertion stop and the extension are preferably arranged so that their reciprocal contact surfaces are oriented so as to oppose withdrawal of the insert. Another difference in this example is that a supplementary holding arrangement (151) has been provided in the body to receive the hook (520) of an instrument (5) of the same type as those described in the present application.

FIGS. 40 and 41 show other embodiments of an implant wherein the compression arrangements (16, 19) include a driving arrangement (16) and a transmission arrangement (19). For example, the transmission arrangement (19) includes a pivoting cam (191) mounted free to rotate in the passage (15) and with a through passage that is continuous with the passage in the body for insertion of the insert. The axis of rotation of this cam is oriented along the Y axis, and the pivoting takes place in the frontal (or coronal, that is formed by the XZ axes) plane. The driving arrangement (16) can consist of a screw (161) the head (160) whereof is accessible and drivable from the top (above) of the implant, for example thanks to a recess (164) arranged for the insertion of a tool. This screw (161) penetrates into a duct (163) provided in the body (10), parallel to the axis of rotation of the cam (191) and opening into a recess (192) wherein an extension (193), oriented perpendicularly to the duct (163) of the screw, is arranged so that it obstructs only partially the duct (163) when it is in the lower position. The pivoting of the cam (191) is accomplished thanks to the thrust of the screw (16) on the extension (193) forming a lever arm for actuating the rotation of the cam (191), thanks to an inclined surface (1930) of the extension (193) against which the end, preferably rounded or backward sloping, of the screw presses when the screw is driven, as is particularly visible in FIGS. 41B and 41D. The end of the screw opposite the head (160) can thus press on the latch, for example thanks to a finger with a rounded or pointed end or one having at least one bevel, so that driving the screw (161) into the duct allows this end to push the extension (193) upward, which drives the cam in rotation. The rotation of the cam (191) drives the insert in rotation thanks to contact between the insert and at least part of a surface of the walls of the passage in the cam. Locking of the insert can be obtained by a recess in the cam (191) containing the stop surface (122) receiving the free end of a flexible lug (20) in the same manner as described in other embodiments (FIG. 40C for example). It will be noted that the rotation of the insert (and the rotation of the cam) can be limited or not by the length of the travel of the extension (193) in the recess (192) of the body, but it is possible to provide a larger recess so that it is only the thickness of the spinous processes that limits the rotation of the insert. In addition, it will also be noted that the embodiments using a cam as in the examples shown in FIG. 40 are 41 are generally preferred because the large leverage forces for obtaining compression during driving are exerted on parts of greater dimensions than in the examples of FIGS. 37, 38 and 39. Thus, a more reliable device is obtained, the driving of which is facilitated.

Another distinct aspect of the present invention relates to an instrument (5) for implanting an interspinous implant (1), preferably an implant according to the invention. For example, an embodiment of the instrument may include at least one means (500, 520) for gripping an implant (1) which includes at least one anchorage (150, 151) to receive the said gripping means (500, 520). For example, FIG. 12B shows examples of anchorage means (150, 151) on the implant, which may, for example, be embodied as sockets, housings, posts, notches, or other attachment structures (preferably female means on the implant). The instrument also preferably includes at least one actuating means (55), movable with respect to the gripping means (500, 520) and arranged to drive the insert (2) into the implant (1) when it is actuated.

FIGS. 14A through 15B illustrate an example of an instrument (5) for placing (implanting) an interspinous implant (1).

Figure 14A:
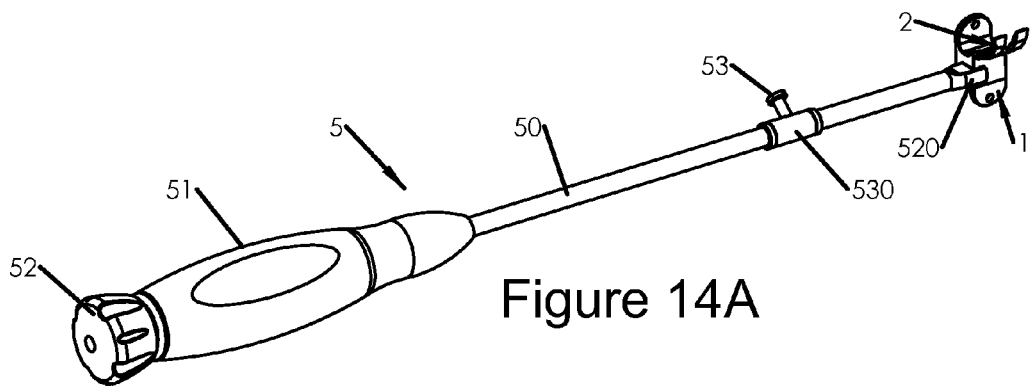
FIGS. 14A and 14B show a perspective view and a longitudinal section view, respectively, of an implantation instrument for interspinous implants according to certain embodiments, FIG. 14C showing an enlargement of the area 14C indicated on FIG. 14B.
Figure 14C:
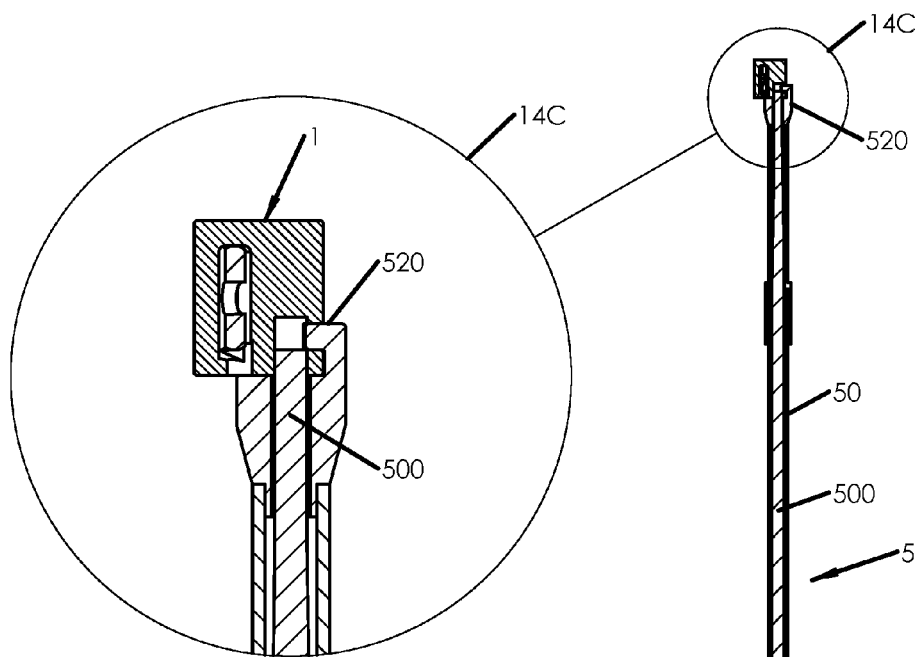
Figure 14B:
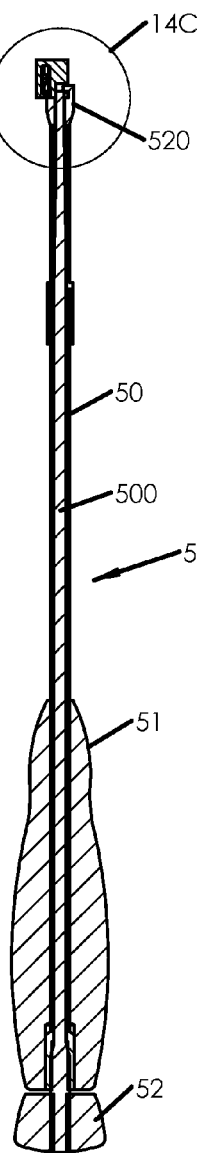

As shown in the examples in FIGS. 14A through 14C, the instrument (5) includes for instance a tube (50) on which is mounted a handle (51) for holding the instrument and at the end of which is mounted a thumb wheel (52) allowing actuation of a rod (500) movably mounted within the tube.

The gripping means (500, 520) includes an internal rod (500) and a hook (520) located on a head attached to the end of the tube (50) as can be seen particularly in FIG. 14C. The rod (500) that is movable with respect to the tube (50) of the instrument (5) is arranged so that one of its ends enters a complementary socket (150) which constitutes the anchorage on the implant (1). This rod can be threaded to cooperate with a tapped thread in the socket (150) of the implant (1) and can suffice instead of also requiring a hook, although it is preferable to add a hook to provide better retention of the implant and preferably its manipulation in several planes in space. It is nonetheless possible to provide an unthreaded rod and even one with a non-circular section (the socket (150) having a complementary shape) and to combine it with a hook (520) oriented along an axis that is not parallel to that of the rod, provided that a means is provided for locking the rod in position within the implant, with respect to the hook, or at least insofar as the stem (500) of the instrument (5) can be held in the recess (150) of the implant (for example by manually holding the stem in position, even though it is preferable to be able to lock it in order to have one's hands free). Thus for example, the rod should be lockable with respect to the tube (50) which bears the hook, preferably with a thread/tap which also makes possible a fine adjustment of the rod's position by turning the rod.

Figure 15A:
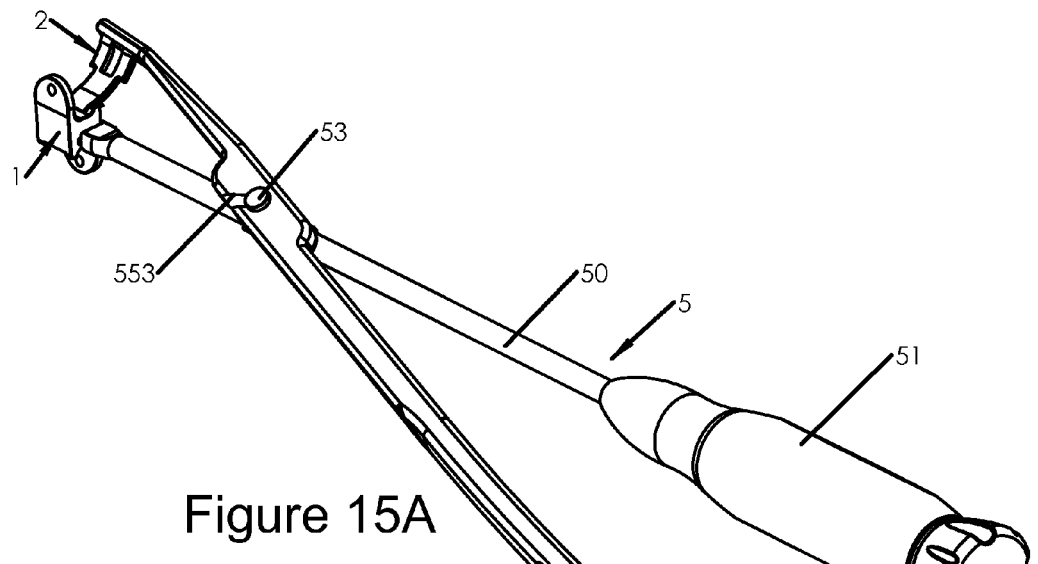
FIGS. 15A through 15B show two perspective views of an instrument equipped with actuating means for insertion of an insert into the body of an interspinous implant according to certain embodiments, in the deployed and in the actuated position, respectively, FIG. 15C showing an enlargement of the area 15C indicated on FIG. 15B.
Figure 15B:
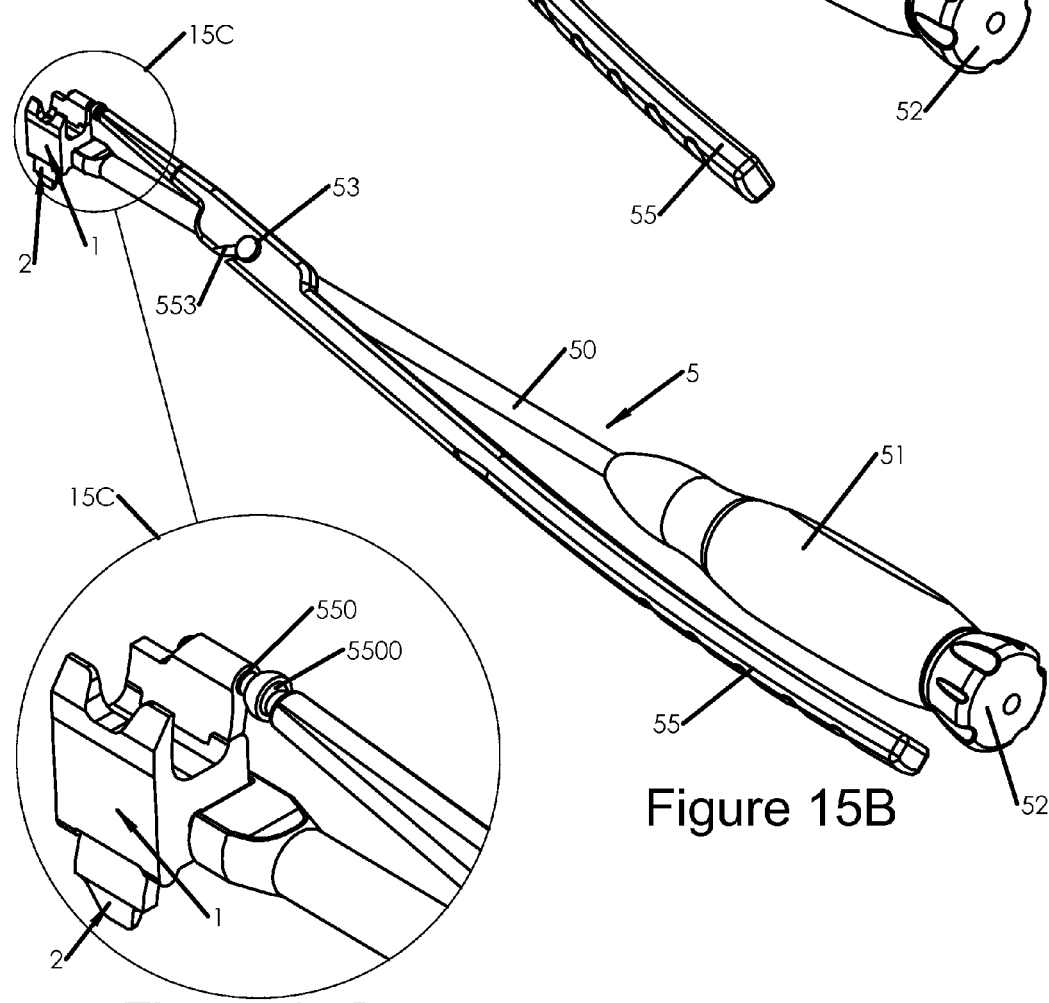
Figure 15C:
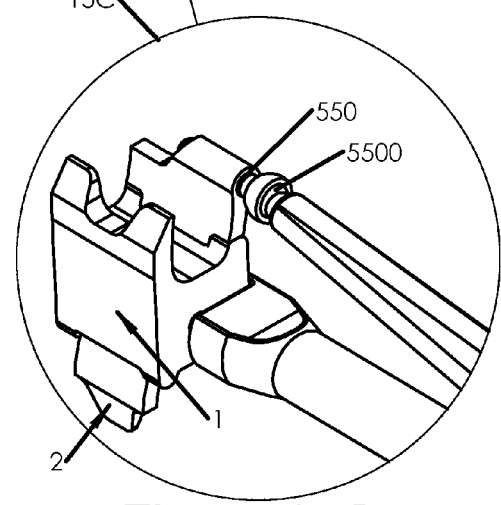

Moreover, for the actuation means of the instrument, an actuating rod (55) can be provided, which is movable with respect to the gripping means (500, 520) and arranged to drive the insert (2) into the implant (1) upon its actuation. This rod (55) is preferably pivotably mounted around a stud (53) set on a support which is itself mounted around the tube (50) of the instrument to allow the stud to revolve around the tube (50) during actuation of the rod in the direction of the tube and thus to facilitate the manipulation of the insert (2), in particular the sigmoidal one, driven by the end of the actuating rod (55) using, for example, means (26) of holding the insert (2) as described in the present application, or simply by a thrust surface on the posterior end of the insert (2). This actuating rod (55) is inserted for example on the stud (53) by means of an indentation (553), which facilitates the addition of the actuating rod (55) to the (50) of the instrument. In the case of a rod or finger entering the cylindrical holding means (26) (e.g., a ring) of the insert, this finger will preferably be designed to mount on the end of the actuating rod (55) through a ball joint allowing the finger to pivot during actuation of the actuating rod (55), for example as shown in FIGS. 15B and 15C and as particularly visible on FIG. 15C.

In certain embodiments, the actuating means, instead of consisting of a rod pivoting around a stud like a pair of pliers as explained above, consist of a sort of driveshaft or jackshaft. These actuating means then include a shaft (55) with its longitudinal axis parallel to the tube (50) of the instrument and mounted so as to rotate about its longitudinal axis. This rotating shaft (55) is preferably retained relative to the tube (50) by attachment, holding or retention means leaving the shaft (55) free to rotate about its longitudinal axis, and preferably also free in translation along its longitudinal axis. Such holding means can be obtained for example by a connector (540) that is fixed with respect to the tube (50) and/or by running the shaft (55) through the handle (51) of the instrument, as shown for example in FIG. 24A. At the front end (where the implant is held), the shaft (55) is mounted fixed in rotation, and preferably also in translation, to an arm (542) the axis of which is generally perpendicular to the longitudinal axis of the shaft (55). At the rear end (by which the instrument is held), the rotating shaft (55) is mounted fixed in rotation, and preferably also in translation, to a crank (541) allowing the shaft to be actuated so as to turn it, thus driving the arm (542) to cause the insert (2) to enter the implant (1), in the manner of a driveshaft or jackshaft. Preferably, the arm (542) is provided at its end with a pin or a finger (550) parallel to the longitudinal axis of the shaft (55), as shown for example in FIG. 24B. This finger (550) is designed to enter a holding means (26) in the insert (2), such as an eyelet or a ring for example (or even a blind hole, though a structure extending on the full width of the insert plate is preferred) as explained above for the pivoting finger (550) in other embodiments of the instrument (5). Thus, translation of the shaft (55) relative to the tube (50) allows insertion of the finger (550) into the eyelet in the insert (2), even when the insert is already engaged in the entrance to the passage in the implant already mounted on the instrument (5). Preferably, the finger (550) is mounted free to rotate on the arm (542) and/or has dimensions slightly smaller than those of the eyelet (26) in the insert, so as to facilitate rotation of the finger (550) in the eyelet (26). It will be understood that the shapes and dimensions of the arm (542) are designed according to the shapes and dimensions (particularly the curves) of the insert (2), so that the rotational movement of the shaft (55) obtained by operating the crank (541) results in a movement of the finger (550) at the end of the arm (542) which guides the insert (2) into the implant (1) as shown in FIGS. 24A, 24B, 24C and 24D. In addition, the crank (541) is preferably longer than the arm (542) so that the actuation of the crank provides a lever arm which the shaft (55) transmits to the arm (542).

The placement of the interspinous implant (1) may, for example, be carried out by insertion of the implant (with the insert or inserts) from the same face of the two dorsal spines, for example the face (E4) illustrated in FIGS. 17a, 17b and 17c. In this event, the body (10) is first set between the dorsal spines (EI, ES) through a lateral face of a dorsal spinous process. Then the insert (2) is set in a second step in the passage (15) of the body (10) bearing on a lateral face of at least one dorsal spine (EI, ES). Finally, in a third step, the insert (2) is retained in the body (10) at the end of its movement within the passage (15).

It is understood from the functional descriptions provided in reference to the various technical features detailed in the present application that various embodiments could be selected depending on the condition of the interspinous space wherein the implant is to be implanted, as well as the condition of the surrounding structures. For example, for an interspinous space exhibiting a slight instability, an implant will be preferred that leaves the spines free to move slightly and therefore includes only retention arrangements for the implant to hold it stable, but without arrangements for fixing or hooking the spines. If, however, the instability of the interspinous space and of the surrounding structures is greater, it may be preferred to limit the movement of the spines by providing hooking resources for the spines. In these configurations, the various arrangements disclosed in the present application could be selected to provide the stabilization that is desired (e.g., fixed hooks of more or less flexible material, hooks of rigid or flexible material held by a flexible link, rigid and fixed hooks, etc.). If it is desired to stabilize unstable spines even more strongly, compression arrangements or hooking resources held rigidly, or even bone anchorage arrangements, could be selected. Thus, the various embodiments described in the present application offer various stabilization possibilities while still guaranteeing reduced invasiveness and ease of implantation.

A person skilled in the art will understand from reading the present application that various embodiments of the implants described make it possible to respond to at least one of the problems mentioned, and certain embodiments may have all the advantages that make it possible to respond to the full set of problems. The implants described in the present application are made of implantable material(s), preferably transparent to x-rays but provided with markers (that is to say comprising at least one radio-opaque portion). Preferably, the dimensions and positions of the markers within the implant will be arranged so as to minimize interference with imaging means. The markers will for example be as small as possible and set as far as possible from the vertebral canal to avoid "flash" problems with scanners.

The implants can be made of, but are not limited to, PEEK or polyether-etherketone materials which have elasticity similar to that of cortical bone.

The curved plate inserts can for example, but without limitation, be made of metal, for example titanium or titanium alloy.

The present application describes several technical features and advantages with reference to the figures and/or to various embodiments. A person skilled in the art will understand that the technical features of a given embodiment can in fact be combined with features of one or more other embodiments, unless the contrary is explicitly stated or the features are incompatible or the combination will not work. For example, anti-slip means such as notches (29) of wings and/or inserts can be combined with bone anchorage means (3, 111, 121, 221, 7, 28) and/or with bone-growth material (8). More generally, combinations of various types of implant retainer and/or of retainers for the spinous processes are contemplated and will be understood by those skilled in the art using the functional and structural considerations provided in the present application. In addition, the technical features described in a given embodiment can be isolated from other features of that embodiment unless the contrary is explicitly stated, particularly as the operational considerations provided in the present application will provide sufficient explanation that the structural adaptations that may be necessary will be within reach of a person skilled in the art.

Persons skilled in the art, after fully appreciating the present disclosure, will understand that embodiments in many other specific forms than the ones detailed herein are within the scope of the invention as claimed. Consequently, the present embodiments should be considered as illustrations, but can be modified within the field defined by the scope of the appended claims, and the claims should not be limited to the details given above.

The invention claimed is:

1. An interspinous implant for implantation between a first dorsal spine and an adjacent second dorsal spine comprising:
   an insert comprising
      an upper plate having a hinged end and a free end,
      a lower plate having a hinged end and a free end,
      a hinge attached to the hinged end of each of the upper and lower plates and articulating the upper plate and the lower plate from an insertion position in which the free ends of the upper plate and the lower plate are disposed proximally to an extended position in which the free ends of the upper plate and the lower plate are disposed on opposite sides of the hinge; and
   a body comprising
      a top, a bottom, a left side, a right side, a front, and back,
      an upper wing disposed proximal to the right side of the body and extending away from the top of the body,
      a lower wing disposed proximal to the right side of the body and extending away from the bottom of the body,
      a hollow channel in the body comprising
         a first opening disposed on the right side of the body and sized to admit the free ends of the upper and lower plates into the channel with the hinge in the insertion position, and
         a second opening distal from the first opening disposed to emit the free ends of the upper and lower plates with the hinge in the extended position, with the free end of the upper plate adjacent to the upper wing and the free end of the lower plate adjacent to the lower wing, the second opening being divided by a surface placed to deflect the free end of the upper plate upward and a surface placed to deflect the free end of the lower plate downward.

2. The interspinous implant if claim 1 further comprising a pin forming the hinge.

3. The interspinous implant if claim 2 further comprising a nut fitted to the pin and disposed outside the channel, and tightening the nut fixes the insert within the channel.

4. The interspinous implant of claim 3 in which the channel further comprises a slot disposed on the front of the body and connected to the opening, the slot having a width sufficient to for the pin to move in the channel with the nut adjacent the slot.

5. The interspinous implant of claim 1 further comprising a loop attached to the hinge and accessible from the first opening.

6. The interspinous implant of claim 5 in which the hinged end of each of the upper plate and the lower plate comprises plural teeth, with the teeth of the upper plate selectively engagable with the teeth of the lower plate in plural configurations in which the insert is locked into one of plural extended positions.

* * * * *